(12) United States Patent
Zhang et al.

(10) Patent No.: US 11,840,575 B2
(45) Date of Patent: *Dec. 12, 2023

(54) ENGINEERED IMMUNE CELLS TARGETING BCMA AND THEIR USES THEREOF

(71) Applicant: GRACELL BIOTECHNOLOGIES (SHANGHAI) CO., LTD., Shanghai (CN)

(72) Inventors: Hua Zhang, Shanghai (CN); Huan Shi, Shanghai (CN); Lianjun Shen, Shanghai (CN); Wei Cao, Shanghai (CN); Liping Liu, Shanghai (CN)

(73) Assignee: GRACELL BIOTECHNOLOGIES (SHANGHAI) CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/041,977

(22) PCT Filed: May 6, 2020

(86) PCT No.: PCT/CN2020/088836
§ 371 (c)(1),
(2) Date: Sep. 25, 2020

(87) PCT Pub. No.: WO2020/224606
PCT Pub. Date: Nov. 12, 2020

(65) Prior Publication Data
US 2022/0049004 A1    Feb. 17, 2022

(30) Foreign Application Priority Data
May 7, 2019    (CN) .......................... 201910376652.8

(51) Int. Cl.
*C07K 16/28* (2006.01)
*A61P 35/00* (2006.01)
(Continued)

(52) U.S. Cl.
CPC .......... *C07K 16/2878* (2013.01); *A61K 35/17* (2013.01); *A61P 35/00* (2018.01);
(Continued)

(58) Field of Classification Search
None
See application file for complete search history.

(56) References Cited

U.S. PATENT DOCUMENTS 5,350,674 A    9/1994    Boenisch et al.
5,399,346 A    3/1995    Anderson et al.
(Continued)

FOREIGN PATENT DOCUMENTS

CN    105142677 A    12/2015
CN    105658671 A    6/2016
(Continued)

OTHER PUBLICATIONS

Jena et al. (Blood Aug. 19, 2010 116(7): 1035-1044) (Year: 2010).*
(Continued)

*Primary Examiner* — Peter J Reddig
(74) *Attorney, Agent, or Firm* — Wilson Sonsini Goodrich & Rosati

(57) ABSTRACT

The present invention provides an engineered immune cell targeting BCMA and use thereof. In particular, the present invention provides a CAR specifically targeting BCMA, the CAR comprising an antigen-binding domain which is an S-derived scFv, an antibody heavy chain variable region as shown in SEQ ID NO: 9 and an antibody light chain variable region as shown in SEQ ID NO: 10. The present invention also provides a CAR-T cell comprising the CAR, a double (Continued)

CAR- and CAR-T cell comprising the S-derived scFv, and related use thereof. Compared to CAR-T cells constructed using other scFvs, the constructed CAR-T cell of the present invention has a better killing effect and tumor elimination capability.

28 Claims, 23 Drawing Sheets

Specification includes a Sequence Listing.

(51) Int. Cl.
  A61K 35/17    (2015.01)
  C07K 14/725   (2006.01)
  C07K 14/71    (2006.01)
  A61K 38/00    (2006.01)
  A61K 39/00    (2006.01)

(52) U.S. Cl.
  CPC .......... C07K 14/7051 (2013.01); C07K 14/71 (2013.01); C07K 16/2803 (2013.01); A61K 38/00 (2013.01); A61K 2039/505 (2013.01); C07K 2317/31 (2013.01); C07K 2317/53 (2013.01); C07K 2317/622 (2013.01); C07K 2317/76 (2013.01); C07K 2319/02 (2013.01); C07K 2319/03 (2013.01); C07K 2319/30 (2013.01); C07K 2319/33 (2013.01)

(56) References Cited

U.S. PATENT DOCUMENTS

| | | | |
|---|---|---|---|
| 5,580,859 A | 12/1996 | Felgner et al. | |
| 5,585,362 A | 12/1996 | Wilson et al. | |
| 5,589,466 A | 12/1996 | Felgner et al. | |
| 5,641,870 A | 6/1997 | Rinderknecht et al. | |
| 6,326,193 B1 | 12/2001 | Liu et al. | |
| 7,741,465 B1 | 6/2010 | Eshhar et al. | |
| 7,838,637 B2 | 11/2010 | Kontermann et al. | |
| 8,399,645 B2 | 3/2013 | Campana et al. | |
| 9,328,156 B2 | 5/2016 | June et al. | |
| 9,447,194 B2 | 9/2016 | Jensen | |
| 9,464,140 B2 | 10/2016 | June et al. | |
| 9,499,629 B2 | 11/2016 | June et al. | |
| 9,765,342 B2 | 9/2017 | Kochenderfer | |
| 9,834,590 B2 | 12/2017 | Campana et al. | |
| 9,856,322 B2 | 1/2018 | Campana et al. | |
| 10,266,608 B2 | 4/2019 | Wu | |
| 10,287,350 B2 | 5/2019 | Kochenderfer | |
| 10,301,391 B2 | 5/2019 | Raum et al. | |
| 10,513,686 B2 | 12/2019 | Ostertag et al. | |
| 10,519,251 B2 | 12/2019 | Wu | |
| 10,550,183 B2 | 2/2020 | Png et al. | |
| 11,078,291 B2 | 8/2021 | Sussman et al. | |
| 11,353,458 B2 | 6/2022 | Bounds et al. | |
| 11,440,958 B2 | 9/2022 | Png et al. | |
| 11,634,502 B2 | 4/2023 | Yan et al. | |
| 11,639,387 B2 | 5/2023 | Jensen | |
| 11,673,945 B2 | 6/2023 | Imhof-Jung et al. | |
| 2009/0155275 A1 | 6/2009 | Wu et al. | |
| 2010/0260668 A1 | 10/2010 | Ghayur et al. | |
| 2013/0287748 A1* | 10/2013 | June ................... | C07K 14/7051 435/328 |
| 2016/0303230 A1 | 10/2016 | Ahmed et al. | |
| 2016/0333108 A1* | 11/2016 | Forman .............. | C07K 16/2803 |
| 2017/0233484 A1* | 8/2017 | Sussman ............... | A61P 35/00 424/133.1 |
| 2018/0306791 A1 | 10/2018 | Bounds et al. | |
| 2019/0350978 A1 | 11/2019 | Beauchesne et al. | |
| 2020/0223918 A1 | 7/2020 | Ma et al. | |
| 2021/0163893 A1 | 6/2021 | Westoby et al. | |
| 2021/0220404 A1 | 7/2021 | Abujoub et al. | |
| 2022/0168389 A1 | 6/2022 | Ghassemi et al. | |
| 2022/0202864 A1* | 6/2022 | Zhang ................. | A61K 48/005 |
| 2022/0364055 A1 | 11/2022 | Treanor et al. | |

FOREIGN PATENT DOCUMENTS

| | | | |
|---|---|---|---|
| CN | 108778329 A | 11/2018 | |
| CN | 109485734 A * | 3/2019 | ............. A61K 35/17 |
| WO | WO-0129058 A1 | 4/2001 | |
| WO | WO-0196584 A2 | 12/2001 | |
| WO | WO-2010104949 A3 | 11/2010 | |
| WO | WO-2012079000 A1 | 6/2012 | |
| WO | WO-2016014565 A2 | 1/2016 | |
| WO | WO-2017143069 A1 | 8/2017 | |
| WO | WO-2017149515 A1 | 9/2017 | |
| WO | WO-2018106732 A1 | 6/2018 | |
| WO | WO-2018151817 A2 | 8/2018 | |
| WO | WO-2019232444 A1 | 12/2019 | |
| WO | WO-2020047452 A2 | 3/2020 | |
| WO | WO-2020088631 A1 | 5/2020 | |

OTHER PUBLICATIONS

Gura (Science, 1997, 278:1041-1042) (Year: 1997).*
Kaiser (Science, 2006, 313: 1370) (Year: 2006).*
Zhang et al. (Blood Nov. 13, 2019 134 (Suppl. 1): 3147) (Year: 2019).*
Joseph Sambrook et al., "Molecular Cloning: A Laboratory Manual", Cold Spring Harbor Laboratory Press, vol. 1, 1-18, 2001.
Nicholson et al. Construction and characterisation of a functional CD19 specific single chain Fv fragment for immunotherapy of B lineage leukaemia and lymphoma. Mol Immun 34(16-17):1157-1165 (1997).
Steven Rosenberg et al., Use of Tumor-Infiltrating Lymphocytes and Interleukin-2 in the Immunotherapy of Patients with Metastatic Melanoma. In: New England Journal of Medicine. 1988 ; vol. 319, No. 25. pp. 1676-1680.
Ui-Tei et al., Sensitive assay of RNA interference in *Drosophila* and Chinese hamster cultured cells using firefly luciferase gene as target. FEBS Lett. Aug. 18, 2000;479(3):79-82. doi: 10.1016/s0014-5793(00)01883-4. PMID: 10981711.
International Search Report and Written Opinion along with Translation of PCT/CN2020/088836 dated Aug. 13, 2020.
Nicholson et al., Construction and characterisation of a functional CD19 specific single chain Fv fragment for immunotherapy of B lineage leukemia and lymphoma, Molecular Immunology, vol. 34, Issues 16-17,1997, pp. 1157-1165.
Zhang et al., Development in Bispecific Antibody, Chinese Journal of Pharmaceutical Analysis, vol. 39, No. 1, figure 1, and the abstract, Jan. 31, 2019.
Zola et al., Preparation and characterization of a chimeric CD19 monoclonal antibody. Immunol Cell Biol. Dec. 1991;69 ( Pt 6):411-22. doi: 10.1038/icb.1991.58. PMID: 1725979.
Berahovich et al.: CAR-T Cells Based on Novel BCMA Monoclonal Antibody Block Multiple Myeloma Cell Growth. Cancers (Basel) 10(9):323, pp. 1-16. doi:10.3390/cancers10090323 (2018).
Bluhm et al.: CAR T Cells with Enhanced Sensitivity to B Cell Maturation Antigen for the Targeting of B Cell Non-Hodgkin's Lymphoma and Multiple Myeloma. Mol Ther. 26(8):1906-1920. doi:10.1016/j.ymthe.2018.06.012 (2018).
Cohen et al.: B cell maturation antigen-specific Car T cells are clinically active in multiple myeloma. J Clin Invest. 129(6):2210-2221. doi:10.1172/JCI126397 (2019).
EP Application No. 20801569.3 Extended European Search Report dated May 16, 2023.
Jayaraman et al.: CAR-T design: Elements and their synergistic function. EBioMedicine. 58:102931, pp. 1-12. doi:10.1016/j.ebiom.2020.102931 (2020).
Kulemzin et al.: Engineering Chimeric Antigen Receptors. Acta Naturae. 9(1):6-14 (2017).
PCT/CN2020/088836 English translation of the International Search Report and Written Opinion dated Aug. 13, 2020.

(56) References Cited

OTHER PUBLICATIONS

Sterner et al.: CAR-T cell therapy: current limitations and potential strategies. Blood Cancer J. 11(4):69, pp. 1-11. doi:10.1038/s41408-021-00459-7 (2021).

* cited by examiner

SEQUENCE LISTING

```
<160> NUMBER OF SEQ ID NOS: 40

<210> SEQ ID NO 1
<211> LENGTH: 22
<212> TYPE: PRT
<213> ORGANISM: Artificial Sequence
<220> FEATURE:
<223> OTHER INFORMATION: GM-CSF signal peptide

<400> SEQUENCE: 1

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 2
<211> LENGTH: 20
<212> TYPE: PRT
<213> ORGANISM: Artificial Sequence
<220> FEATURE:
<223> OTHER INFORMATION: 2A peptide

<400> SEQUENCE: 2

Gly Ser Gly Ala Thr Asn Phe Ser Leu Leu Lys Gln Ala Gly Asp Val
1               5                   10                  15

Glu Glu Asn Pro
            20

<210> SEQ ID NO 3
<211> LENGTH: 112
<212> TYPE: PRT
<213> ORGANISM: Artificial Sequence
<220> FEATURE:
<223> OTHER INFORMATION: CD3z signaling region

<400> SEQUENCE: 3

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 4
<211> LENGTH: 41
<212> TYPE: PRT
<213> ORGANISM: Artificial Sequence
<220> FEATURE:
<223> OTHER INFORMATION: CD28 signaling region

<400> SEQUENCE: 4

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 5
<211> LENGTH: 42
<212> TYPE: PRT
<213> ORGANISM: Artificial Sequence
<220> FEATURE:
<223> OTHER INFORMATION: 41BB signaling region

<400> SEQUENCE: 5

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 6
<211> LENGTH: 27
<212> TYPE: PRT
<213> ORGANISM: Artificial Sequence
<220> FEATURE:
<223> OTHER INFORMATION: CD28 transmembrane region

<400> SEQUENCE: 6

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 7
<211> LENGTH: 24
<212> TYPE: PRT
<213> ORGANISM: Artificial Sequence
<220> FEATURE:
<223> OTHER INFORMATION: CD8 transmembrane region

<400> SEQUENCE: 7

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 8

```
<211> LENGTH: 45
<212> TYPE: PRT
<213> ORGANISM: Artificial Sequence
<220> FEATURE:
<223> OTHER INFORMATION: CD8 hinge region

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 9
<211> LENGTH: 121
<212> TYPE: PRT
<213> ORGANISM: Artificial Sequence
<220> FEATURE:
<223> OTHER INFORMATION: S scFv heavy chain

<400> SEQUENCE: 9

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Tyr Ile Asn Pro Asn Ser Gly Tyr Thr Asn Tyr Ala Gln Lys Phe
    50                  55                  60

Gln Gly Arg Ala Thr Met Thr Ala Asp Lys Ser Ile Asn Thr Ala Tyr
65                  70                  75                  80

Val Glu Leu Ser Arg Leu Arg Ser Asp Asp Thr Ala Val Tyr Phe Cys
                85                  90                  95

Thr Arg Tyr Met Trp Glu Arg Val Thr Gly Phe Phe Asp Phe Trp Gly
            100                 105                 110

Gln Gly Thr Met Val Thr Val Ser Ser
        115                 120

<210> SEQ ID NO 10
<211> LENGTH: 108
<212> TYPE: PRT
<213> ORGANISM: Artificial Sequence
<220> FEATURE:
<223> OTHER INFORMATION: S scFv light chain

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Ser Asp Asp
            20                  25                  30

Leu Ala Trp Tyr Gln Gln Lys Pro Gly Lys Ala Pro Lys Val Leu Val
        35                  40                  45

Tyr Thr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Thr Tyr Lys Phe Pro Pro
                85                  90                  95
```

```
Thr Phe Gly Gly Gly Thr Lys Val Glu Ile Lys Arg
            100                 105
```

```
<210> SEQ ID NO 11
<211> LENGTH: 120
<212> TYPE: PRT
<213> ORGANISM: Artificial Sequence
<220> FEATURE:
<223> OTHER INFORMATION: FMC63 scFv heavy chain

<400> SEQUENCE: 11

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

```
<210> SEQ ID NO 12
<211> LENGTH: 107
<212> TYPE: PRT
<213> ORGANISM: Artificial Sequence
<220> FEATURE:
<223> OTHER INFORMATION: FMC63 scFv light chain

<400> SEQUENCE: 12

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

```
<210> SEQ ID NO 13
<211> LENGTH: 111
<212> TYPE: PRT
<213> ORGANISM: Artificial Sequence
<220> FEATURE:
<223> OTHER INFORMATION: BB scFv heavy chain

<400> SEQUENCE: 13

Asp Ile Val Leu Thr Gln Ser Pro Pro Ser Leu Ala Met Ser Leu Gly
```

```
1               5                   10                  15
Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
            35                  40                  45

Thr Leu Leu Ile Gln Leu Ala Ser Asn Val Gln Thr Gly Val Pro Ala
            50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110
```

<210> SEQ ID NO 14
<211> LENGTH: 120
<212> TYPE: PRT
<213> ORGANISM: Artificial Sequence
<220> FEATURE:
<223> OTHER INFORMATION: BB scFv light chain

<400> SEQUENCE: 14

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
            35                  40                  45

Gly Trp Ile Asn Thr Glu Thr Arg Glu Pro Ala Tyr Ala Tyr Asp Phe
            50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser Ala Ala Ala
            115                 120
```

<210> SEQ ID NO 15
<211> LENGTH: 142
<212> TYPE: PRT
<213> ORGANISM: Artificial Sequence
<220> FEATURE:
<223> OTHER INFORMATION: April chain

<400> SEQUENCE: 15

```
Ser Val Leu His Leu Val Pro Ile Asn Ala Thr Ser Lys Asp Asp Ser
1               5                   10                  15

Asp Val Thr Glu Val Met Trp Gln Pro Ala Leu Arg Arg Gly Arg Gly
            20                  25                  30

Leu Gln Ala Gln Gly Tyr Gly Val Arg Ile Gln Asp Ala Gly Val Tyr
            35                  40                  45

Leu Leu Tyr Ser Gln Val Leu Phe Gln Asp Val Thr Phe Thr Met Gly
            50                  55                  60

Gln Val Val Ser Arg Glu Gly Gln Gly Arg Gln Glu Thr Leu Phe Arg
65                  70                  75                  80
```

```
Cys Ile Arg Ser Met Pro Ser His Pro Asp Arg Ala Tyr Asn Ser Cys
                85                  90                  95

Tyr Ser Ala Gly Val Phe His Leu His Gln Gly Asp Ile Leu Ser Val
            100                 105                 110

Ile Ile Pro Arg Ala Arg Ala Lys Leu Asn Leu Ser Pro His Gly Thr
        115                 120                 125

Phe Leu Gly Phe Val Lys Leu Ser Gly Gly Ser Asp Pro
    130                 135                 140

<210> SEQ ID NO 16
<211> LENGTH: 21
<212> TYPE: PRT
<213> ORGANISM: Artificial Sequence
<220> FEATURE:
<223> OTHER INFORMATION: CD8 signal peptide

<400> SEQUENCE: 16

Met Ala Leu Pro Val Thr Ala Leu Leu Leu Pro Leu Ala Leu Leu Leu
1               5                   10                  15

His Ala Ala Arg Pro
            20

<210> SEQ ID NO 17
<211> LENGTH: 15
<212> TYPE: PRT
<213> ORGANISM: Artificial Sequence
<220> FEATURE:
<223> OTHER INFORMATION: (G4S)3 linker peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 25
<212> TYPE: PRT
<213> ORGANISM: Artificial Sequence
<220> FEATURE:
<223> OTHER INFORMATION: (G4S)5 linker peptide

<400> SEQUENCE: 18

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 19
<211> LENGTH: 18
<212> TYPE: PRT
<213> ORGANISM: Artificial Sequence
<220> FEATURE:
<223> OTHER INFORMATION: 218 linker peptide

<400> SEQUENCE: 19

Gly Ser Thr Ser Gly Ser Gly Lys Pro Gly Ser Gly Glu Gly Ser Thr
1               5                   10                  15

Lys Gly

<210> SEQ ID NO 20
<211> LENGTH: 335
<212> TYPE: PRT
<213> ORGANISM: Artificial Sequence
<220> FEATURE:
<223> OTHER INFORMATION: EGFRt sequence
```

-continued

```
<400> SEQUENCE: 20

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
                100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
        130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
                180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
        210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
                260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
        290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 21
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 21

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Tyr Tyr Tyr Gly Gly Ser Tyr Ala Met Asp Tyr Trp Gly Gln
            100                 105                 110

Gly Thr Thr Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 23

Gln Val Lys Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Val Thr Ile Ser Lys Asp Thr Ser Lys Ser Gln Val Phe Leu
65                  70                  75                  80
```

```
Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 24

Gln Val Lys Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Ser Gln Val Phe Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 25

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
        115                 120
```

```
<210> SEQ ID NO 26
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
        115                 120

<210> SEQ ID NO 27
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 28

Gln Val Gln Leu Gln Glu Ser Gly Pro Gly Leu Val Lys Pro Ser Gln
1               5                   10                  15
```

```
Thr Leu Ser Val Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Val Ser Leu
65                  70                  75                  80

Lys Leu Ser Ser Leu Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Thr Val Thr Val Ser Ser
            115                 120
```

<210> SEQ ID NO 29
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 29

```
Gln Val Gln Leu Gln Glu Ser Gly Pro Gly Leu Val Lys Pro Ser Gln
1               5                   10                  15

Thr Leu Ser Val Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ala Ala Leu Lys
    50                  55                  60

Ser Arg Leu Thr Ile Ser Lys Asp Thr Ser Lys Asn Gln Val Ser Leu
65                  70                  75                  80

Lys Leu Ser Ser Leu Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Thr Val Thr Val Ser Ser
            115                 120
```

<210> SEQ ID NO 30
<211> LENGTH: 120
<212> TYPE: PRT
<213> ORGANISM: Artificial Sequence
<220> FEATURE:
<223> OTHER INFORMATION: CD19 antibody heavy chain variable region

<400> SEQUENCE: 30

```
Gln Val Lys Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Phe Ser Leu
```

```
                65                  70                  75                  80
Lys Leu Ser Ser Val Thr Ala Ala Asp Thr Ala Val Tyr Tyr Cys Ala
                    85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser
            115                 120

<210> SEQ ID NO 31
<211> LENGTH: 107
<212> TYPE: PRT
<213> ORGANISM: Artificial Sequence
<220> FEATURE:
<223> OTHER INFORMATION: CD19 antibody light chain variable region

<400> SEQUENCE: 31

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Gly Lys Ala Pro Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: CD19 antibody light chain variable region

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Pro Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 33
<211> LENGTH: 107
<212> TYPE: PRT
<213> ORGANISM: Artificial Sequence
<220> FEATURE:
```

<223> OTHER INFORMATION: CD19 antibody light chain variable region

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Gly Ala Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105
```

<210> SEQ ID NO 34
<211> LENGTH: 107
<212> TYPE: PRT
<213> ORGANISM: Artificial Sequence
<220> FEATURE:
<223> OTHER INFORMATION: CD19 antibody light chain variable region

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Leu Glu Ile Lys
            100                 105
```

<210> SEQ ID NO 35
<211> LENGTH: 107
<212> TYPE: PRT
<213> ORGANISM: Artificial Sequence
<220> FEATURE:
<223> OTHER INFORMATION: CD19 antibody light chain variable region

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
```

```
                65                  70                  75                  80
Glu Asp Ile Ala Thr Tyr Tyr Cys Gln Gln Gly Asn Thr Leu Pro Tyr
                    85                  90                  95
Thr Phe Gly Gly Gly Thr Lys Leu Glu Ile Lys
                100                 105
```

<210> SEQ ID NO 36
<211> LENGTH: 107
<212> TYPE: PRT
<213> ORGANISM: Artificial Sequence
<220> FEATURE:
<223> OTHER INFORMATION: CD19 antibody light chain variable region

<400> SEQUENCE: 36

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Lys Tyr
                20                  25                  30
Leu Asn Trp Tyr Gln Gln Lys Pro Gly Lys Ala Pro Lys Leu Leu Ile
                35                  40                  45
Tyr His Thr Ser Arg Leu His Ser Gly Val Pro Ser Arg Phe Ser Gly
        50                  55                  60
Ser Gly Ser Gly Thr Asp Tyr Thr Leu Thr Ile Ser Ser Leu Gln Pro
65                  70                  75                  80
Glu Asp Ile Ala Thr Tyr Tyr Cys Gln Gln Ala Asn Thr Leu Pro Tyr
                    85                  90                  95
Thr Phe Gly Gly Gly Thr Lys Leu Glu Ile Lys
                100                 105
```

<210> SEQ ID NO 37
<211> LENGTH: 49
<212> TYPE: PRT
<213> ORGANISM: Artificial Sequence
<220> FEATURE:
<223> OTHER INFORMATION: CD8 hinge region

<400> SEQUENCE: 37

```
Lys Pro Thr Thr Thr Pro Ala Pro Arg Pro Pro Thr Pro Ala Pro Thr
1               5                   10                  15
Ile Ala Ser Gln Pro Leu Ser Leu Arg Pro Glu Ala Ser Arg Pro Ala
                20                  25                  30
Ala Gly Gly Ala Val His Thr Arg Gly Leu Asp Phe Ala Ser Asp Lys
                35                  40                  45
Pro
```

<210> SEQ ID NO 38
<211> LENGTH: 47
<212> TYPE: PRT
<213> ORGANISM: Artificial Sequence
<220> FEATURE:
<223> OTHER INFORMATION: CD8 hinge region

<400> SEQUENCE: 38

```
Ser Gly Thr Thr Thr Pro Ala Pro Arg Pro Pro Thr Pro Ala Pro Thr
1               5                   10                  15
Ile Ala Ser Gln Pro Leu Ser Leu Arg Pro Glu Ala Cys Arg Pro Ala
                20                  25                  30
Ala Gly Gly Ala Val His Thr Arg Gly Leu Asp Phe Ala Cys Asp
                35                  40                  45
```

```
<210> SEQ ID NO 39
<211> LENGTH: 113
<212> TYPE: PRT
<213> ORGANISM: Artificial Sequence
<220> FEATURE:
<223> OTHER INFORMATION: CD3z signaling region

<400> SEQUENCE: 39

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Gly Gly Ser
1               5
```

ENGINEERED IMMUNE CELLS TARGETING BCMA AND THEIR USES THEREOF

TECHNICAL FIELD

The present invention relates to the field of immunotherapy, and more specifically to an engineered immune cell targeting BCMA and use thereof.

SEQUENCE LISTING

The instant application contains a Sequence Listing which has been submitted electronically in ASCII format and is hereby incorporated by reference in its entirety. Said ASCII copy, created on Sep. 29, 2022, is named 56758-711_831_SL.txt and is 36,014 bytes in size.

BACKGROUND OF THE INVENTION

Multiple myeloma (MM) is a malignant plasma cell tumor. The tumor cells originate from plasma cells in the bone marrow, and plasma cells are cells that develop to the final functional stage of B lymphocytes. Multiple myeloma is basically an incurable disease with the characteristics of high morbidity and high mortality. In 2017's statistics, there were 30,000 newly diagnosed multiple myeloma patients in the United States, among them, 12,000 might face death. At present, common therapies for multiple myeloma include cytotoxic drug therapy, protease inhibitors (Bortezomib, etc.), lenalidomide, monoclonal antibodies, corticosteroids, and the like. However, the current therapies are all partially effective, have no lasting alleviation effect, and the high risk of recurrence. Therefore, improvement in the therapies of multiple myeloma appears to be particularly important.

Therefore, there is an urgent need in the art for an effective, low-recurrence rate, and safe therapy for multiple myeloma.

SUMMARY OF THE INVENTION

An object of the present invention is to provide an engineered immune cell targeting BCMA and use thereof.

Another object of the present invention is to provide an engineered immune cell targeting both CD19 and BCMA and use thereof.

In a first aspect of the present invention, a chimeric antigen receptor (CAR) or TCR is provided, and an antigen binding domain (scFv) of the CAR or TCR comprises an antibody heavy chain variable region as shown in SEQ ID NO: 9 and an antibody light chain variable region as shown in SEQ ID NO: 10.

In another preferred embodiment, the scFv further comprises a linker peptide located between the heavy chain variable region and the light chain variable region.

In another preferred embodiment, the scFv is as shown in the following formula A or formula B:

$$V_H\text{-}V_L, \quad (A)$$

$$V_L\text{-}V_H, \quad (B)$$

in the formula, $V_H$ is the antibody heavy chain variable region; $V_L$ is the antibody light chain variable region; and "-" is a linker peptide or a peptide bond.

In another preferred embodiment, the linker peptide between the $V_H$ and the $V_L$ is 1 to 4, preferably 1 to 4, and more preferably 3 to 4 consecutive sequences as shown in SEQ ID NO: 40 (GGGGS).

In another preferred embodiment, the CAR has a structure as shown in the following formula I:

$$\text{L-scFv-H-TM-C-CD3}\xi \quad (I)$$

in the formula,

"-" is each independently a linker peptide or a peptide bond;

L is absent or a signal peptide sequence;

H is absent or a hinge region;

TM is a transmembrane domain;

C is a costimulatory signal molecule; and

CD3ξ is a cytoplasmic signaling sequence derived from CD3ξ.

In a second aspect of the present invention, a bispecific CAR or TCR is provided, and the bispecific CAR or TCR targets BCMA and a first target, wherein an antigen binding domain (scFv) targeting the BCMA in the bispecific CAR comprises an antibody heavy chain variable region as shown in SEQ ID NO: 9 and an antibody light chain variable region as shown in SEQ ID NO: 10, and the first target is selected from the group consisting of: CD138, Kappa Light Chain, NKG2D-ligands, TACI, GPRC5D, CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCRα, TCRβ, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R, TROP-2, or a combination thereof. In another preferred embodiment, the bispecific CAR or TCR comprises an antigen binding domain targeting CD19.

In another preferred embodiment, the first target is CD19, and the antigen binding domain (scFv) targeting the CD19 in the bispecific CAR comprises an antibody heavy chain variable region as shown in SEQ ID NO: 11 and an antibody light chain variable region as shown in SEQ ID NO: 12.

In another preferred embodiment, the first target is CD19, and the antigen binding domain (scFv) targeting CD19 in the bispecific CAR comprises an antibody heavy chain variable region as shown in any one of SEQ ID NOs: 21-30 and an antibody light chain variable region as shown in any one of SEQ ID NOs: 31-36.

The specific sequences are as shown below:

```
a CD19 antibody heavy chain variable region
as shown in SEQ ID NO: 21 (H9)
QVQLQESGPGLVKPSETLSLTCTVSGVSLPDYGVSWIRQPPGKGLEWLGV

IWGSETTYYNSALKSRLTISKDTSKSQVSLKLSSVTAADTAVYYCAKHYY

YGGSYAMDWGQGTLVTVSS;
``` a CD19 antibody heavy chain variable region
as shown in SEQ ID NO: 22 (H1)
QVQLQESGPGLVKPSQTLSLTCTVSGVSLPDYGVSWIRQPPGKGLEWIGV

IWGSETTYYNSALKSRVTISVDTSKNQFSLKLSSVTAADTAVYYCARHYY

YGGSYAMDWGQGTTVTVSS;

a CD19 antibody heavy chain variable region
as shown in SEQ ID NO: 23 (H8)
QVKLQESGPGLVKPSETLSLTCTVSGVSLPDYGVSWIRQPPGKGLEWIGV

IWGSETTYYNSALKSRVTISKDTSKSQVFLKLSSVTAADTAVYYCAKHYY

YGGSYAMDWGQGTLVTVSS;

a CD19 antibody heavy chain variable region
as shown in SEQ ID NO: 24 (H10)
QVKLQESGPGLVKPSETLSLTCTVSGVSLPDYGVSWIRQPPGKGLEWLGV

IWGSETTYYNSALKSRLTISKDTSKSQVFLKLSSVTAADTAVYYCAKHYY

YGGSYAMDWGQGTLVTVSS;

a CD19 antibody heavy chain variable region
as shown in SEQ ID NO: 25 (H2)
QVQLQESGPGLVKPSQTLSLTCTVSGVSLPDYGVSWIRQPPGKGLEWIGV

IWGSETTYYNSALKSRVTISKDTSKNQVSLKLSSVTAADTAVYYCAKHYY

YGGSYAMDWGQGTTVTVSS;

a CD19 antibody heavy chain variable region
as shown in SEQ ID NO: 26 (H3)
QVQLQESGPGLVKPSQTLSLTCTVSGVSLPDYGVSWIRQPPGKGLEWIGV

IWGSETTYYNSALKSRLTISKDTSKNQVSLKLSSVTAADTAVYYCAKHYY

YGGSYAMDYWGQGTTVTVSS;

a CD19 antibody heavy chain variable region
as shown in SEQ ID NO: 27 (H4)
QVQLQESGPGLVKPSQTLSLTCTVSGVSLPDYGVSWIRQPPGKGLEWLGV

IWGSETTYYNSALKSRLTISKDTSKNQVSLKLSSVTAADTAVYYCAKHYY

YGGSYAMDYWGQGTTVTVSS;

a CD19 antibody heavy chain variable region
as shown in SEQ ID NO: 28 (H5)
QVQLQESGPGLVKPSQTLSVTCTVSGVSLPDYGVSWIRQPPGKGLEWLGV

IWGSETTYYNSALKSRLTISKDTSKNQVSLKLSSLTAADTAVYYCAKHYY

YGGSYAMDYWGQGTTVTVSS;

a CD19 antibody heavy chain variable region
as shown in SEQ ID NO: 29 (H6)
QVQLQESGPGLVKPSQTLSVTCTVSGVSLPDYGVSWIRQPPGKGLEWLGV

IWGSETTYYNAALKSRLTISKDTSKNQVSLKLSSLTAADTAVYYCAKHYY

YGGSYAMDYWGQGTTVTVSS;

a CD19 antibody heavy chain variable region
as shown in SEQ ID NO: 30 (H7)
QVKLQESGPGLVKPSETLSLTCTVSGVSLPDYGVSWIRQPPGKGLEWLGV

IWGSETTYYNSALKSRLTISKDTSKNQFSLKLSSVTAADTAVYYCAKHYY

YGGSYAMDYWGQGTLVTVSS;

a CD19 antibody light chain variable region
as shown in SEQ ID NO: 31 (L5)
DIQMTQSPSSLSASVGDRVTISCRASQDISKYLNWYQQKPGKAPKLLIYH

TSRLHSGVPSRFSGSGSGTDYTFTISSLQPEDIATYFCQQGNTLPYTFGG

GTKLEIK;

a CD19 antibody light chain variable region
as shown in SEQ ID NO: 32 (L1)
DIQMTQSPSSLSASVGDRVTITCRASQDISKYLNWYQQKPGKAPKLLIYH

TSRLHSGVPSRFSGSGSGTDFTFTISSLQPEDIATYYCQQGNTLPYTFGG

GTKLEIK;

a CD19 antibody light chain variable region
as shown in SEQ ID NO: 33 (L6)
DIQMTQSPSSLSASVGDRVTITCRASQDISKYLNWYQQKPGGAVKLLIYH

TSRLHSGVPSRFSGSGSGTDYTFTISSLQPEDIATYFCQQGNTLPYTFGG

GTKLEIK;

a CD19 antibody light chain variable region
as shown in SEQ ID NO: 34 (L2)
DIQMTQSPSSLSASVGDRVTITCRASQDISKYLNWYQQKPGKAPKLLIYH

TSRLHSGVPSRFSGSGSGTDYTFTISSLQPEDIATYYCQQGNTLPYTFGG

GTKLEIK;

a CD19 antibody light chain variable region
as shown in SEQ ID NO: 35 (L3)
DIQMTQSPSSLSASVGDRVTITCRASQDISKYLNWYQQKPGKAPKLLIYH

TSRLHSGVPSRFSGSGSGTDYTLTISSLQPEDIATYYCQQGNTLPYTFGG

GTKLEIK;

and
a CD19 antibody light chain variable region
as shown in SEQ ID NO: 36 (L4)
DIQMTQSPSSLSASVGDRVTITCRASQDISKYLNWYQQKPGKAPKLLIYH

TSRLHSGVPSRFSGSGSGTDYTLTISSLQPEDIATYYCQQANTLPYTFGG

GTKLEIK.

In another preferred embodiment, the bispecific CAR comprises both an antigen binding domain targeting the first target and an antigen binding domain targeting the BCMA.

In another preferred embodiment, the bispecific CAR has a structure as shown in the following formula II:

$$\text{L-scFv1-I-scFv2-H-TM-C-CD3}\xi \quad \text{(II)}$$

in the formula,
"-" is each independently a linker peptide or a peptide bond;
L is absent or a signal peptide sequence;
I is a flexible linker;
H is absent or a hinge region;
TM is a transmembrane domain;
C is a costimulatory signal molecule;
CD3ξ is a cytoplasmic signaling sequence derived from CD3ξ; and
one of scFv1 and scFv2 is an antigen binding domain targeting the first target, and the other is an antigen binding domain targeting the BCMA.

In another preferred embodiment, the scFv1 and scFv2 can be independent of each other, can also be tandem, or in a loop structure.

In another preferred embodiment, the scFv1 is an antigen binding domain targeting the first target, and the scFv2 is an antigen binding domain targeting the BCMA.

In another preferred embodiment, the scFv1 is an antigen binding domain targeting the BCMA, and the scFv2 is an antigen binding domain targeting the first target.

In another preferred embodiment, the sequence of the flexible linker I comprises 1-6, preferably 3-5 consecutive sequences as shown in SEQ ID NO: 40 (GGGGS).

In another preferred embodiment, the flexible linker I has a sequence as shown in SEQ ID NO: 17, 18 or 19.

In another preferred embodiment, the antigen binding domain targeting the first target has a structure as shown in the following formula C or formula D:

$$V_{L1}\text{-}V_{H1} \quad (C)$$

$$V_{H1}\text{-}V_{L1} \quad (D)$$

wherein $V_{L1}$ is an antibody light chain variable region against the first target; $V_{H1}$ is an antibody heavy chain variable region against the first target; and "-" is a linker peptide or a peptide bond.

In another preferred embodiment, the antigen binding domain targeting CD19 has a structure as shown in the following formula C or formula D:

$$V_{L1}\text{-}V_{H1} \quad (C)$$

$$V_{H1}\text{-}V_{L1} \quad (D)$$

wherein $V_{L1}$ is an antibody light chain variable region against CD19; $V_{H1}$ is an antibody heavy chain variable region against CD19; and "-" is a linker peptide or a peptide bond.

In another preferred embodiment, the antigen binding domain targeting CD19 comprises the heavy chain variable region and the light chain variable region of monoclonal antibody FMC63.

In another preferred embodiment, the heavy chain variable region of the anti-CD19 antibody has an amino acid sequence as shown in SEQ ID NO: 11.

In another preferred embodiment, the light chain variable region of the anti-CD19 antibody has an amino acid sequence as shown in SEQ ID NO: 12.

In another preferred embodiment, the antigen binding domain targeting BCMA has a structure as shown in the following formula A or formula B:

$$V_H\text{-}V_L \quad (A)$$

$$V_L\text{-}V_H \quad (B)$$

in the formula, $V_H$ is the antibody heavy chain variable region; $V_L$ is the antibody light chain variable region; and "-" is a linker peptide or a peptide bond.

In another preferred embodiment, the scFv1 comprises an antibody heavy chain variable region as shown in SEQ ID NO: 11 and an antibody light chain variable region as shown in SEQ ID NO: 12; and the scFv2 comprises an antibody heavy chain variable region as shown in SEQ ID NO: 9 and an antibody light chain variable region as shown in SEQ ID NO: 10.

In another preferred embodiment, the scFv1 comprises an antibody heavy chain variable region as shown in SEQ ID NO: 9 and an antibody light chain variable region as shown in SEQ ID NO: 10; and the scFv2 comprises an antibody heavy chain variable region as shown in SEQ ID NO: 11 and an antibody light chain variable region as shown in SEQ ID NO: 12.

In another preferred embodiment, the scFv1 and/or scFv2 are murine-derived, human-derived, human- and murine-derived chimeric, or fully humanized single chain antibody variable region fragments.

In another preferred embodiment, the bispecific CAR has a structure as shown in the following formula III or III':

$$L\text{-}V_{L3}\text{-}scFv3\text{-}V_{H3}\text{-}H\text{-}TM\text{-}C\text{-}CD3\xi \quad (III)$$

$$L\text{-}V_{H3}\text{-}scFv3\text{-}V_{L3}\text{-}H1\text{-}TM\text{-}C\text{-}CD3\xi \quad (III')$$

in the formula,
"-" is each independently a linker peptide or a peptide bond;
elements L, H, TM, C and CD3ξ are as described above; and
scFv3 is an antigen binding domain targeting the BCMA, $V_{H3}$ is an antibody heavy chain variable region against the first target, and $V_{L3}$ is an antibody light chain variable region against the first target; or scFv3 is an antigen binding domain targeting the first target, $V_{H3}$ is an antibody heavy chain variable region against the BCMA, and $V_{L3}$ is an antibody light chain variable region against the BCMA.

In another preferred embodiment, the scFv3 comprises an antibody heavy chain variable region as shown in SEQ ID NO: 9 and an antibody light chain variable region as shown in SEQ ID NO: 10.

In another preferred embodiment, the $V_{H3}$ has an antibody heavy chain variable region as shown in SEQ ID NO: 9, and the $V_{L3}$ has an antibody light chain variable region as shown in SEQ ID NO: 10.

In another preferred embodiment, the scFv3 comprises an antibody heavy chain variable region as shown in SEQ ID NO: 11 and an antibody light chain variable region as shown in SEQ ID NO: 12; and the $V_{H3}$ has an antibody heavy chain variable region as shown in SEQ ID NO: 9, and the $V_{L3}$ has an antibody light chain variable region as shown in SEQ ID NO: 10.

In another preferred embodiment, the scFv3 comprises an antibody heavy chain variable region as shown in SEQ ID NO: 9 and an antibody light chain variable region as shown in SEQ ID NO: 10; and the $V_{H3}$ has an antibody heavy chain variable region as shown in SEQ ID NO: 11, and the $V_{L3}$ has an antibody light chain variable region as shown in SEQ ID NO: 12.

In another preferred embodiment, the CAR has a structure as shown in FIG. 1.

In another preferred embodiment, the L is a signal peptide of a protein selected from the group consisting of: CD8, CD28, GM-CSF, CD4, CD137, or a combination thereof.

In another preferred embodiment, the L is a signal peptide derived from CD8.

In another preferred embodiment, the L has an amino acid sequence as shown in SEQ ID NO: 16 or 1.

In another preferred embodiment, the H is the hinge region of a protein selected from the group consisting of: CD8, CD28, CD137, or a combination thereof. In another preferred embodiment, the H is each independently a hinge region derived from CD8.

In another preferred embodiment, the H has an amino acid sequence as shown in SEQ ID NO: 8.

In another preferred embodiment, the TM is a transmembrane region of a protein selected from the group consisting of: CD28, CD3 epsilon, CD45, CD4, CD5, CD8, CD9, CD16, CD22, CD33, CD37, CD64, CD80, CD86, CD134, CD137, CD154, or a combination thereof. In another preferred embodiment, the TM is each independently a transmembrane region derived from CD8 or CD28. In another preferred embodiment, the CD8-derived transmembrane region has an amino acid sequence as shown in SEQ ID NO: 7.

In another preferred embodiment, the CD28-derived transmembrane region has an amino acid sequence as shown in SEQ ID NO: 6.

In another preferred embodiment, the C is a costimulatory signal molecule of a protein selected from the group consisting of: OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, or a combination thereof. In another preferred embodiment, the C is a costimulatory signal molecule derived from CD28 and/or 4-1BB.

In another preferred embodiment, the 4-1BB-derived costimulatory signal molecule has an amino acid sequence as shown in SEQ ID NO: 5.

In another preferred embodiment, the CD28-derived costimulatory signal molecule has an amino acid sequence as shown in SEQ ID NO: 4.

In another preferred embodiment, the CD3ξ has an amino acid sequence as shown in SEQ ID NO: 3.

In another preferred embodiment, the CAR (preferably C-terminus or N-terminus) further comprises a cell suicide element.

In another preferred embodiment, the cell suicide element is connected to the L or CD3ξ of the CAR or the bispecific CAR via T2A.

In a third aspect of the present invention, a nucleic acid molecule is provided, and the nucleic acid molecule encodes the CAR or TCR according to the first aspect of the present invention or the bispecific CAR or TCR according to the second aspect of the present invention.

In a fourth aspect of the present invention, a vector is provided, and the vector comprises the nucleic acid molecule according to the third aspect of the present invention.

In another preferred embodiment, the vector is selected from the group consisting of: DNAs, RNAs, plasmids, lentiviral vectors, adenoviral vectors, retroviral vectors, transposons, or a combination thereof.

In another preferred embodiment, the vector is a lentiviral vector.

In a fifth aspect of the present invention, a host cell is provided, and the host cell comprises the vector according to the fourth aspect of the present invention, or the nucleic acid molecule according to the third aspect of the present invention exogenously integrated into a chromosome; or expresses the CAR or TCR according to the first aspect of the present invention or the bispecific CAR or TCR according to the second aspect of the present invention.

In a sixth aspect of the present invention, an engineered immune cell is provided, and the immune cell comprises the vector according to the fourth aspect of the present invention, or the nucleic acid molecule according to the third aspect of the present invention exogenously integrated into the a chromosome; or expresses the CAR or TCR according to the first aspect of the present invention or the bispecific CAR or TCR according to the second aspect of the present invention.

In another preferred embodiment, the immune cell has one or more characteristics selected from the group consisting of:
(a) the PD-1 gene expression of the immune cell being silenced;
(b) the immune cell being a T cell, and the TCR gene expression of the T cell being silenced; and
(c) the immune cell expressing an exogenous cell suicide element;
(d) the immune cell expressing or secreting PD-1 antibody, PD-L1 antibody, CD47 antibody, Tim3 antibody, Lag3 antibody, Tigit antibody, OX40 antibody, ICOS antibody, IL7, CXCL19, IL21, TL15, IL2, IL18, or a combination thereof, and
(e) the cytokine-related signaling pathway of the immune cell being enhanced, and the cytokine being selected from the group consisting of: IL7, CXCL19, IL21, IL15, IL2, IL18, or a combination thereof.

In another preferred embodiment, the engineered immune cell is selected from the group consisting of:
(i) a chimeric antigen receptor T cell (CAR-T cell); or
(ii) a chimeric antigen receptor NK cell (CAR-NK cell).

In another preferred embodiment, the immune cell expresses an exogenous cell suicide element.

In another preferred embodiment, the CAR and the cell suicide element are co-expressed in the immune cell.

In another preferred embodiment, the CAR and the cell suicide element are connected by a self-cleaving element.

In another preferred embodiment, the cell suicide element is located at the N-terminus or C-terminus of the CAR.

In another preferred embodiment, the self-cleaving element comprises a 2A sequence or an IRES sequence, preferably: P2A and T2A.

In another preferred embodiment, the cell suicide element is selected from the group consisting of: HSV-TK, iCasp9, ACD20, mTMPK, ACD19, RQR8, EGFRt, or a combination thereof.

In another preferred embodiment, the cell suicide element has a structure as shown in the following formula IV:

$$L2\text{-}D\text{-}F \qquad (IV)$$

in the formula,
"-" is each independently a linker peptide or a peptide bond;
L2 is an optional signal peptide sequence;
D is a suicide switch element; and
F is a transmembrane element.

In another preferred embodiment, the signal peptide is a signal peptide derived from GM-CSFR.

In another preferred embodiment, the cell suicide element is selected from the group consisting of: truncated epidermal growth factor receptor (EGFRt), truncated CD19 (CD19t) gene, induced caspase 9 gene (iCasp9), HSV-TK, ACD20, mTMPK, or a combination thereof.

In another preferred embodiment, the cell suicide element is EGFRt.

In another preferred embodiment, the engineered immune cell is used for autologous immunotherapy and/or allogeneic immunotherapy.

In another preferred embodiment, the engineered immune cell can kill the tumor cells capable of clonal proliferation.

In another preferred embodiment, compared with the immune cell expressing the CAR according to the first aspect of the present invention, the immune cell expressing the bispecific CAR according to the second aspect survives longer in vivo.

In another preferred embodiment, the in vivo includes autologously in vivo or allogeneically in vivo.

In a seventh aspect of the present invention, an engineered immune cell is provided, and the immune cell comprises a first expression cassette and a second expression cassette that are exogenous, wherein the first expression cassette is used to express a first CAR or a first exogenous TCR targeting a first target, and the second expression cassette is used to express a second CAR or a second exogenous TCR targeting BCMA;
or the immune cell expresses the first CAR or the first exogenous TCR targeting the first target and the second CAR or the second exogenous TCR targeting the BCMA,
wherein an antigen binding domain (scFv) targeting the BCMA in the second CAR or the second exogenous TCR comprises an antibody heavy chain variable region as shown in SEQ ID NO: 9 and an antibody light chain variable region as shown in SEQ ID NO: 10; and the first target is selected from the group consisting of: CD138, Kappa Light Chain, NKG2D-ligands, TACI, GPRC5D, CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCRα, TCRβ, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R, TROP-2, or a combination thereof.

In another preferred embodiment, the first target is CD19, and the antigen binding domain (scFv) targeting the CD19 in the first CAR comprises an antibody heavy chain variable region as shown in SEQ ID NO: 11, and an antibody light chain variable region as shown in SEQ ID NO: 12.

In another preferred embodiment, the second CAR is the CAR according to the first aspect of the present invention.

In another preferred embodiment, the first CAR and the second CAR are located on the cell membrane of the immune cell.

In another preferred embodiment, the first CAR targeting the CD19 and the second CAR targeting the BCMA are expressed on the cell membrane of the immune cell.

In another preferred embodiment, the first expression cassette and the second expression cassette are located on the same or different vectors.

In another preferred embodiment, the first expression cassette and the second expression cassette are located on the same vector.

In another preferred embodiment, the first CAR has a structure as shown in the following formula V:

L-scFv1'-H-TM-C-CD3ξ     (V)

in the formula,
"-" is each independently a linker peptide or a peptide bond;
elements L, H, TM, C and CD3ξ are as described above; and
scFv1' is an antigen binding domain targeting CD19.

In another preferred embodiment, the first CAR and the second CAR are connected via a 2A peptide.

In another preferred embodiment, the 2A peptide has a sequence as shown in SEQ ID NO: 2.

In another preferred embodiment, the immune cell further comprises a cell suicide element.

In another preferred embodiment, the cell suicide element and the bispecific CAR are connected (or in tandem) via T2A.

In another preferred embodiment, the cell suicide element is connected to the first CAR and/or the second CAR via T2A.

In another preferred embodiment, the PD1 gene expression of the immune cell is silenced.

In another preferred embodiment, the "PD-1 gene expression being silenced" means that the PD-1 gene is not expressed or is under-expressed.

In another preferred embodiment, the "under-expression" refers to the ratio of the expression level G1 of PD-1 gene of the immune cell to the expression level G0 of PD-1 gene of a normal immune cell (i.e., G1/G0)≤0.5, preferably G1/G0 ≤0.3, more preferably ≤0.2, more preferably ≤0.1, and most preferably 0.

In another preferred embodiment, the "under-expression" refers to the ratio of the expression level G1 of PD-1 gene of the CAR-T cell to the expression level G0 of PD-1 gene of a normal T cell (i.e., G1/G0)≤0.5, preferably G1/G0≤0.3, more preferably ≤0.2, more preferably ≤0.1, and most preferably 0.

In an eighth aspect of the present invention, a formulation is provided, and the formulation comprises the CAR or TCR according to the first or second aspect of the present invention, or the engineered immune cell according to the sixth or seventh aspect of the present invention, and a pharmaceutically acceptable carrier, diluent or excipient.

In another preferred embodiment, the formulation is a liquid formulation.

In another preferred embodiment, the dosage form of the formulation is an injection.

In another preferred embodiment, the engineered immune cell in the formulation has a concentration of $1\times10^3$–$1\times10^8$ cells/ml, preferably $1\times10^4$-$1\times10^7$ cells/ml.

In another preferred embodiment, the CAR comprises a bispecific CAR.

In a ninth aspect of the present invention, use of the CAR or TCR according to the first or second aspect of the present invention, or the engineered immune cell according to the sixth or seventh aspect of the present invention, in the preparation of a drug or a formulation for preventing and/or treating a cancer or a tumor is provided.

In another preferred embodiment, the tumor is a hematological tumor.

In another preferred embodiment, the hematological tumor is selected from the group consisting of: acute myeloid leukemia (AML), multiple myeloma (MM), chronic lymphocytic leukemia (CLL), acute lymphocytic leukemia (ALL), diffuse large B-cell lymphoma (DLBCL), or a combination thereof.

In another preferred embodiment, the cancer or tumor is multiple myeloma.

In another preferred embodiment, the cancer or tumor is lymphoma.

In another preferred embodiment, the lymphoma is selected from the group consisting of: Hodgkin's lymphoma (HL), diffuse large B-cell lymphoma (DLBCL), follicular lymphoma (FL), chronic lymphocytic leukocyte (CLL), small lymphocytic lymphoma (SLL), marginal zone lymphoma (MZL), mantle cell lymphoma (MCL), Burkitt's lymphoma (BL) and complex B-cell non-Hodgkin's lymphoma.

In another preferred embodiment, the cancer or tumor comprises recurrent cancer or tumor.

In another preferred embodiment, the drug or formulation treats the cancer or tumor by killing tumor cells capable of clonal proliferation.

In another preferred embodiment, the tumor cells capable of clonal proliferation comprise clone-forming cells, tumor cell precursor cells, and tumor progenitor cells.

In a tenth aspect of the present invention, a method for preparing an engineered immune cell is provided, and the engineered immune cell expresses the CAR or TCR according to the first or second aspect of the present invention, comprising the following steps: transducing the nucleic acid molecule according to the third aspect of the present invention or the vector according to the fourth aspect of the present invention into an immune cell, thereby obtaining the engineered immune cell.

In another preferred embodiment, the immune cell is a T cell or a NK cell.

In an eleventh aspect of the present invention, a method for preparing an engineered immune cell is provided, comprising the following steps:
(1) providing an immune cell to be engineered; and
(2) introducing a first expression cassette for expressing a first CAR targeting a first target into the immune cell; and
(3) introducing a second expression cassette for expressing a second CAR targeting BCMA into the immune cell, thereby obtaining the engineered immune cell, wherein an antigen binding domain (scFv) targeting the BCMA in the second CAR comprises an antibody heavy chain variable region as shown in SEQ ID NO: 9 and an antibody light chain variable region as shown in SEQ ID NO: 10; and the first target is selected from the group consisting of:

CD138, Kappa Light Chain, NKG2D-ligands, TACI, GPRC5D, CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCRα, TCRβ, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R, TROP-2, or a combination thereof.

In another preferred embodiment, the step (2) can be performed before, after, simultaneously with or alternately with the step (3).

In another preferred embodiment, if the immune cell to be engineered in the step (1) expresses the first CAR or the second CAR, the step (2) or step (3) can be omitted.

In a twelfth aspect of the present invention, a kit is provided, and the kit is used for preparing the engineered immune cell according to the sixth or seventh aspect of the present invention, and the kit comprises a container, and the nucleic acid molecule according to the third aspect of the present invention or the vector according to the fourth aspect of the present invention located in the container.

In a thirteenth aspect of the present invention, a kit is provided, and the kit is used for preparing the engineered immune cell according to the sixth or seventh aspect of the present invention, and the kit comprises a container and the followings located in the container:
(1) a first nucleic acid sequence, the first nucleic acid sequence comprising a first expression cassette, and the first expression cassette is used to express a first CAR targeting a first target; and (2) a second nucleic acid sequence, the second nucleic acid sequence comprising a second expression cassette, and the second expression cassette is used to express the second CAR targeting the BCMA;
wherein an antigen binding domain (scFv) targeting the BCMA in the second CAR comprises an antibody heavy chain variable region as shown in SEQ ID NO: 9 and an antibody light chain variable region as shown in SEQ ID NO: 10; and the first target is selected from the group consisting of:

CD138, Kappa Light Chain, NKG2D-ligands, TACI, GPRC5D, CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCRα, TCRβ, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R, TROP-2, or a combination thereof.

In another preferred embodiment, the first and the second nucleic acid sequences are located in the same or different containers.

In another preferred embodiment, the first and the second nucleic acid sequences are located in the same expression vector.

In a fourteenth aspect of the present invention, use of the engineered immune cell according to the sixth or seventh aspect of the present invention for the prevention and/or treatment of a cancer or a tumor is provided.

In another preferred embodiment, the cancer or tumor is multiple myeloma.

In a fifteenth aspect of the present invention, a method for treating a disease is provided, which comprises administering an appropriate amount of the cell according to the sixth or seventh aspect of the present invention, or the formulation according to the fifth aspect of the present invention, to a subject in need thereof.

In another preferred embodiment, the disease is a cancer or a tumor.

In a sixteenth aspect of the present invention, a method for enhancing the in vivo survival ability of an immune cell or enhancing the killing ability of an immune cell against tumor cells capable of clonal proliferation is provided, comprising (a) expressing both a first expression cassette and a second expression cassette that are exogenous in the immune cell, wherein the first expression cassette is used to express a first CAR targeting CD19, and the second expression cassette is used to express a second CAR targeting BCMA; or (b) expressing the bispecific CAR according to the second aspect in the immune cell.

In another preferred embodiment, the immune cell constructed by the method is as described in the sixth and seventh aspects of the present invention.

In another preferred embodiment, the first expression cassette and the second expression cassette have the same meaning as the first expression cassette and the second expression cassette in the seventh aspect of the present invention.

In another preferred embodiment, the in vivo includes autologously in vivo or allogeneically in vivo.

In a seventeenth aspect of the present invention, a method for enhancing the in vivo survival ability or the killing ability against tumor cells capable of clonal proliferation of an engineered immune cell targeting BCMA is provided, comprising expressing an exogenous first expression cassette in the engineered immune cell, wherein the first expression cassette is used to express a first CAR targeting CD19.

In another preferred embodiment, the first expression cassette has the same meaning as the first expression cassette and the second expression cassette in the seventh aspect of the present invention.

In another preferred embodiment, the engineered immune cell targeting the BCMA is an immune cell expressing the CAR according to the first aspect of the present invention.

In another preferred embodiment, the in vivo includes autologously in vivo or allogeneically in vivo.

In an eighteenth aspect of the present invention, use of a first expression cassette is provided, and the first expression cassette is used to express a first CAR targeting CD19, is used to enhance the in vivo survival ability or the killing ability against tumor cells capable of clonal proliferation of an engineered immune cell targeting BCMA, or is used to prepare a kit, wherein the kit is used to enhance the in vivo survival ability or the killing ability against tumor cells capable of clonal proliferation of an engineered immune cell targeting BCMA.

In another preferred embodiment, the in vivo includes autologously in vivo or allogeneically in vivo.

It should be understood that within the scope of the present invention, each of the above-mentioned technical features of the present invention and each of the various technical features specifically described in the following (such as the embodiments) may be combined with each other to form a new or preferred technical solution. In view of the limited space, they will not be repeated herein.

BRIEF DESCRIPTION OF THE DRAWINGS

FIG. 22 shows the results of in vitro killing experiments (Luciferase method) of CAR-S1 against Raji lymphoma cells, wherein FIG. 22A shows the expression of BCMA antigen on the surface of Raji lymphoma target cells, and FIG. 22B shows the killing of Raji lymphoma target cells by CAR-S1 cells at different E:T ratios.

DETAILED DESCRIPTION OF THE INVENTION

Figure 1:
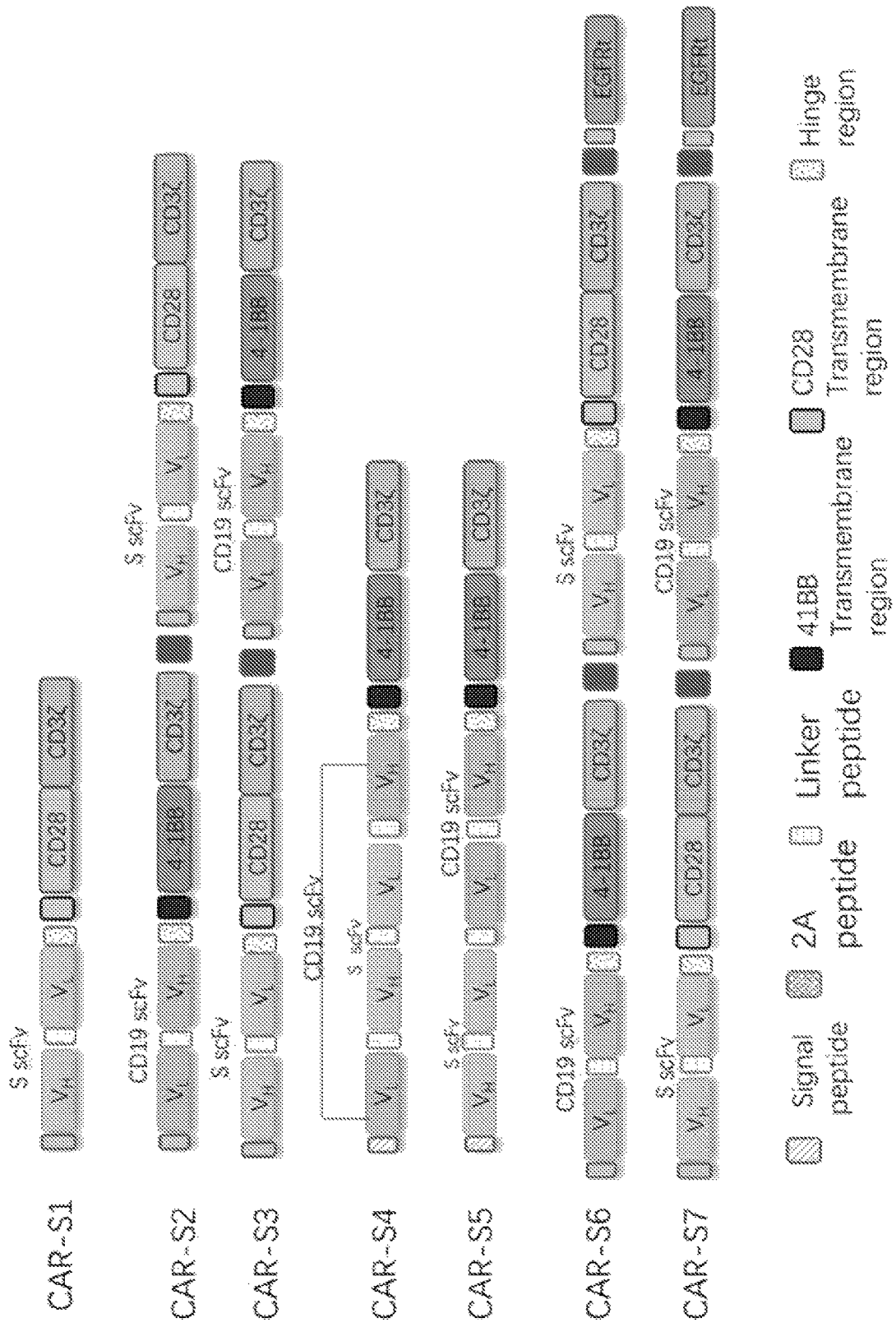
FIG. 1 shows a schematic diagram of a structure containing the CAR and the cell suicide element according to the present invention, wherein the bispecific CAR and the suicide switch element are connected via 2A.

After extensive and in-depth researches, the inventors have constructed a novel engineered immune cell targeting BCMA for the first time, and the antigen binding domain in the CAR contained therein is an S-derived scFv. Experiments have shown that, compared with CAR-T cells constructed by use of BB scFv and April-derived BCMA binding domain, the CAR-T cells constructed in the present invention have higher killing effects and tumor elimination abilities. The present invention also uses S scFv and CD19 scFv to construct dual CAR-T cells, which can kill both BCMA-positive CAR-T cells and CD19-positive CAR-T cells.

Specifically, the CAR-T cells of the present invention are constructed by use of scFvs of different BCMA antibodies. By comparing them, it is unexpectedly found that the CAR-T cells constructed by the S-derived scFvs have higher ability of killing BCMA-overexpressing cells and BCMA-positive tumor target cells than those constructed by the BB scFvs and the April-derived BCMA binding domain. In vivo mouse animal models also show that it has higher tumor elimination abilities than BB-derived CAR-T. CAR-T cells constructed with some other scFvs targeting BCMA commonly used in the art show no ideal in vitro and in vivo functions.

Terms

In order to better understand the present disclosure, certain terms are firstly defined. As used in the present application, unless expressly stated otherwise herein, each of the following terms shall have the meanings given below. Other definitions are set forth throughout the application.

The term "about" may refer to a value or composition within an acceptable error range of a particular value or composition determined by a person of ordinary skill in the art, which will depend in part on how the value or composition is measured or determined.

The term "administration" refers to the use of any of various methods and delivery systems known to those skilled in the art to physically introduce the product of the present invention into a subject, including intravenous, intramuscular, subcutaneous, intraperitoneal, intraspinal or other parenteral routes of administration, such as via injection or infusion.

The term "antibody" (Ab) shall include, but is not limited to, immunoglobulins, which specifically bind to antigens and comprise at least two heavy (H) chains and two light (L) chains interconnected by disulfide bonds, or antigen binding portions thereof. Each H chain contains a heavy chain variable region (abbreviated as VH herein) and a heavy chain constant region. The heavy chain constant region contains three constant domains CH1, CH2 and CH3. Each light chain contains a light chain variable region (abbreviated as VL herein) and a light chain constant region. The light chain constant region contains a constant domain CL. The VH and VL regions can be further subdivided into hypervariable regions called complementarity determining regions (CDRs), which are interspersed with more conservative regions called framework regions (FRs). Each VH and VL contains three CDRs and four FRs, arranged in the following order from the amino terminus to the carboxyl terminus: FR1, CDR1, FR2, CDR2, FR3, CDR3, and FR4. The variable regions of the heavy and light chains contain binding domains that interact with antigens.

It should be understood that the amino acid names herein are identified by internationally accepted single English letters, and the corresponding three-letter abbreviations of amino acid names are: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V), respectively.

B Cell Maturation Antigen (BCMA)

BCMA is a transmembrane protein expressed on the surface of mature B lymphocytes, i.e. the surface of plasmablasts and plasma cells. Multiple myeloma is caused by the abnormal proliferation of plasma cells and invasion into the bone marrow. Studies have shown that BCMA is expressed on multiple myeloma cells. Car-T cells targeting BCMA have been shown to specifically kill myeloma cells. However, after some patients receive CAR-T cell therapy targeting BCMA, there will still be a course of relapse. For these relapsed patients, it is necessary to find another target that is different from BCMA in order to continue the treatment.

CD19

CD19 molecule is a transmembrane protein on the surface of B cells, which is closely related to B cell activation, signal transduction and growth regulation. As shown in FIG. 1, CD19 is almost expressed on the surface of all B cells, and the CAR-T cells targeting CD19 currently have significant efficacy in the treatment of leukemia and lymphoma. It is generally believed that 99.95% of plasma cells do not express CD19 on the surface, thus the possibility of using CD19 for the treatment of multiple myeloma is ignored.

Chimeric Antigen Receptors (CARs)

The chimeric antigen receptors (CARs) of the present invention comprise an extracellular domain, a transmembrane domain, and an intracellular domain. The extracellular domain comprises target-specific binding elements (also referred to as antigen binding domains). The intracellular domain comprises a costimulatory signaling region and a (chain portion. The costimulatory signaling region refers to a portion of the intracellular domain that comprises costimulatory molecules. Co-stimulatory molecules are cell surface molecules required for effective response of lymphocytes to antigens, and are not antigen receptors or their ligands.

Between the extracellular domain and the transmembrane domain of the CARs, or between the cytoplasmic domain and the transmembrane domain of the CARs, a linker can be incorporated. As used herein, the term "linker" generally refers to any oligopeptide or polypeptide that functions to connect the transmembrane domain to the extracellular domain or cytoplasmic domain of a polypeptide chain. The linker may comprise 0 to 300 amino acids, preferably 2 to 100 amino acids and most preferably 3 to 50 amino acids.

In a preferred embodiment of the present invention, the extracellular domain of the CAR provided by the present invention comprises an antigen binding domain targeting BCMA (or BCMA and CD19). When the CAR of the present invention is expressed in T cells, it can perform antigen recognition based on the antigen binding specificity. When it binds to its associated antigen, it affects tumor cells, causing the tumor cells to stop growing, be promoted to die or otherwise be affected, and causing reduced or eliminated tumor burden in patients. The antigen binding domain is preferably fused to an intracellular domain from one or more of the costimulatory molecule and the (chain. Preferably, the antigen binding domain is fused to a 4-1BB signaling domain, and an intracellular domain combined with a CD3ξ signaling domain.

As used herein, the "antigen binding domain" and the "single-chain antibody fragment" both refer to a Fab fragment, a Fab' fragment, a F(ab')$_2$ fragment, or a single Fv fragment having antigen binding activity. The Fv antibody contains an antibody heavy chain variable region and an antibody light chain variable region, but has no constant region, and is the smallest antibody fragment having all antigen binding sites. Generally, the Fv antibody also contains a polypeptide linker between the VH and VL domains, and can form a structure required for the antigen binding. The antigen binding domain is usually scFv (single-chain variable fragment). The size of scFv is generally ⅙ of that of a complete antibody. The single-chain antibody is preferably an amino acid chain sequence encoded by a nucleotide chain. As a preferred embodiment of the present invention, the antigen binding domain comprises an antibody that specifically recognizes BCMA, and optionally, the antigen binding domain further comprises an antibody (preferably a single-chain antibody) that specifically recognizes CD19.

For the hinge region and the transmembrane region (transmembrane domain), the CAR can be designed to comprise a transmembrane domain fused to the extracellular domain of the CAR. In one embodiment, a transmembrane domain that is naturally associated with one of the domains in the CAR is used. In some examples, the transmembrane domain can be selected or modified by amino acid substitutions to avoid binding such domains to transmembrane domains of the same or a different surface membrane protein, thereby minimizing the interaction with the other members of the receptor complex.

The intracellular domain in the CAR of the present invention comprises the signaling domain of 4-1BB and the signaling domain of CD3ξ.

Preferably, the CAR of the present invention also comprises a cell suicide element.

Preferably, the scFv targeting BCMA of the present invention is S scFv, and the BB scFv and April chain in the examples are used as controls. Both BB scFv and April chain are commonly used binding sequences in the art for targeting BCMA, BB scFv has been described in PCT application WO 2010104949 A3, and April chain has been described in CN105658671A.

Bispecific CAR Targeting CD19 and BCMA

Multiple myeloma (MM) is a malignant plasma cell tumor. The tumor cells originate from plasma cells in the bone marrow, and plasma cells are cells that develop by B lymphocytes in the final functional stage. Multiple myeloma is basically an incurable disease with the characteristics of high morbidity and high mortality. In 2017's statistics, there were 30,000 newly diagnosed multiple myeloma patients in the United States, among them, 12,000 might face death. At present, common therapies for multiple myeloma include cytotoxic drug therapy, protease inhibitors (bortezomib, etc.), lenalidomide, monoclonal antibodies, corticosteroids, and the like. However, the current therapies are all partially effective, have no lasting alleviation effect, and have high risk of recurrence. Therefore, the improvement in the therapies of multiple myeloma appears to be particularly important.

CD19 is a glycoprotein with a molecular weight of 95 kDa, expressed on the membrane surface of pre-B cells and mature B cells, is closely related to the transmembrane signaling pathway of B cell Ca++, and has a regulatory effect on the proliferation and differentiation of B cells. CD19 is mainly expressed in normal B cells and cancerous B cells, with high tissue expression specificity, and is a good target for antibody or CAR-T immunotherapy. However, in the course of immunotherapy, the CD19 epitope of B cells is often lost, causing failure to respond to the immunotherapy or relapse in patients.

Bispecificity means that the same CAR can specifically bind to and immunologically recognize two different antigens, and the CAR can produce an immune response when combined with any one of the antigens.

In another preferred embodiment, the bispecific CAR targeting CD19 and BCMA is as described in the second aspect of the present invention.

In a preferred embodiment of the present invention, the extracellular domain of CAR provided by the present invention comprises antigen binding domains targeting CD19 and BCMA, comprising anti-CD19 scFv and anti-BCMA scFv.

In another preferred embodiment, the present invention provides a bispecific chimeric antigen receptor directing to CD19 and BCMA antigens. The CAR structural components targeting both CD19 and BCMA can comprise a signal peptide, an anti-CD19 scFv, an anti-BCMA scFv, a hinge region, a transmembrane region, and an intracellular T cell signaling region, where CD19scFv and BCMAscFv are connected through a short peptide segment (G4S)×N (SEQ ID NO: 40). The CAR structure targeting both CD19 and BCMA is as described in the second aspect of the present invention.

In another preferred embodiment, the CD19- and BCMA-bispecific CAR of the present invention has a single structure and contains scFvs against CD19 and BCMA, wherein the CAR contains CD19 scFv and BCMA scFv, and the ordering of CD19 scFv and BCMA scFv and the hinge are the main influence factors of its functions.

In another preferred embodiment, the present invention optimizes the sequence of BCMA scFv. The BCMA scFv (S scFv) has high affinity and good specificity with BCMA, and can specifically target the full-length antigen and extracellular region of BCMA.

In a preferred embodiment of the present invention, (G4S)×3 (SEQ ID NO: 17) is used to connect CD19scFv and BCMAScFv. This CAR has the best activity and killing ability.

The bispecific CARs targeting CD19 and BCMA are used in the present invention. Compared with CARs targeting a single antigen, the affinity thereof is significantly enhanced, the activity of immune cells is significantly increased, and a synergistic effect is obtained. In addition, due to the uneven expression levels of CD19 and BCMA in tumor cells, the dual-targeted CAR-T has a wider therapeutic range. The CAR-immune cells targeting both CD19 and BCMA can reduce the possibility of antigen escape caused by the down-regulation or deficiency of a single surface antigen. In addition, the bispecific CAR-T of CD19 and BCMA has an ability of inhibiting the in vitro clone formation of CD34-negative monocytes in the bone marrow of patients with myeloma that is significantly better than that of a single CAR-T, indicating that it has an ability of inhibiting tumor progenitor cells that is significantly better than that of a single CAR-T. Finally, the addition of CD19 antigen can increase the continuous survival ability of the bispecific CAR-T of CD19 and BCMA.

Chimeric Antigen Receptor T Cells (CAR-T Cells)

As used herein, the terms "CAR-T cells", "CAR-T" and "CAR-T cells of the present invention" comprise the CAR-T cells included in the third aspect of the present invention.

CAR-T cells have the following advantages over other T cell-based therapies: (1) the action process of CAR-T cells is not restricted by MHC; (2) in view of the fact that many tumor cells express the same tumor antigen, once the construction of the CAR genes directing at a certain antigen is completed, it can be widely used; (3) CAR can use both tumor protein antigens and glycolipid non-protein antigens, expanding the range of tumor antigen targets; (4) the risk of rejection can be reduced by using autologous cells of patients; and (5) CAR-T cells have immunological memory function and can survive in the body for a long time.

Chimeric Antigen Receptor NK Cells (CAR-NK Cells)

As used herein, the terms "CAR-NK cells", "CAR-NK" and "CAR-NK cells of the present invention" all refer to the CAR-NK cells included in the third aspect of the present invention. The CAR-NK cells of the present invention can be used to treat tumors with high BCMA expression, such as multiple myeloma.

Natural killer (NK) cells are a major type of immune effector cells that protect the body from virus infection and tumor cell invasion through a non-antigen-specific pathway. The engineered (genetically modified) NK cells may acquire new functions, including the ability to specifically recognize tumor antigens and enhanced anti-tumor cytotoxicity.

Compared with autologous CAR-T cells, CAR-NK cells further have the following advantages of, for example, (1) killing tumor cells directly by releasing perforin and granzyme, without having a killing effect on normal cells in the body; (2) releasing a small amount of cytokines, thereby reducing the risk of cytokine storm; and (3) expanding and developing very easily in vitro into "off-the-shelf" products. In addition, it is similar to CAR-T cell therapy.

Suicide Gene Switch

In order to further control the adverse reactions of CAR-T cells such as non-tumor targeting and cytokine release syndrome, the CAR-T cells in the present invention all have a suicide gene switch, which can effectively eliminate CAR-T cells in the body under the action of an exogenous drug, thereby blocking unknown or uncontrollable long-term toxicity to ensure patients' safety.

The suicide switch used in the present invention can be the herpes simplex virus thymidine kinase (HSV-TK), inducible caspase 9 (iCasp9), CD20, mutated human thymidylate kinase (mTMPK), etc. In comparison, HSV-TK, iCasp9 and CD20 have the same elimination ability on CAR-cells, but iCasp9 and CD20 have faster elimination speed, and HSV-TK has slower elimination speed.

The iCasp9 suicide switch comprises an FKBP12-F36V domain, which can be connected to caspase 9 that contains no recruitment domain via a flexible linker. FKBP12-F36V comprises an FKBP domain with phenylalanine substituted for valine at the $36^{th}$ amino acid residue position. It has high selectivity and sub-nanomolar affinity, and can bind a dimerizing ligand, such as other inert small molecules AP1903. The small molecule can promote its dimerization when added, thereby inducing cell apoptosis, but the small molecule is not effective for normal cells that do not carry a suicide switch.

The inducible safety switch caspase9 (iCasp9) uses human caspase9 fused to FK506 binding protein (FKBP), which can be induced to form a dimer with a chemical inducer (AP1903/Rimiducid, Bellicum Pharmaceutical), leading to apoptosis of cells expressing the fusion protein.

Although CD19 and BCMA are highly expressed in tumor cells, they are also expressed in normal B cells. Therefore, the engineered immune cells of the present invention can attack normal B cells in vivo.

How to control the safety of CAR-cells has always been an urgent problem to be solved. Adding a safety switch to CAR-cells is the safest way to terminate the activity of CAR-cells. After CAR-cells produce severe toxicity (CRS/ neurotoxicity) or after the patient reaches long-term sustained remission, the inducible iCasp9 safety switch will control the elimination of the CAR-cells.

Vector

The nucleic acid sequence encoding the desired molecule can be obtained using recombinant methods known in the art, such as, for example, by screening a library from cells expressing the gene, by obtaining the gene from a vector known to comprise the gene, or by using a standard technology to separate directly from the cells and tissues that comprise the gene. Optionally, the gene of interest can be produced synthetically.

The present invention also provides a vector into which an expression cassette of the present invention is inserted. A vector derived from a retrovirus such as lentivirus is a suitable tool to achieve long-term gene transfer because it allows the long-term, stable integration of the transgene and propagation of the transgene in daughter cells. Lentiviral vectors have advantages over vectors derived from an oncogenic retrovirus such as murine leukemia virus, because they can transduce non-proliferating cells, such as hepatocytes. They also have the advantage of low immunogenicity.

In general, the expression cassette or nucleic acid sequence of the present invention is usually operably connected to a promoter and incorporated into an expression vector. This vector is suitable for replication and integration in eukaryotes. A typical cloning vector contains transcription and translation terminator, initial sequence and promoter that can be used to regulate the expression of the desired nucleic acid sequence.

The expression construct of the present invention can also utilize standard gene delivery protocols for nucleic acid immunization and gene therapy. The method of gene delivery is known in the art. See, for example, U.S. Pat. Nos. 5,399,346, 5,580,859, 5,589,466, which are incorporated herein by reference in their entireties. In another embodiment, the present invention provides a gene therapy vector.

The nucleic acid can be cloned into many types of vectors. For example, the nucleic acid can be cloned into such a vector, which includes but is not limited to a plasmid, a phagemid, a phage derivative, an animal virus and a cosmid. Specific vectors of interest include an expression vector, a replication vector, a probe generation vector, and a sequencing vector.

Further, the expression vector can be provided to the cell in the form of a viral vector. A viral vector technology is well known in the art and is described in, for example, Sambrook et al. (2001, Molecular Cloning: A Laboratory Manual, Cold Spring Harbor Laboratory, New York) and other handbooks of virology and molecular biology. Virus that can be used as a vector includes, but is not limited to, retrovirus, adenovirus, adeno-associated virus, herpes virus, and lentivirus. Generally, a suitable vector contains a replication origin, a promoter sequence, a convenient restriction site and one or more selectable markers that function in at least one organism (see e.g. WO01/96584; WO01/29058; and U.S. Pat. No. 6,326,193).

Many virus-based systems have been developed for gene transfer into mammalian cells. For example, a retrovirus provides a convenient platform for gene delivery systems. The selected gene can be inserted into the vector and packaged into retroviral particles using techniques known in the art. The recombinant virus can then be isolated and delivered to the target cells in vivo or ex vivo. Many retroviral systems are known in the art. In some embodiments, adenovirus vectors are used. Many adenovirus vectors are known in the art. In one embodiment, lentiviral vectors are used.

Additional promoter elements, such as enhancers, can regulate the frequency at which the transcription begins. Generally, these elements are located in a 30-110 bp region upstream of the initiation site, although it has recently been shown that many promoters also comprise functional elements downstream of the initiation site. The spacing between the promoter elements is often flexible in order to maintain the function of the promoter when the elements are inverted or moved relative to one another. In the thymidine kinase (tk) promoter, the spacing between the promoter elements can be increased by 50 bp before the activity begins to decrease. Depending on the promoter, it appears that individual elements can act cooperatively or independently to initiate the transcription.

An example of a suitable promoter is the immediate-early cytomegalovirus (CMV) promoter sequence. This promoter sequence is a strong constitutive promoter sequence capable of driving high-level expression of any polynucleotide sequence operably linked thereto. Another example of a suitable promoter is elongation growth factor-1α (EF-1α). However, other constitutive promoter sequences can also be used, including but not limited to simian virus 40 (SV40) early promoter, mouse mammary tumor virus (MMTV), human immunodeficiency virus (HIV) long terminal repeat (LTR) promoter, MoMuLV promoter, avian leukemia virus promoter, Epstein-Barr virus immediate-early promoter, Rous sarcoma virus promoter, and human gene promoters, such as but not limited to actin promoter, myosin promoter, heme promoter and creatine kinase promoter. Further, the present invention should not be limited to the use of the constitutive promoters. Inducible promoters are also contemplated as part of the present invention. The use of an inducible promoter provides a molecular switch that can turn on the expression of a polynucleotide sequence operably linked to the inducible promoter when such expression is desired, or turn off the expression when it is undesired. Examples of the inducible promoters include, but are not limited to, a metallothionein promoter, a glucocorticoid promoter, a progesterone promoter and a tetracycline promoter.

In order to evaluate the expression of the CAR polypeptide or portion thereof, the expression vector introduced into the cell may also comprise either or both of selectable marker gene and reporter gene, so as to facilitate the identification and selection of the expressing cells from the cell population sought to be transfected or infected by the viral vector. In other aspects, the selectable marker can be carried on a single fragment of DNA and used in the co-transfection procedure. Both the selectable marker and the reporter gene can be flanked by appropriate regulatory sequences so that they can be expressed in the host cells. Useful selectable marker includes, for example, an antibiotic resistance gene, such as neo, and the like.

The reporter gene is used to identify a potentially transfected cell and to evaluate the functionality of the regulatory sequences. Generally, the reporter gene is a gene that is not present in the recipient organism or tissue or expressed by the recipient organism or tissue, and it encodes a polypeptide whose expression can be clearly indicated by some easily detectable properties such as enzyme activity. After the DNA has been introduced into the recipient cell, the expression of the reporter gene is measured at an appropriate time. Suitable reporter genes may include genes encoding luciferase, β-galactosidase, chloramphenicol acetyltransferase, secreted alkaline phosphatase or green fluorescent protein (e.g. Ui-Tei et al., 2000 FEBS Letters 479:79-82). Suitable expression systems are well known and can be prepared using known techniques or commercially available. Generally, a construct with a minimum of 5 flanking regions that shows the highest level of reporter gene expression is identified as a promoter. Such a promoter region can be connected to a reporter gene and used to evaluate the ability of a reagent to regulate the promoter-driven transcription.

Methods of introducing genes into cells and expressing genes into cells are known in the art. In the context of the expression vector, the vector can be easily introduced into host cells, for example, mammalian, bacterial, yeast or insect cells, by any method in the art. For example, the expression vector can be transferred into the host cells by physical, chemical or biological means.

Physical methods for introducing polynucleotides into host cells include calcium phosphate precipitation, lipofection, particle bombardment, microinjection, electroporation, and the like. Methods of producing cells that comprise vectors and/or exogenous nucleic acids are well known in the art. See, for example, Sambrook et al. (2001, Molecular Cloning: A Laboratory Manual, Cold Spring Harbor Laboratory, New York). The preferred method of introducing polynucleotides into host cells is calcium phosphate transfection.

Biological methods for introducing polynucleotides of interest into host cells comprise the use of DNA and RNA vectors. Viral vectors, especially retroviral vectors, have become the most widely used method of inserting genes into mammalian cells such as human cells. Other viral vectors can be derived from lentivirus, poxvirus, herpes simplex virus I, adenovirus and adeno-associated virus, etc. See, for example, U.S. Pat. Nos. 5,350,674 and 5,585,362.

Chemical means for introducing polynucleotides into host cells comprise a colloidal dispersion system, such as a macromolecular complex, a nanocapsule, a microsphere, a bead; and a lipid-based system, comprising oil-in-water emulsion, micelle, mixed micelle and liposome. Exemplary colloidal system used as a delivery vehicle in vitro and in vivo is a liposome (e.g. an artificial membrane vesicle).

In the case of using a non-viral delivery system, an exemplary delivery tool is a liposome. Use of a lipid formulation is considered to introduce nucleic acids into host cells (in vitro, ex vivo, or in vivo). On the other hand, this nucleic acid can be associated with the lipid. Lipid-associated nucleic acids can be encapsulated in the aqueous interior of a liposome, dispersed in the lipid bilayer of a liposome, attached to a liposome via a linking molecule associated with both the liposome and the oligonucleotide, trapped into a liposome, complexed with a liposome, dispersed in a solution containing the lipid, mixed with the lipid, combined with the lipid, contained in the lipid as a suspension, contained in micelles or complexed with micelles, or otherwise associated with the lipid. The lipid, lipid/DNA or lipid/expression vector associated with the composition is not limited to any specific structure in the solution. For example, they can exist in a bilayer structure, as micelles or have a "collapsed" structure. They can also be simply dispersed in the solution, possibly forming aggregates of uneven size or shape. Lipids are fatty substances, which can be naturally occurring or synthetic lipids. For example, lipids comprise fat droplets, which naturally occur in the cytoplasm and in such compounds containing long-chain aliphatic hydrocarbons and their derivatives such as fatty acids, alcohols, amines, amino alcohols and aldehydes.

In a preferred embodiment of the present invention, the vector is a lentiviral vector.

Formulation

The present invention provides a formulation comprising CAR-T cells according to the first aspect of the present invention, and a pharmaceutically acceptable carrier, diluent or excipient. In one embodiment, the formulation is a liquid formulation. Preferably, the formulation is an injection.

Preferably, the concentration of the CAR-T cells in the formulation is $1\times10^3$-$1\times10^8$ cells/ml, more preferably $1\times10^4$-$1\times10^7$ cells/ml.

In one embodiment, the formulation may comprise a buffer such as neutral buffer saline, sulfate buffer saline, and the like; a carbohydrate such as glucose, mannose, sucrose or dextran, mannitol; a protein; a polypeptide or an amino acid such as glycine; an antioxidant; a chelating agent such as EDTA or glutathione; an adjuvant (e.g. aluminum hydroxide); and a preservative. The formulation of the invention is preferably formulated for intravenous administration.

Therapeutic Application

The present invention comprises a therapeutic application with cells (e.g. T cells) transduced with a lentiviral vector (LV) encoding the expression cassette of the present invention. The transduced T cells can target the markers BCMA and/or CD19 of tumor cells, and synergistically activate T cells, causing T cell immune response, thereby significantly improving their killing efficiency on tumor cells.

Therefore, the present invention also provides a method for stimulating a T cell-mediated immune response to a target cell population or tissue in mammalians, which comprises the following step: administering the CAR-T cells of the present invention to a mammal.

In one embodiment, the present invention comprises a type of cell therapy in which a patient's autologous T cells (or from allogeneic donors) are isolated, activated and genetically modified to produce CAR-T cells, and then injected into the same patient. In this way, the probability of suffering from transplant-versus-host disease is extremely low, and the antigen is recognized by T cells in a non-MHC-restricted manner. In addition, one CAR-T can treat all cancers that express the antigen. Unlike antibody therapies, CAR-T cells can replicate in vivo, producing long-term persistence that can lead to sustained tumor control.

In one embodiment, the CAR-T cells of the present invention can undergo stable in vivo T cell expansion and last for an extended amount of time. In addition, the CAR-mediated immune response can be part of an adoptive immunotherapy procedure, in which CAR-modified T cells induce an immune response specific to the antigen binding domain in the CAR. For example, CAR-T cells against BCMA and/or CD19 elicit a specific immune response against cells that express BCMA and/or CD19.

Although the data disclosed herein specifically disclose a lentiviral vector comprising anti-BCMA and/or CD19 scFv, hinge and transmembrane regions, and 4-1BB/CD28 and CD3ξ signaling domains, the present invention should be construed as comprising any changes in number of each of the construct components.

Treatable cancers include tumors that have not been vascularized or have not been substantially vascularized, as well as vascularized tumors. The cancer can include a non-solid tumor (such as a hematological tumor, e.g. leukemia and lymphoma) or can include a solid tumor. The types of cancer treated with the CARs of the present invention include, but are not limited to, carcinoma, blastoma and sarcoma, and certain leukemia or lymphoid malignancies, benign and malignant tumors, and malignancies such as sarcoma, carcinoma and melanoma. Adult tumors/cancers and pediatric tumors/cancers are also included.

Hematological cancer is a cancer of the blood or bone marrow. Examples of a hematological (or hematogenic) cancer include leukemia, including acute leukemia (such as acute lymphocytic leukemia, acute myeloid leukemia, acute myelogenous leukemia and myeloblastic leukemia, promyelocytic leukemia, granulomonocytic leukemia, monocytic leukemia and erythroleukemia), chronic leukemia (such as chronic myeloid (granulocytic) leukemia, chronic myelogenous leukemia and chronic lymphoid leukaemia), polycythemia vera, lymphoma, Hodgkin's disease, non-Hodgkin's lymphoma (painless and advanced form), multiple myeloma, Waldenstrom's macroglobulinemia, heavy chain disease, myelodysplastic syndrome, hairy cell leukemia and myelodysplasia.

A solid tumor is an abnormal lump of tissue that does not usually comprise a cyst or fluid area. A solid tumor can be benign or malignant. Different types of solid tumors are named after the cell types of which they are formed (such as sarcoma, carcinoma, and lymphoma). Examples of solid tumor such as sarcoma and carcinoma include fibrosarcoma, myxosarcoma, liposarcoma, mesothelioma, lymphoid malignancies, pancreatic cancer, and ovarian cancer.

The CAR-modified T cells of the present invention can also be used as a type of vaccine for ex vivo immunization and/or in vivo therapy of a mammal. Preferably, the mammal is a human.

For ex vivo immunization, at least one of the following occurs in vitro before administering the cells into the mammal: i) expanding the cells, ii) introducing the CAR-encoding nucleic acids into the cells, and/or iii) cryopreserving the cells.

The ex vivo procedures are well known in the art and are discussed more fully below. Briefly, the cells are isolated from a mammal (preferably a human) and genetically modified (i.e. transduced or transfected in vitro) with a vector expressing the CAR disclosed herein. CAR-modified cells can be administered to a mammalian recipient to provide therapeutic benefits. The mammalian recipient can be a human, and the CAR-modified cell can be autologous relative to the recipient. Alternatively, the cell can be allogeneic, syngeneic or xenogeneic relative to the recipient.

In addition to using cell-based vaccines for ex vivo immunization, the present invention also provides a composition and a method for in vivo immunization to elicit an immune response against an antigen in a patient.

The present invention provides a method for treating a tumor, which comprises administering a therapeutically effective amount of CAR-modified T cells of the present invention to a subject in need thereof.

The CAR-modified T cells of the present invention can be administered alone or as a pharmaceutical composition in combination with a diluent and/or other component such as IL-2, IL-17 or other cytokines or cell populations. Briefly, the pharmaceutical composition of the present invention may comprise the target cell population as described herein, combined with one or more pharmaceutically or physiologically acceptable carriers, diluents or excipients. Such a composition may comprise a buffer such as neutral buffer saline, sulfate buffer saline, and the like; a carbohydrate such as glucose, mannose, sucrose or dextran, mannitol; a protein; a polypeptide or an amino acid such as glycine; an antioxidant; a chelating agent such as EDTA or glutathione; an adjuvant (e.g. aluminum hydroxide); and a preservative. The composition of the invention is preferably formulated for intravenous administration.

The pharmaceutical composition of the present invention can be administered in a manner suitable for the disease to be treated (or prevented). The quantity and frequency of administration will be determined by factors such as the patient's disorders, and the type and severity of the patient's diseases, although the appropriate dosage can be determined by clinical trials.

When referring to "immunologically effective amount", "anti-tumor effective amount", "tumor-suppressive effective amount" or "therapeutic amount", the precise amount of the composition of the present invention to be administered can be determined by a physician, who considers the individual differences in a patient's (subject's) age, weight, tumor size, degree of infection or metastasis, and the disorders. It may generally be pointed out that the pharmaceutical composition comprising the T cells described herein can be administered at a dose of $10^4$ to $10^9$ cells/kg body weight, preferably at a dose of $10^5$ to $10^6$ cells/kg body weight (including all integer values within those ranges). The T cell composition can also be administered multiple times at these doses. Cells can be administered by using well-known injection techniques in immunotherapy (see, for example, Rosenberg et al., New Eng. J. of Med. 319:1676, 1988). The optimal dosage and therapeutic regimen for a specific patient can be easily determined by those skilled in the medical field through monitoring the patient's signs of disease and adjusting the therapy accordingly.

The administration of the composition to a subject can be carried out in any convenient way, including by spraying, injection, deglutition, infusion, implantation or transplantation. The compositions described herein can be administered to a patient by subcutaneous, intracutaneous, intratumoral, intranodal, intraspinal, intramuscular, intravenous (i.v.) injection or intraperitoneally. In one embodiment, the T cell composition of the present invention is administered to the patient by intracutaneous or subcutaneous injection. In another embodiment, the T cell composition of the present invention is preferably administered by i.v. injection. The composition of T cells can be injected directly into tumors, lymph nodes or infection sites.

In certain embodiments of the present invention, the cells activated and expanded using the methods described herein or other methods known in the art to expand the T cells to a therapeutic level are administered to a patient in combination with (e.g. prior to, coinstantaneous with or subsequent to) any number of relevant therapeutic forms, and the therapeutic forms include but are not limited to therapies with the following reagents: the reagents such as antiviral therapy, cidofovir and interleukin-2, cytarabine (also known as ARA-C), or natalizumab therapy for MS patients, or efalizumab therapy for psoriasis patients, or other therapies for PML patients. In further embodiments, the T cells of the present invention can be used in combination with the followings: chemotherapy, radiation, an immunosuppressive agent such as cyclosporine, azathioprine, methotrexate, mycophenolate mofetil and FK506, an antibody or other immunotherapeutic agents. In further embodiments, the cell composition of the present invention is administered to a patient in combination with (e.g. prior to, coinstantaneous with or subsequent to) bone marrow transplantation, using a chemotherapeutic agent such as fludarabine, external beam radiotherapy (XRT), and cyclophosphamide. For example, in one embodiment, the subject can undergo a standard treatment of high-dose chemotherapy followed by peripheral blood stem cell transplantation. In some embodiments, after transplantation, the subject receives an infusion of the expanded immune cells of the present invention. In an additional embodiment, the expanded cells are administered before or after surgery.

The dosage of the above treatment administered to the patient will vary with the precise nature of the disorder being treated and the recipient being treated. The dosage ratio administered to a human can be implemented according to the practice accepted in the art. Generally, $1\times10^6$ to $1\times10^{10}$ of the modified T cells (e.g. CAR-T20 cells) of the present invention can be administered to the patient per treatment or per course of treatment, for example, by intravenous reinfusion.

The Main Advantages of the Present Invention Include:
(a) The CAR-T cells comprising S scFv constructed according to the present invention have higher in vivo and in vitro tumor killing and functional activities than BB and April CAR-Ts.
(b) The bispecific CAR-T constructed according to the present invention can recognize two or more targets, including BCMA.

The present invention will be further described in conjunction with specific examples below. It should be understood that these examples are only used to describe the present invention but not to limit the scope of the present invention. The experimental methods without indicating specific conditions in the following examples are usually in accordance with conventional conditions, or in accordance with the conditions recommended by the manufacturer. Unless otherwise stated, percentages and parts are calculated by weight.

Example 1 Isolation of PBMC from Donor Blood and Expansion of T Cells

The mononuclear cells were isolated from donor blood, then density gradient centrifugation was performed with Histopaque-1077 (Sigma-Aldrich), and the T cells (EasySep Human T Cell Enrichment Kit, Stemcell Technologies) were enriched. The T cells were activated, cultured and expanded using coupled anti-CD3/anti-CD28 magnetic beads; X-vivol5 (300 IU/ml rhIL2) was used as the medium; and then all cells were cultured in a constant temperature incubator at 37° C., 5% $CO_2$.

Example 2 Cell Culture and Construction

BCMA-expressing cell lines MM.1s and RPMI8226, MM.1s-ffluc cells, RPMI8226-ffluc cells, and Hela cells expressing BCMA, CD19 or both BCMA and CD19, were all cultured in RPMI 1640 medium; and 293T (Human renal epithelial cell line cells, ATCC® CRL-3216) were cultured with DMEM medium. All media were supplemented with 10% (v/v) fetal bovine serum, 100 U/ml penicillin and streptomycin, 2 mM L-glutamine, and 1 mM sodium pyruvate.

Among them, the Hela cells expressing BCMA, CD19 or both BCMA and CD19 were stably transfected cell lines obtained by transferring BCMA and/or CD19 antigens through a lentiviral vector, and can specifically express BCMA or/and CD19 protein molecules. MM.1s-ffluc cells and RPMI8226-ffluc cells were stably transfected cell lines obtained by screening after infection with firefly luciferase lentivirus.

Example 3 Structure Design and Transduction of CAR

A single CAR targeting BCMA and a dual CAR targeting both BCMA and CD19 were designed and constructed and the structural schematic diagrams were as shown in FIG. 1. Among them, CAR, CD19 CAR and suicide switch-EGFRt element were connected via a 2A peptide. Specifically, the CAR structure involved in the present invention was shown in FIG. 1, and the naming and composition were shown in Table 1.

Table 1 The structure of CAR

TABLE 1

| Structure Naming | Structure Composition | CAR-T Name |
|---|---|---|
| S1 | Single S scFv | CAR-S1 |
| S2 | Parallel CD19 CAR + S CAR (dual CAR) | CAR-S2 |
| S3 | Parallel S CAR + CD19 CAR (dual CAR) | CAR-S3 |
| S4 | Loop structured CD19 scFv + S scFv | CAR-S4 |
| S5 | Tandem CD19 scFv + S scFv | CAR-S5 |
| BB | Single BB scFv | CAR-BB |
| April | Single April chain | CAR-April |
| 19 | Single CD19 scFv | CAR-19 |
| S6 | Parallel CD19 CAR + S CAR + EGFRt | CAR-S6 |
| S7 | Parallel S CAR + CD19 CAR + EGFRt | CAR-S7 |

The specific sequences of each element involved in the CARs described in FIG. 1 and Table 1 are as follows:

```
S scFv (S scFv) Heavy chain
                                       (SEQ ID NO: 9)
QVQLVQSGAEVKKPGASVKLSCKASGYTFTDYYIHWVRQAPGQGLEWIGY

INPNSGYTNYAQKFQGRATMTADKSINTAYVELSRLRSDDTAVYFCTRYM

WERVTGFFDFWGQGTMVTVSS

S scFv (S scFv) Light chain
                                      (SEQ ID NO: 10)
DIQMTQSPSSVSASVGDRVTITCLASEDISDDLAWYQQKPGKAPKVLVYT

TSSLQSGVPSRFSGSGSGTDFTLTISSLQPEDFATYFCQQTYKFPPTFGG

GTKVEIKR

BB scFv Heavy chain
                                      (SEQ ID NO: 13)
DIVLTQSPPSLAMSLGKRATISCRASESVTILGSHLIHWYQQKPGQPPTL

LIQLASNVQTGVPARFSGSGSRTDFTLTIDPVEEDDVAVYYCLQSRTIPR

TFGGGTKLEIK

BB scFv Light chain
                                      (SEQ ID NO: 14)
QIQLVQSGPELKKPGETVKISCKASGYTFTDYSINWVKRAPGKGLKWMGW

INTETREPAYAYDFRGRFAFSLETSASTAYLQINNLKYEDTATYFCALDY

SYAMDYWGQGTSVTVSSAAA

April chain
                                      (SEQ ID NO: 15)
SVLHLVPINATSKDDSDVTEVMWQPALRRGRGLQAQGYGVRIQDAGVYLL

YSQVLFQDVTFTMGQVVSREGQGRQETLFRCIRSMPSHPDRAYNSCYSAG

VFHLHQGDILSVIIPRARAKLNLSPHGTFLGFVKLSGGGSDP

CD8 Signal peptide
                                      (SEQ ID NO: 16)
MALPVTALLLPLALLLHAARP (G4S)3 Linker peptide
                                      (SEQ ID NO: 17)
GGGGSGGGGSGGGGS (G4S)5 Linker peptide
                                      (SEQ ID NO: 18)
GGGGSGGGGSGGGGSGGGGSGGGGS 218 Linker peptide
                                      (SEQ ID NO: 19)
GSTSGSGKPGSGEGSTKG CD8 Hinge region
                                       (SEQ ID NO: 8)
TTTPAPRPPTPAPTIASQPLSLRPEACRPAAGGAVHTRGLDFACD
or
                                      (SEQ ID NO: 37)
KPTTTPAPRPPTPAPTIASQPLSLRPEASRPAAGGAVHTRGLDFASDKP
or
                                      (SEQ ID NO: 38)
SGTTTPAPRPPTPAPTIASQPLSLRPEACRPAAGGAVHTRGLDFACD CD8 Transmembrane region
                                       (SEQ ID NO: 7)
IYIWAPLAGTCGVLLLSLVITLYC CD28 Transmembrane region
                                       (SEQ ID NO: 6)
FWVLVVVGGVLACYSLLVTVAFIIFWV 41BB Signaling region
                                       (SEQ ID NO: 5)
KRGRKKLLYIFKQPFMRPVQTTQEEDGCSCRFPEEEEGGCEL CD28 Signaling region
                                       (SEQ ID NO: 4)
RSKRSRLLHSDYMNMTPRRPGPTRKHYQPYAPPRDFAAYRS CD3z Signaling region
                                       (SEQ ID NO: 3)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
or
                                      (SEQ ID NO: 39)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

2A Peptide
                                       (SEQ ID NO: 2)
GSGATNFSLLKQAGDVEENP FMC63 scFv (CD19 scFv) Heavy chain
                                      (SEQ ID NO: 11)
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS

FMC63 scFv (CD19 scFv) Light chain
                                      (SEQ ID NO: 12)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT

GM-C SF Signal peptide
                                       (SEQ ID NO: 1)
MLLLVTSLLLCELPHPAFLLIP EGFRt Sequence
                                      (SEQ ID NO: 20)
RKVCNGIGIGEFKDSLSINATNIKHFKNCTSISGDLHILPVAFRGDSFTH

TPPLDPQELDILKTVKEITGFLLIQAWPENRTDLHAFENLEIIRGRTKQH

GQFSLAVVSLNITSLGLRSLKEISDGDVIISGNKNLCYANTINWKKLFGT
```

-continued

SGQKTKIISNRGENSCKATGQVCHALCSPEGCWGPEPRDCVSCRNVSRGR

ECVDKCNLLEGEPREFVENSECIQCHPECLPQAMNITCTGRGPDNCIQCA

HYIDGPHCVKTCPAGVMGENNTLVWKYADAGHVCHLCHPNCTYGCTGPGL

EGCPTNGPKIPSIATGMVGALLLLLVVALGIGLFM

The CAR genes in Table 1 were cloned into the FUW lentiviral vector backbone to construct a complete lentiviral expression vector that can be used to infect T cells. Specifically, taking BCMA CAR gene as an example for detailed description, the BCMA CAR gene was placed under the action of EF1α (EF-1α) promoter to form a Fuw-EF1α-BCMA CAR; three plasmids, namely the Fuw-EF1α-BCMA CAR, a lentiviral envelope plasmid pMD2.G (Addgene, Plasmid #12259) and a lentiviral packaging plasmid psPAX2 (Addgene, Plasmid #12260), were transferred into 293T using Lipofectamine 3000 to prepare a complete lentiviral expression vector; the viral supernatant was collected at 48 h and 72 h, concentrated via ultracentrifugation; and the concentrated virus can be used to infect T cells.

The results of flow cytometry analysis showed that a lentiviral vector expressing BCMA CAR can be prepared from the constructed CAR gene.

Example 4 Preparation of CAR-T Cells

The experimental method is as follows:
4.1 Lentivirus Infection
Two days after the isolated and purified primary T cells were activated, they were infected with the lentiviral vector using the lentivirus constructed in Example 3, then transferred to a cell culture flask, and cultured in a constant temperature incubator at 37° C., 5% $CO_2$.
4.2 Proliferation of Cells and Detection of CAR Positive Rate
After the third day of infection and before cryopreservation, samples were taken for detecting the cell number and the percentage of BCMA-positive cells using the BCMA antigen, that is, detecting the CAR-positive rate of the T cells. Half of the medium was replaced every 2 to 3 days.

The results showed that using the lentiviral vector constructed in Example 3, each CAR-T cell was successfully constructed, and the naming thereof are shown in Table 1.

Figure 2:
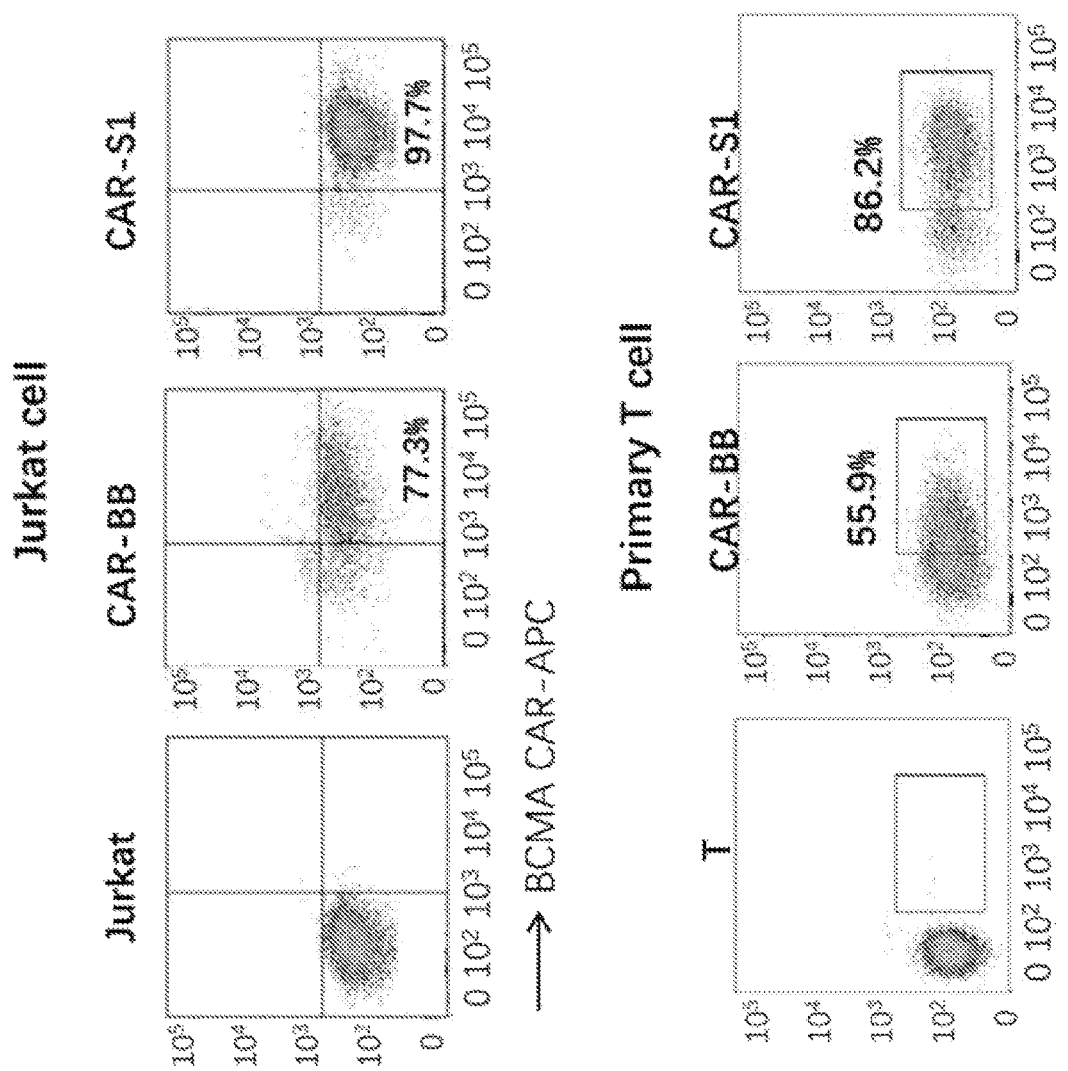
FIG. 2 shows the analysis results of flow cytometry of the expression of CAR-BB and CAR-S1 on the surfaces of Jurkat cells and primary T cells, respectively according to the present invention.

Specifically, the construction results of BCMA CAR-T cells are shown in FIG. 2. The expression of BCMA CAR can be detected in both CAR-BB and CAR-S1 CAR-T cells after virus transfection, and the CAR expression can reach more than 50%.

Example 5 In Vitro Killing of Cells

In vitro killing experiments were performed with the CAR-S1 CAR-T cells, CAR-BB CAR-T cells and CAR-April CAR-T cells obtained in Example 4. The RTCA method was used to test the killing of CAR-T cells against the target cells, the Hela cell lines overexpressing BCMA.

Figure 3:
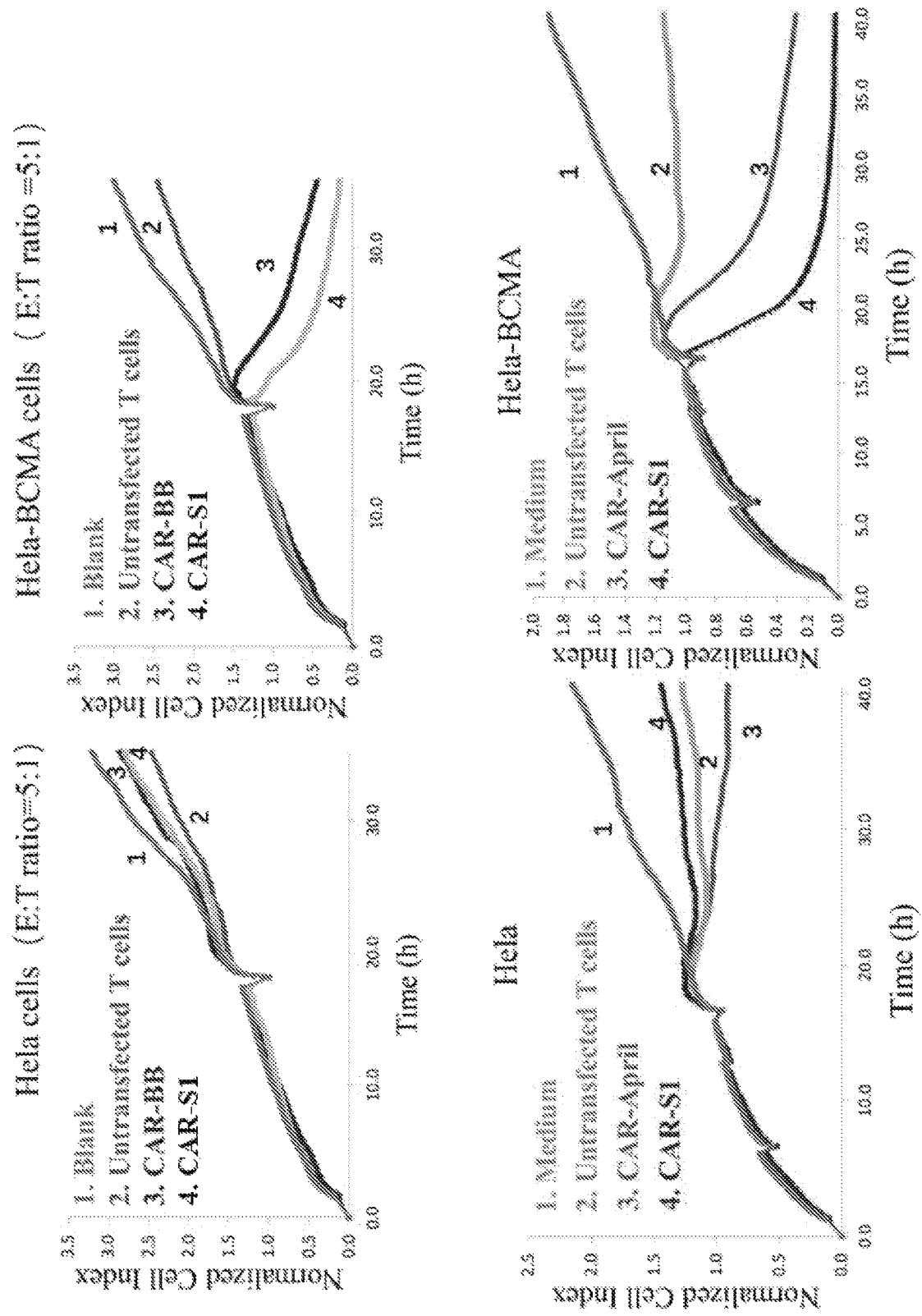
FIG. 3 shows the killing results (RTCA method) of CAR-BB and CAR-S1 against Hela cells and BCMA-overexpressing cells (Hela-BCMA), respectively, and the killing results (RTCA method) of CAR-April and CAR-S1 against Hela cells and BCMA-overexpressing cells (Hela-BCMA), respectively according to the present invention.

The results are shown in FIG. 3 (tested using the RTCA method), the NT control (untransfected T cell control) and medium control (blank control) had no killing on the Hela-BCMA cells, while CAR-S1 cells can perform killing function specific to BCMA, and CAR-S1 cells showed better results than CAR-BB cells in killing BCMA-positive Hela-BCMA cells.

Luciferase-labeled tumor target cells were used for the detection of the killing ability. By transferring the luciferase gene into the target cells, stably transfected cell strains MM.1s-Luc and RPMI8226-Luc were obtained after clonal screening. During the experiment, by adding a luciferin substrate, luciferase reacts with the luciferin to produce fluorescence, and by detecting the intensity of fluorescence, the activity of luciferase can be measured, then the survival ratio of the cells can be detected, and the killing effect of the CAR-T cells can be obtained.

Figure 4:
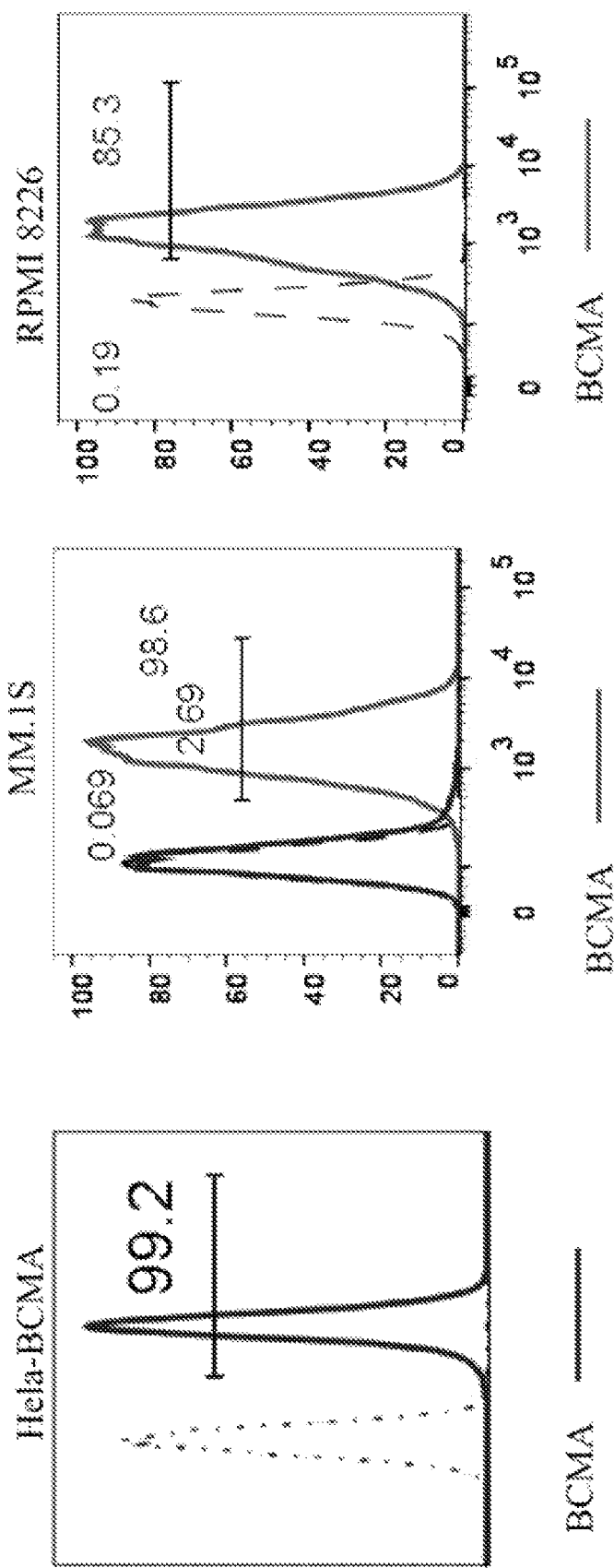
FIG. 4 shows the BCMA expression of the target cells used in the present invention.
Figure 5:
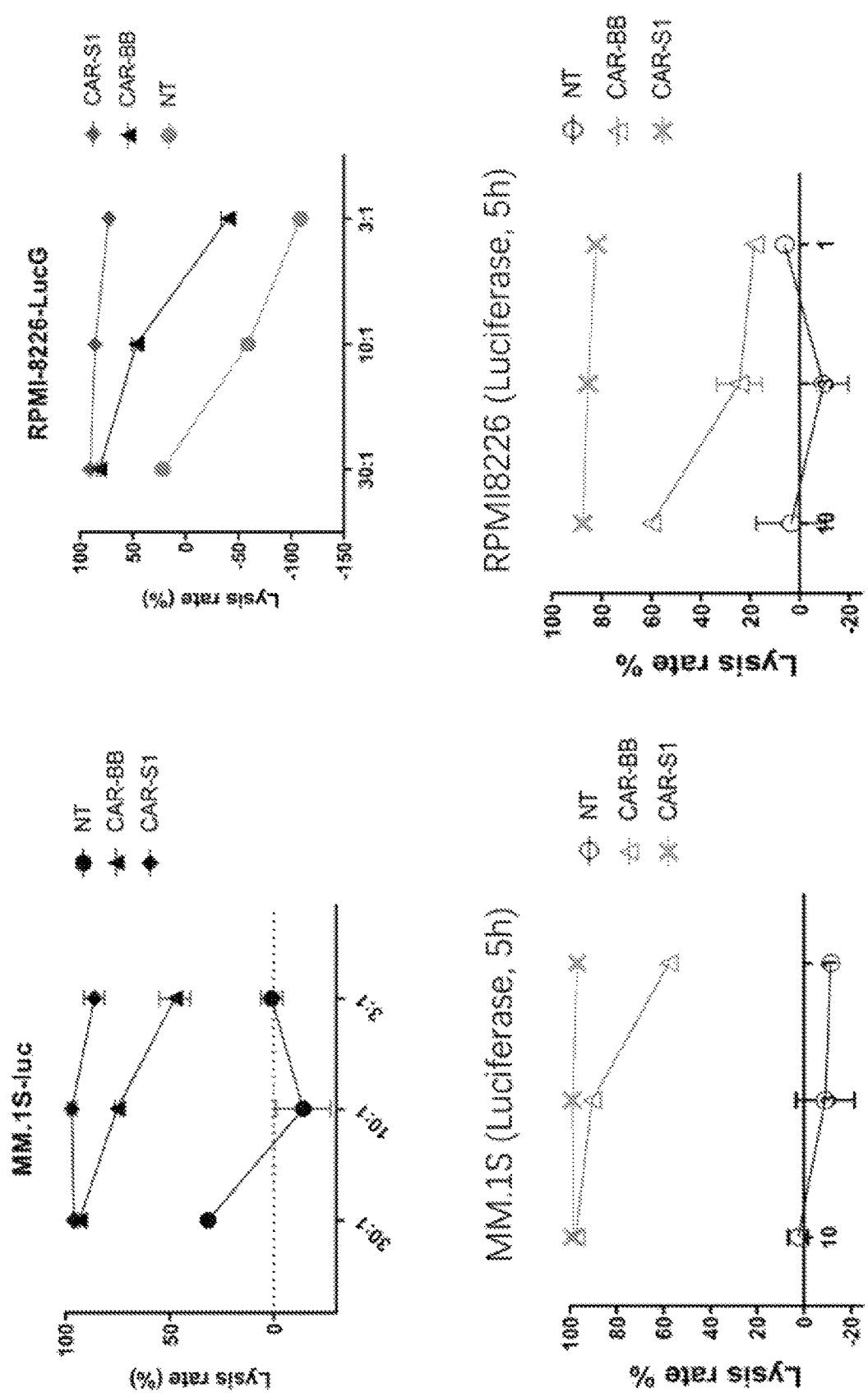
FIG. 5 shows the results of in vitro killing experiments (Luciferase method) of different batches of CAR-BB and CAR-S1 against MM.1s cells and RPMI-8226 cells, respectively according to the present invention.

FIG. 4 shows the antigen expression on the surface of the target cells. FIG. 5 shows that under the same E:T ratio, NT cells have no killing function, the CAR-S1 cells have a dose-dependent killing effect on the MM.1 S-Luc cells (MM.1S cells transferred with luciferase genes) and the RPMI8226-Luc cells (RPMI8226 cells transferred with luciferase genes), and CAR-S1 cells showed better killing ability than CAR-BB and CAR-April.

In addition, the applicant had also constructed CAR-T cells using a variety of targeted BCMA scFv commonly found in the art, and as tested, none of these CAR-T cells exhibited an ideal killing function.

In summary, after the CAR-T cells were co-cultured with the target cells (BCMA overexpressing cells, and BCMA-positive tumor cells, MM.1s-Luc and RPMI8226 cells), the target cells can be lysed by the CAR-T cells targeting BCMA, and CAR-S1 showed higher killing ability than CAR-BB. Some other CAR-T cells constructed by scFvs targeting BCMA commonly found in the art did not show an ideal killing function.

Example 6 Detection of Cytokine Release

The CAR T cells (CAR-S1 CAR-T cells and CAR-BB CAR-T cells) targeting BCMA obtained in Example 4 were mixed with tumor cells (Hela, Hela-BCMA, Hela-CD19, or Hela-BCMA-CD19), and placed in RPMI medium. The density of each cell density was prepared to be $1\times10^4$ cells/ml. 100 ul of each of CAR-T cells and tumor cells were placed in a 96-well plate, and co-cultured overnight. The supernatant was collected, after centrifugation, the supernatant was taken to detect the release level of the cytokine IFN-7, etc. The Elisa kit was used for detection.

Figure 6:
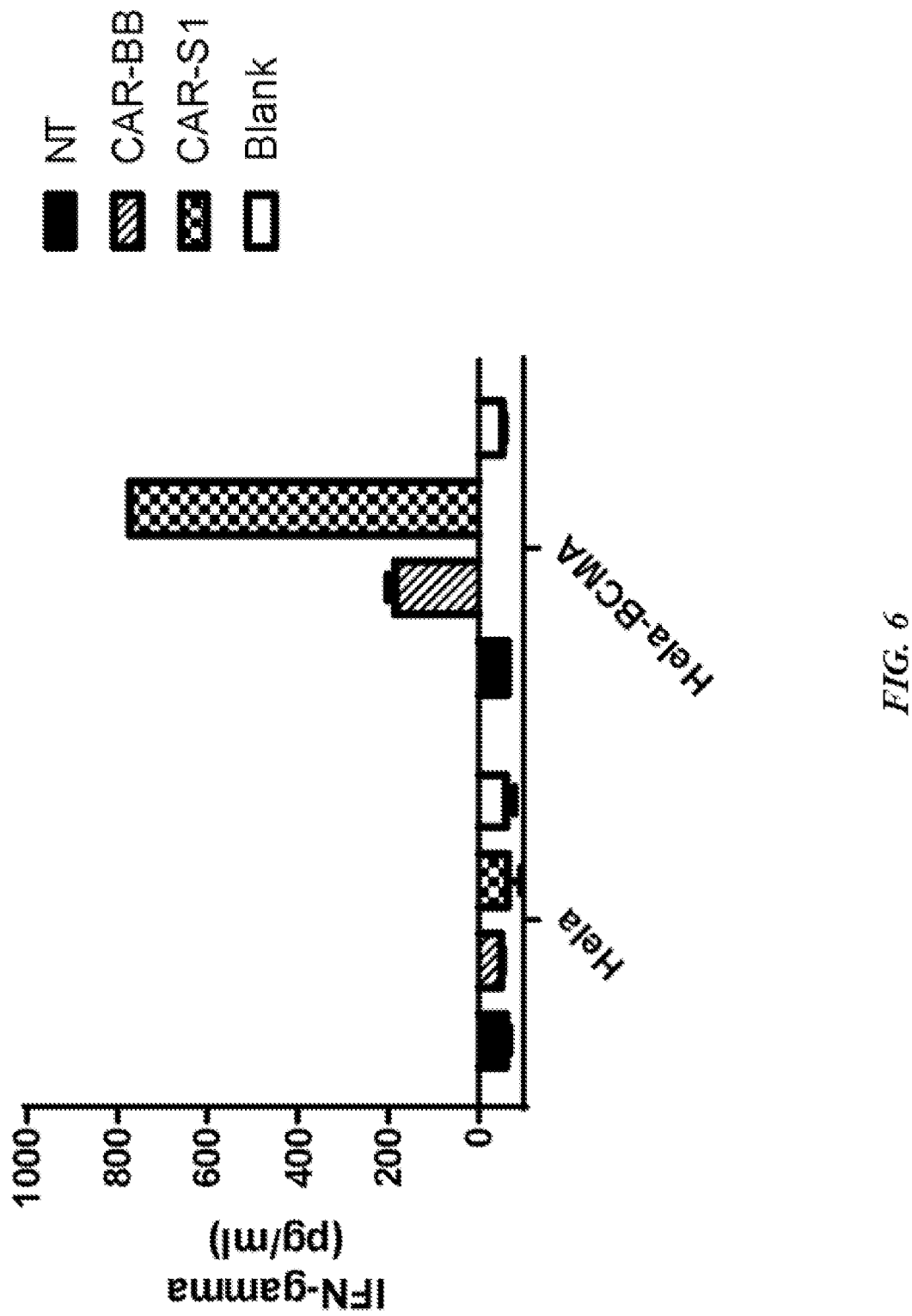
FIG. 6 shows the release of cytokine IFNr during the killing process of CAR-BB and CAR-S1 against Hela cells and BCMA-overexpressing cells (Hela-BCMA), respectively according to the present invention.

The results are shown in FIG. 6. After co-stimulated by Hela-BCMA target cells, the secretion of cytokine INF-γ of the CAR-S1 was significantly higher than that of the CAR-BB, while there was no significant secretion in NT and Medium groups.

Example 7 Study on In Vivo Drug Efficacy

NOG mice aged 6-12 weeks were selected and injected with $1\times10^7$ RPMI8226 cells subcutaneously. Two days later, the tumor graft burden was measured. After 10 days, the grouping was performed, and CAR-S1 CAR-T cells and CAR-BB CAR-T cells were injected one day after the grouping. After the CAR-T treatment, the tumor volume burden of the mice was evaluated twice a week.

Figure 7:
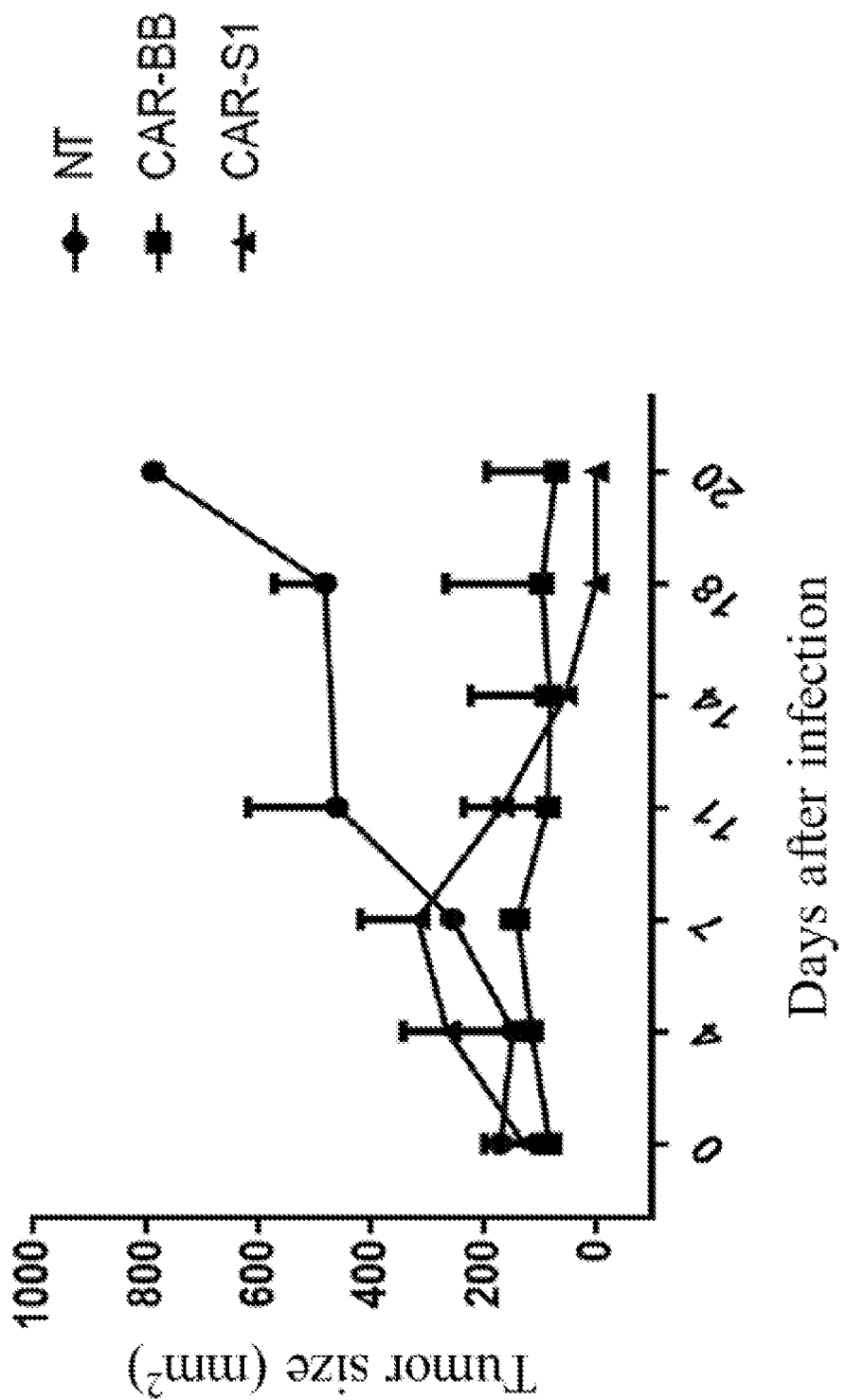
FIG. 7 shows the tumor elimination ability of CAR-BB and CAR-S1 after intravenous re-infusion in the immunodeficient mouse RPMI-8226 subcutaneously modeled model according to the present invention.

The results are shown in FIG. 7. Compared with the control, the tumor burden of the mice injected with CAR-S1 cells was significantly suppressed. The CAR-S1 cells had a slightly higher anti-tumor effect than CAR-BB.

Example 8 Preparation of Dual CAR-T Cells

The experimental method is as follows:
This example involved the CAR-T cells that target both BCMA and CD19, and the structure of the CAR was shown in FIG. 1 (CAR S2, CAR S3, CAR S4, CAR S5, CAR S6 and CAR S7). Among them, the BCMA CAR, CD19 CAR and suicide switch-EGFRt element were connected via a 2A peptide. Among them, the scFv in the BCMA CAR structure was composed of the scFv heavy chain and light chain of S and BB, wherein the S scFv is composed of SEQ ID NO: 9 and SEQ ID NO:10; the BB scFv is composed of SEQ ID NO: 13 and SEQ ID NO: 14; the CD19 scFv is composed of SEQ ID NO: 11 and SEQ ID NO: 12; in addition, the scFv can be replaced with the BCMA binding region composed of a portion of the April sequence (SEQ ID NO: 15) to form a new CAR structure.

The BCMA-CD19 CAR gene was cloned into the vector backbone and placed under the action of the EF1α (EF-1α) promoter to form an EF1α-BCMA-CD19-EGFRt CAR; the EF1α-BCMA-CD19-EGFRt CAR and a lentiviral envelope plasmid were transferred into the 293T using the Lipofectamine3000 to prepare a complete lentiviral expression vector; the viral supernatant was collected at 48 h and 72 h, concentrated via ultracentrifugation; and the concentrated virus can be used to infect T cells.

Lentivirus infection: Two days after the isolated and purified primary T cells were activated, they were infected with the lentiviral vector using the lentivirus constructed as above at MOI (1-10), then transferred to a cell culture flask, and cultured in a constant temperature incubator at 37° C., 5% $CO_2$.

Proliferation of cells and detection of CAR positive rate: After the third day of infection and before cryopreservation, samples were taken for detecting the cell number and the BCMA/CD19 double positive cells, that is, detecting the CAR-positive rate of the T cells. Half of the medium was replaced every 2 to 3 days.

The results showed that using the BCMA-CD19 CAR lentiviral vector, the BCMA-CD19 CAR-T cells were successfully constructed, as shown specifically in FIG. 1 and Table 1.

Figure 8:
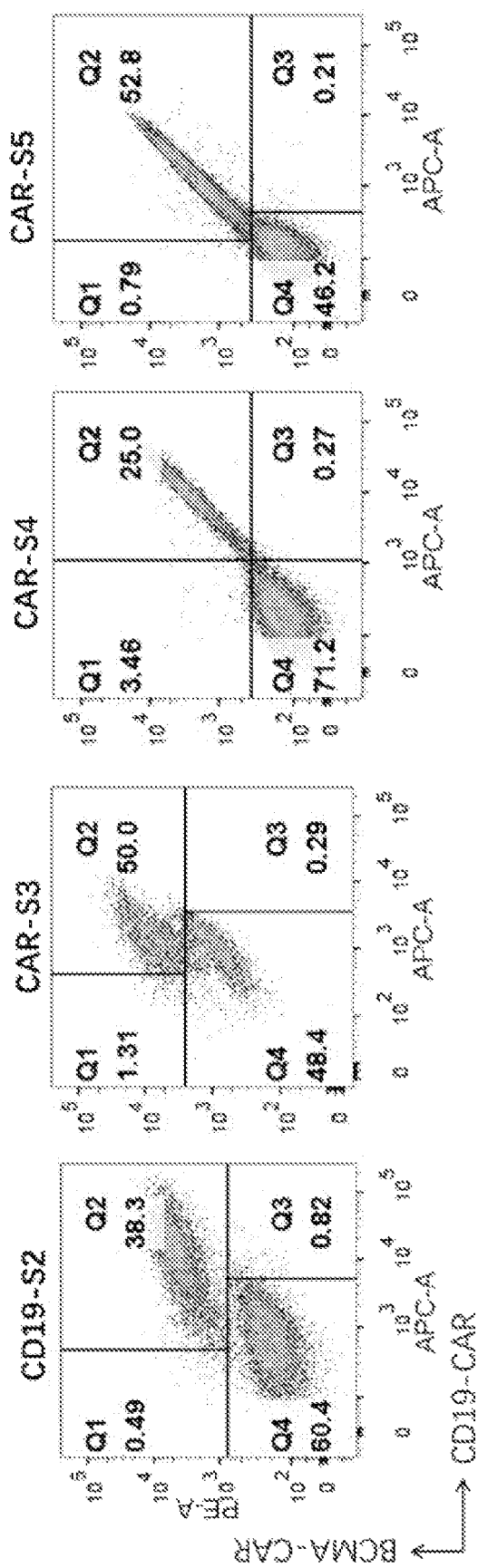
FIG. 8 shows the expression of CD19-CAR and BCMA-CAR in the bispecific CAR-T cell according to the present invention.

The results are shown in FIG. 8. The expression of BCMA CAR and CD19 CAR can be detected on the surface of the virus-transfected T cells using both BCMA antigen and CD19 antigen.

Figure 9:
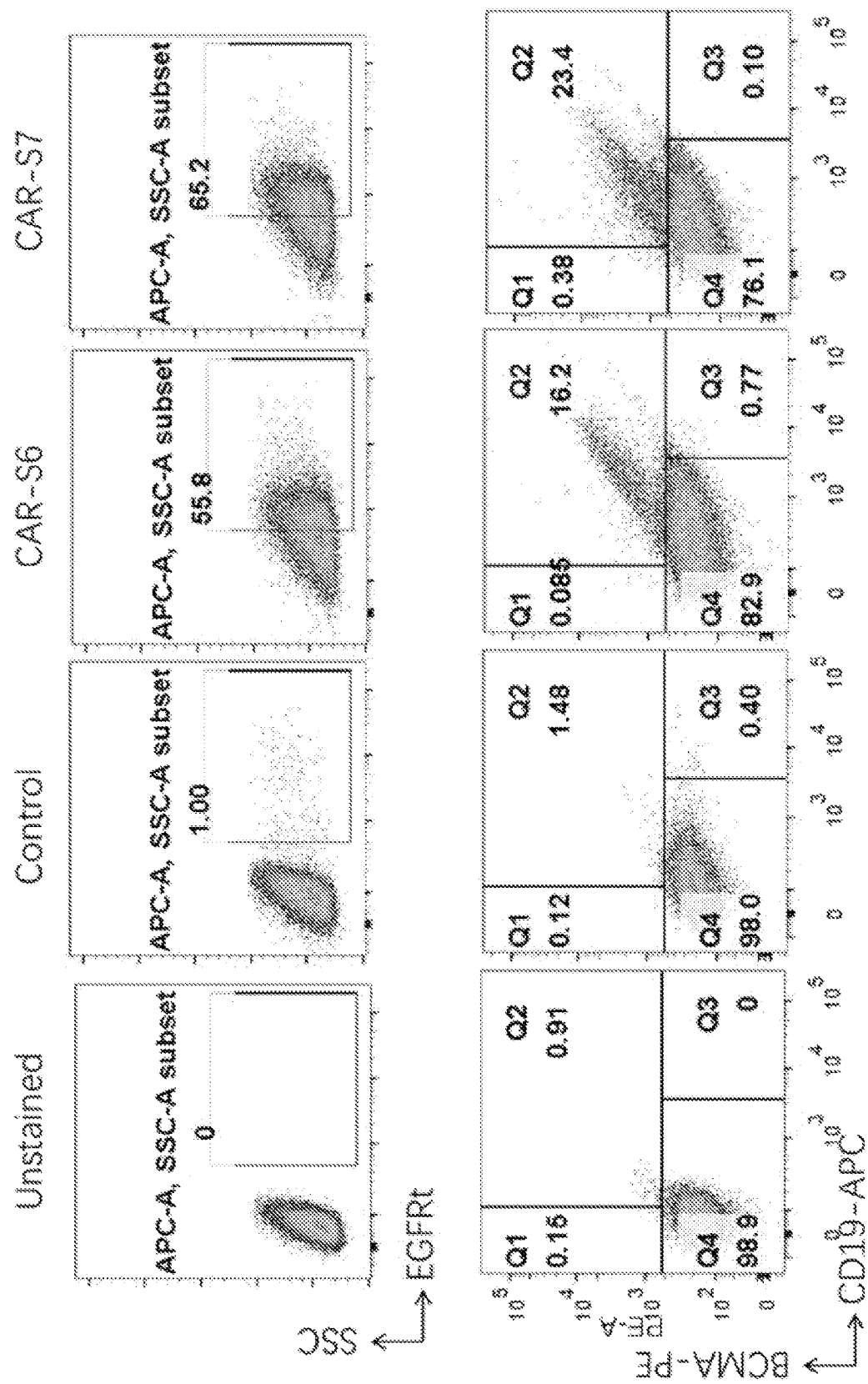
FIG. 9 shows the analysis of the expression of CD19-CAR and BCMA-CAR and the expression of the EGFRt in the bispecific CAR-T cells with the safety switch added according to the present invention.

FIG. 9 shows that the expression of the BCMA CAR, CD19 CAR and EGFRt can all be detected on the surface of the CAR-S6 and CAR-S7 cells.

Example 9 In Vitro Killing of Cells

In vitro killing experiments were performed with the CAR-T cells obtained in Example 8. Overexpressing Hela cell lines that overexpress BCMA and CD19 were used for RTCA, or the luciferase-labeled tumor target cells were used for detection. By transferring the luciferase gene into the target cells, stably transfected cell strains (RPMI8226, MM.1s and Nalm6) were obtained after clonal screening. During the experiment, by adding a luciferin substrate, luciferase reacts with the luciferin to produce fluorescence, and by detecting the intensity of fluorescence, the activity of luciferase can be measured, then the survival ratio of the cells can be detected, and the killing effect of the CART cells can be obtained.

The results showed that after the CAR-T cells were co-cultured with the target cells (CD19/BCMA double positive, CD19 single positive, and BCMA single positive cells), all target cells would be lysed, indicating that the BCMA-CD19 CAR-T had killing effect on all of the CD19/BCMA double positive, CD19 single positive, and BCMA single positive cells.

Figure 10A:
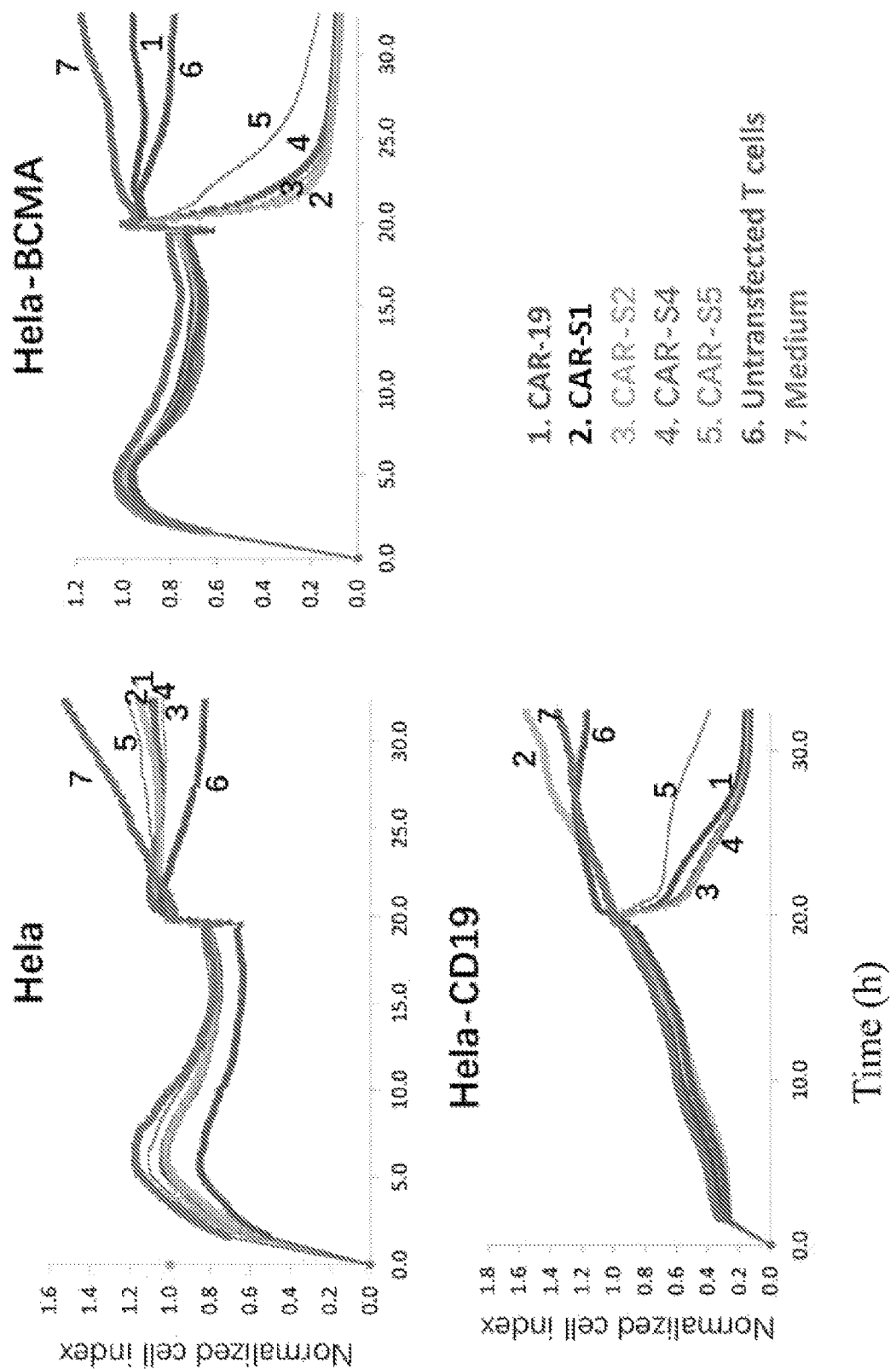
FIG. 10 shows the comparison of the killing of Hela cells and antigen-overexpressing Hela cell lines, Hela-BCMA, Hela-CD19 and Hela-BCMA-CD19, by different batches of CAR-19, CAR-BCMA and bispecific CAR-T according to the present invention.
Figure 10B:
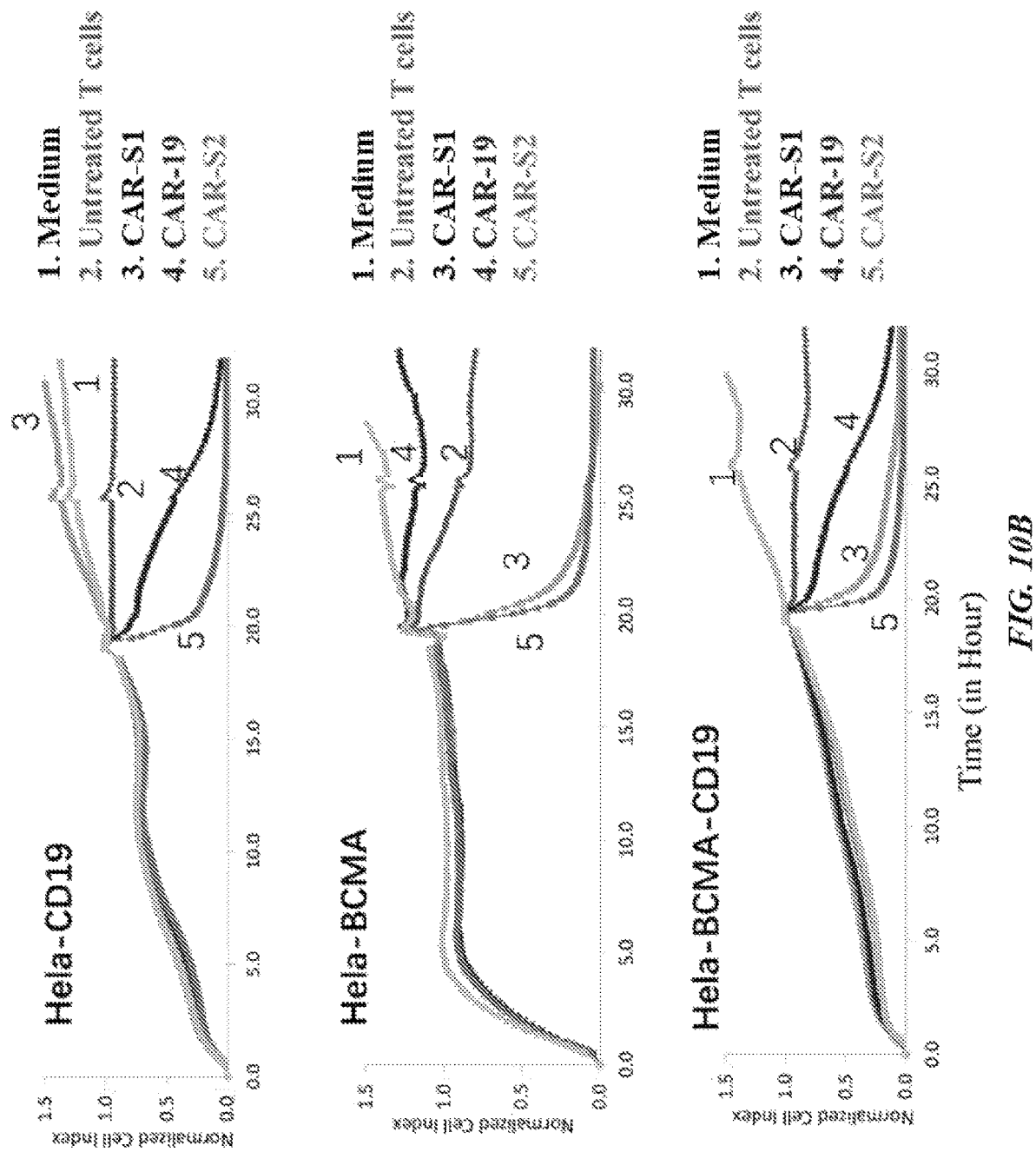

The specific results are shown in FIG. 10. The bispecific CAR-T can significantly kill the single-positive CD19-positive target cells (Hela-CD19) or the single-positive BCMA-positive target cells (Hela-BCMA), and it can also significantly kill the CD19/BCMA double positive target cell Hela-BCMA-CD19. It showed that the bispecific CAR-T cells with the combination of BCMA and CD19 had killing effects on both single-target and dual-target cells. A single CAR-T (CAR-19 or CAR-S1) only had killing effect on one target antigen.

Figure 11:
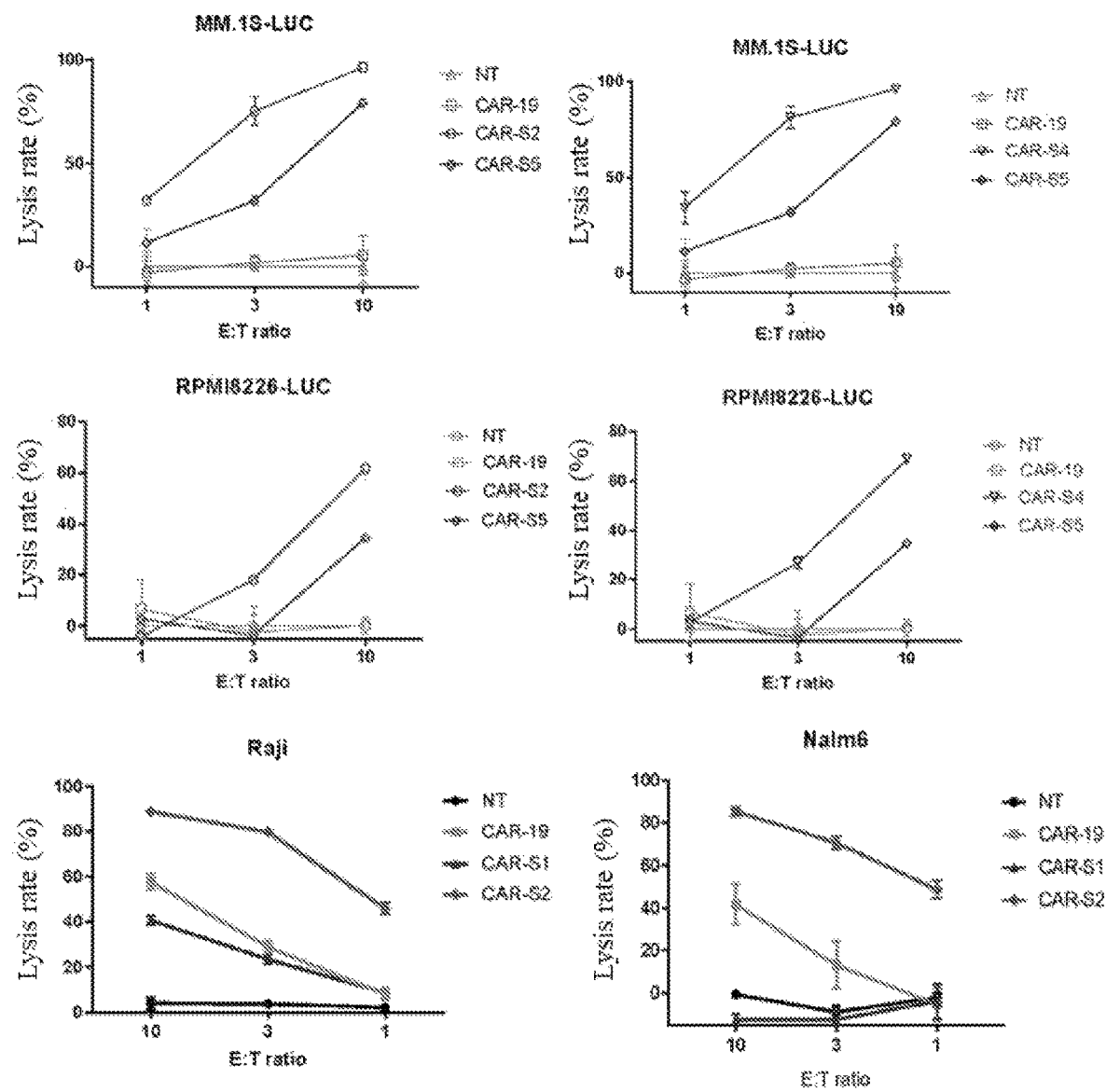
FIG. 11 shows the results of in vitro killing experiments (Luciferase method) of different batches of CAR-CD19, CAR-BCMA and bispecific CAR-T against MM.1s cells, RPMI-8226 cells and Nalm6 cells according to the present invention.

FIG. 11 shows that dual CAR-T can significantly kill the BCMA single-positive tumor target cells MM.1s and RPMI8226. It also significantly killed the CD19-positive tumor target cells Raji and Nalm6. It showed that the dual CAR with the combination of BCMA and CD19 has a killing effect on both BCMA- and CD19-positive tumor target cells.

Example 10 Detection of Cytokine Release

The BCMA-CD19 CAR-T cells (obtained in Example 8) were mixed with tumor cells (Hela-BCMA), and placed in RPMI medium. The density of each cell was prepared to be $1\times10^4$ cells/ml. 100 ul of each of CAR-T cells and tumor cells were placed in a 96-well plate, and co-cultured overnight. The supernatant was collected, after centrifugation, the supernatant was taken to detect the release level of the cytokines. The CBA method was used for detection.

Figure 12:
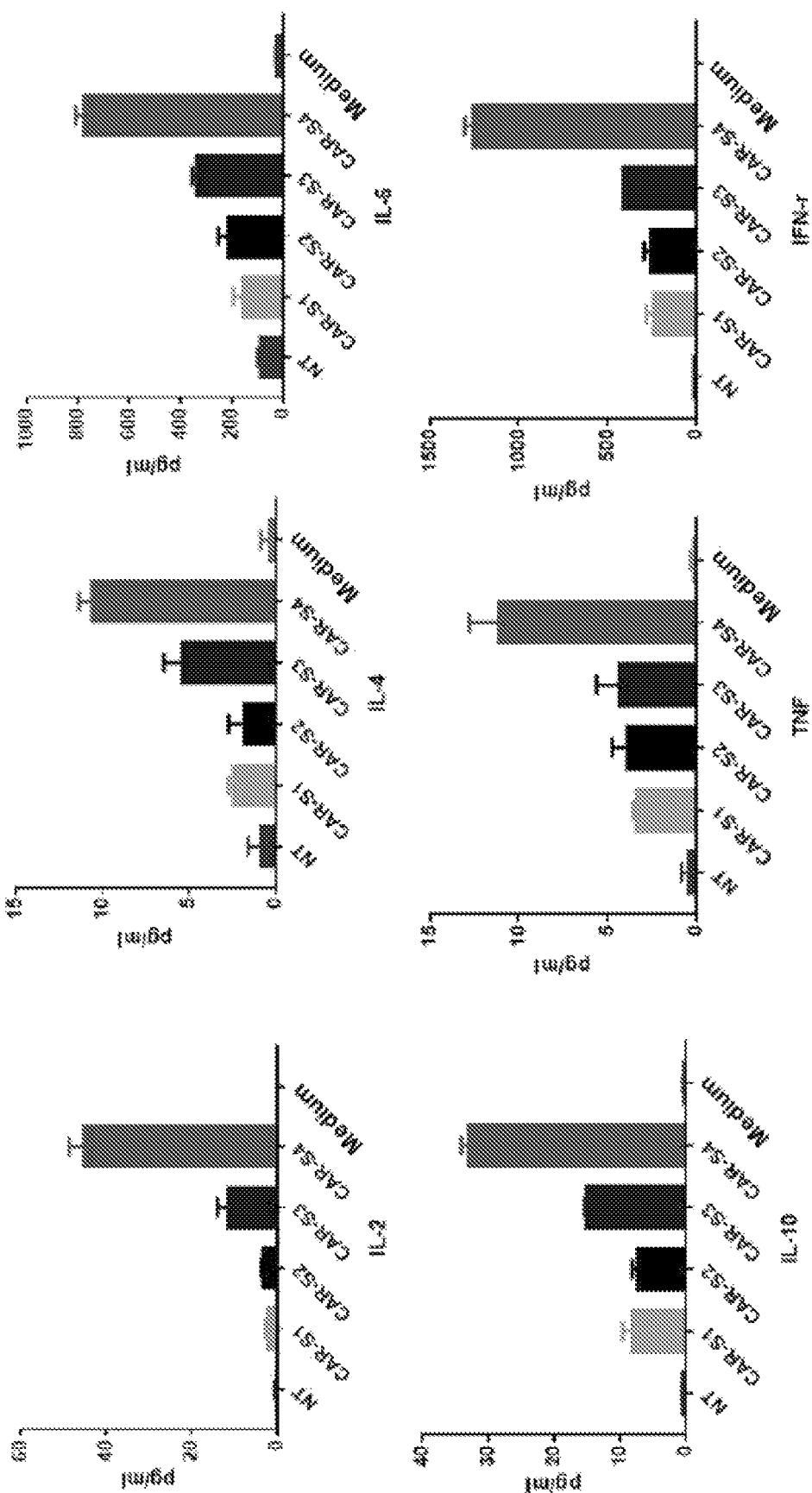
FIG. 12 shows the release of cytokines during the killing process of CAR-BCMA and bispecific CAR-T cells against BCMA-overexpressing Hela cells (Hela-BCMA) according to the present invention.

The results are shown in FIG. 12. The BCMA-CD19 CAR-T can secrete a large amount of cytokines after being stimulated by BCM-positive target cells, and NT secreted only a small amount of cytokines. It showed that the BCMA-CD19 CAR-T can be activated by BCMA.

Example 11 Up-Regulation of CD107 after being Stimulated

The CAR-T cells obtained in Example 8 were activated and then subjected to flow cytometry analysis for changes in CD107a expression, and a tumor cell line expressing CD19 or BCMA was used for co-incubation activation experiments. After co-incubation, the cells were labeled with antibodies for CD3, CD8 and CD107a, and then subjected to flow cytometry analysis.

Figure 13:
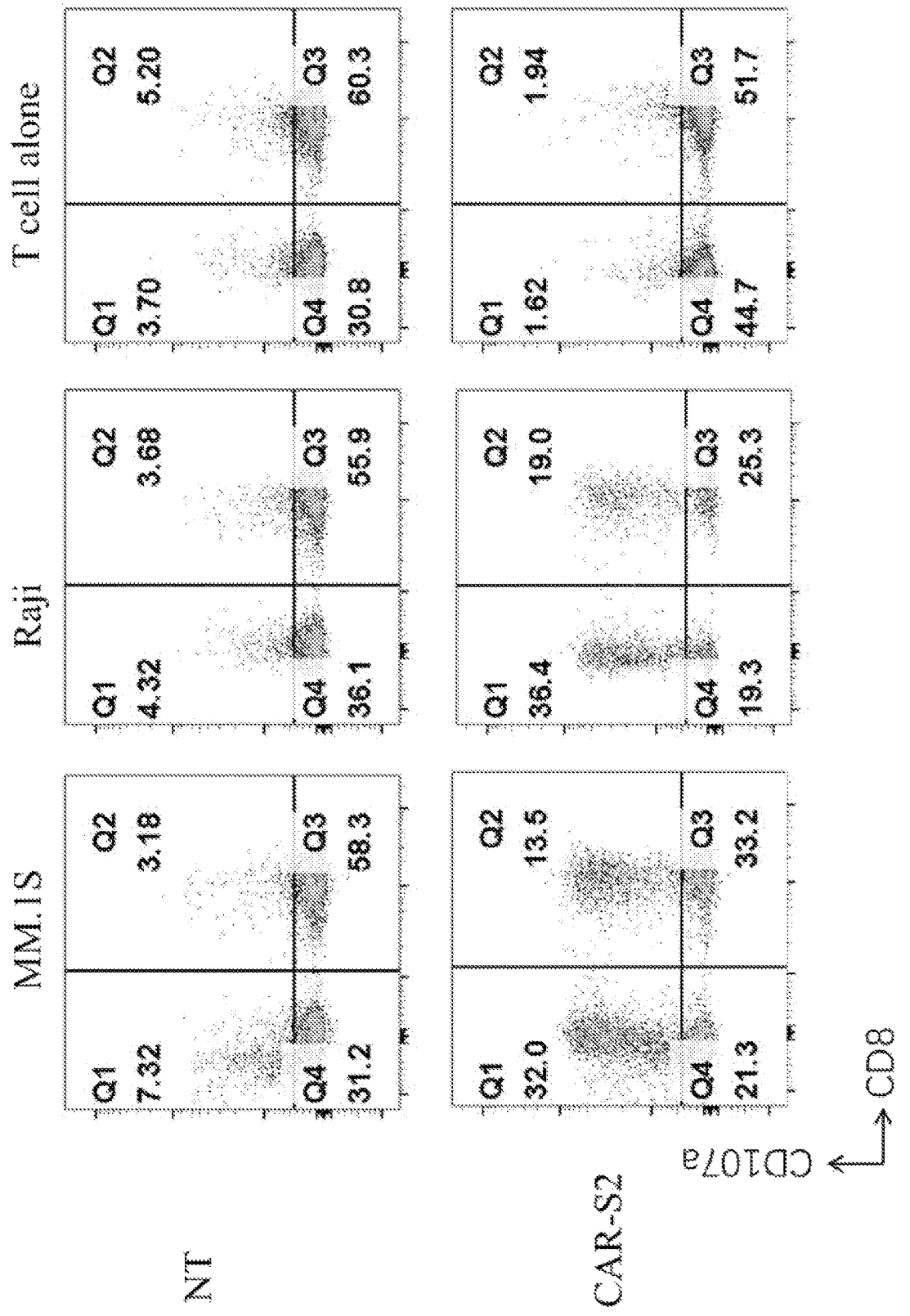
FIG. 13 shows the analysis of expression of CD107a molecules on the surface of dual CAR-T cells after co-cultured with MM.1s or Raji tumor target cells.

The results are shown in FIG. 13. After the dual CAR-T cells were co-cultured with BCMA-positive tumor target cells MM.1s and CD19-positive Raji, the CD107a molecules on the surface of the CAR-T cells were significantly upregulated.

Example 12 Study on In Vivo Drug Efficacy

NOG mice aged 6-12 weeks were selected and injected with $1\times10^7$ RPMI8226 cells subcutaneously. Two days later, the tumor graft burden was measured. After 10 days, they were divided into groups with similar tumor burdens, and CAR-T cells were injected thereto one day after grouping, respectively. After the CAR-T treatment, the tumor volume burden of the mice was evaluated twice a week.

Figure 14:
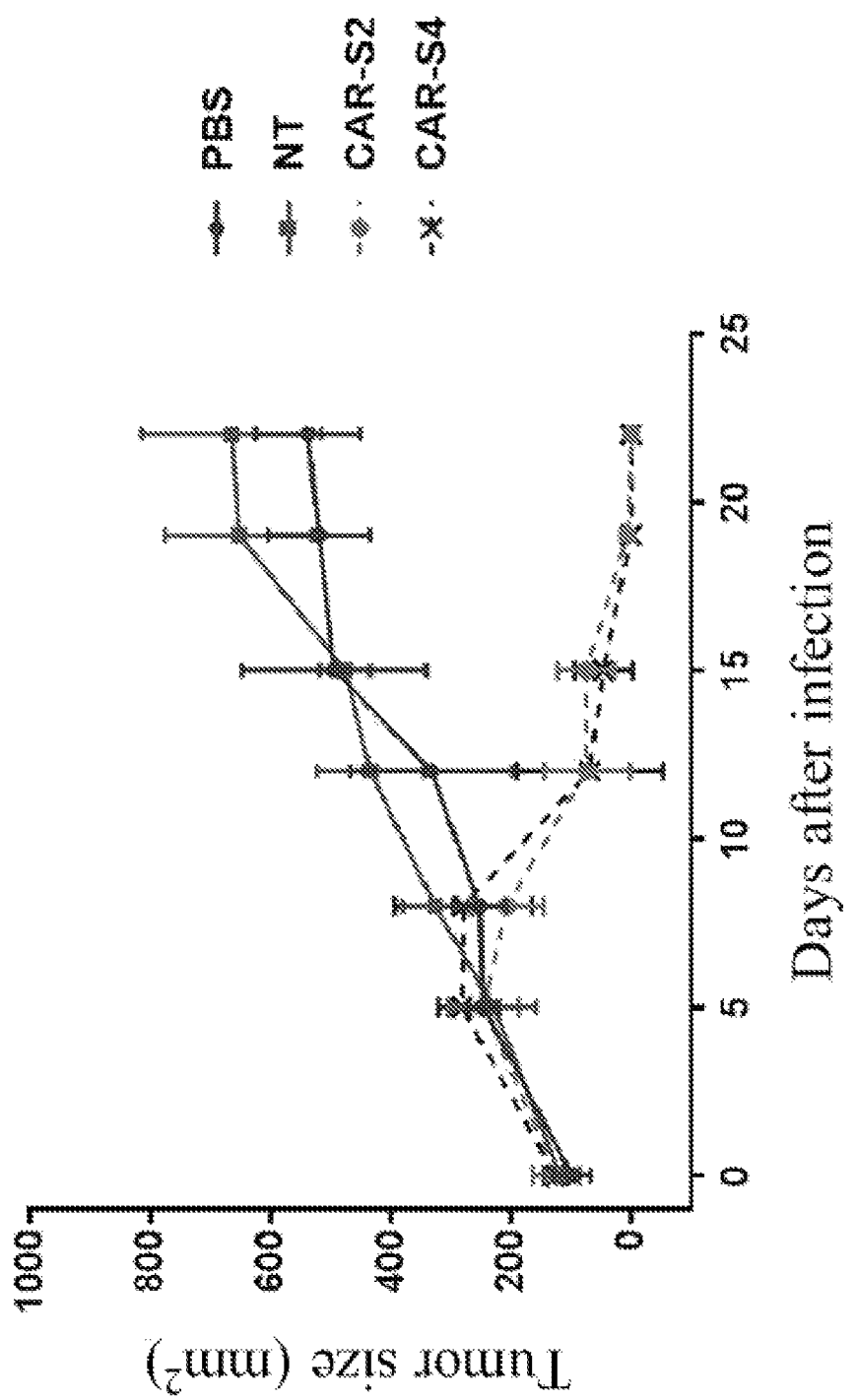
FIG. 14 shows the tumor elimination ability of CAR-S1, bispecific CAR-S2 and CAR-S4 after intravenous re-infusion in the immunodeficient mouse RPMI-8226 subcutaneously modeled model according to the present invention.

The results in FIG. 14 shows that CAR-S2 and CAR-S4 can eliminate the tumors in RPMI8226 cell-subcutaneously modeled mice, indicating their significant anti-tumor efficacy.

At the same time, 6-12 weeks old NOG mice were selected and injected with $1\times10^7$ MM.1s cells intravenously. The tumor graft burden was detected and the mice were evenly divided into groups according to the tumor burden. CAR-T cells were injected one day after grouping. After the CAR-T treatment, the tumor burden of mice was evaluated. Each mouse was intraperitoneally injected with 3 mg d-luciferin (Perkin Elmer Life Sciences), and then photographed with the Xenogen IVIS Imaging System (Perkin Elmer Life Sciences) after four minutes with an exposure time of 30s. The bioluminescence signal was calculated according to the amount of photons emitted, the amount of photons was normalized with the exposure time and the surface area, and the amount of photons/s/cm$^2$/steradian (p/s/cm$^2$/sr) was finally obtained.

Figure 15:
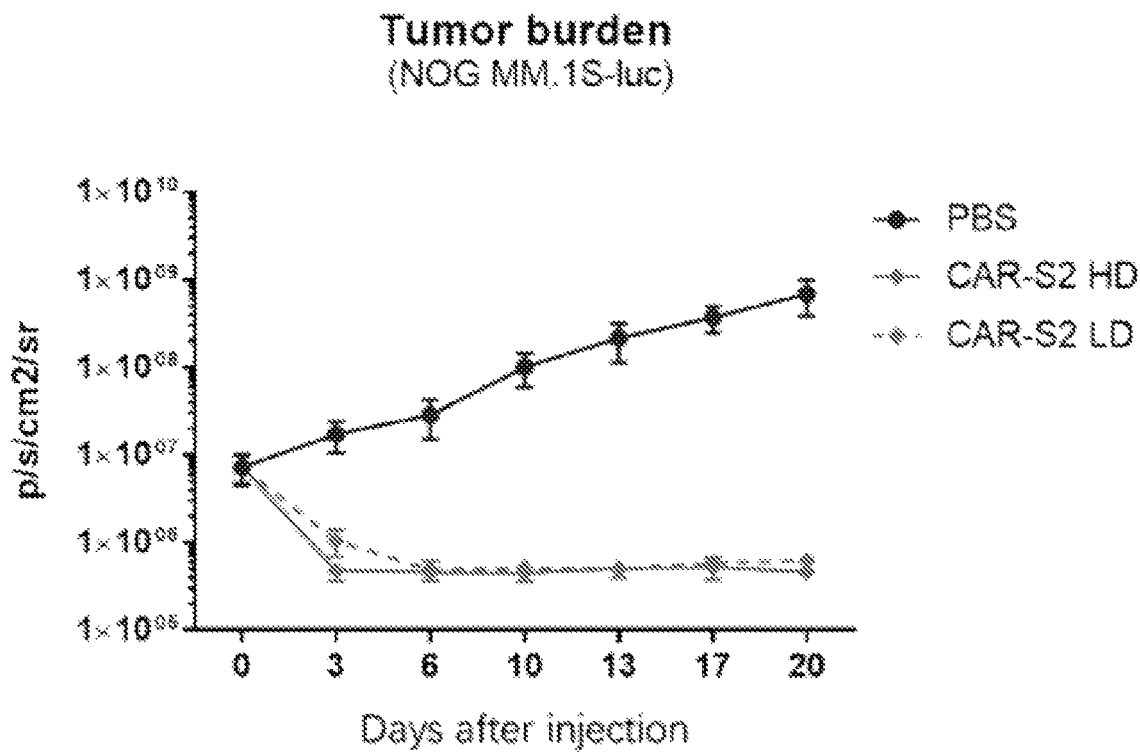
FIG. 15 shows the tumor elimination ability of different doses of the bispecific CAR-S2 and CAR-S4 cells after intravenous re-infusion in the immunodeficient mouse MM.1s-luc intravenously modeled model according to the present invention.
Figure 15:
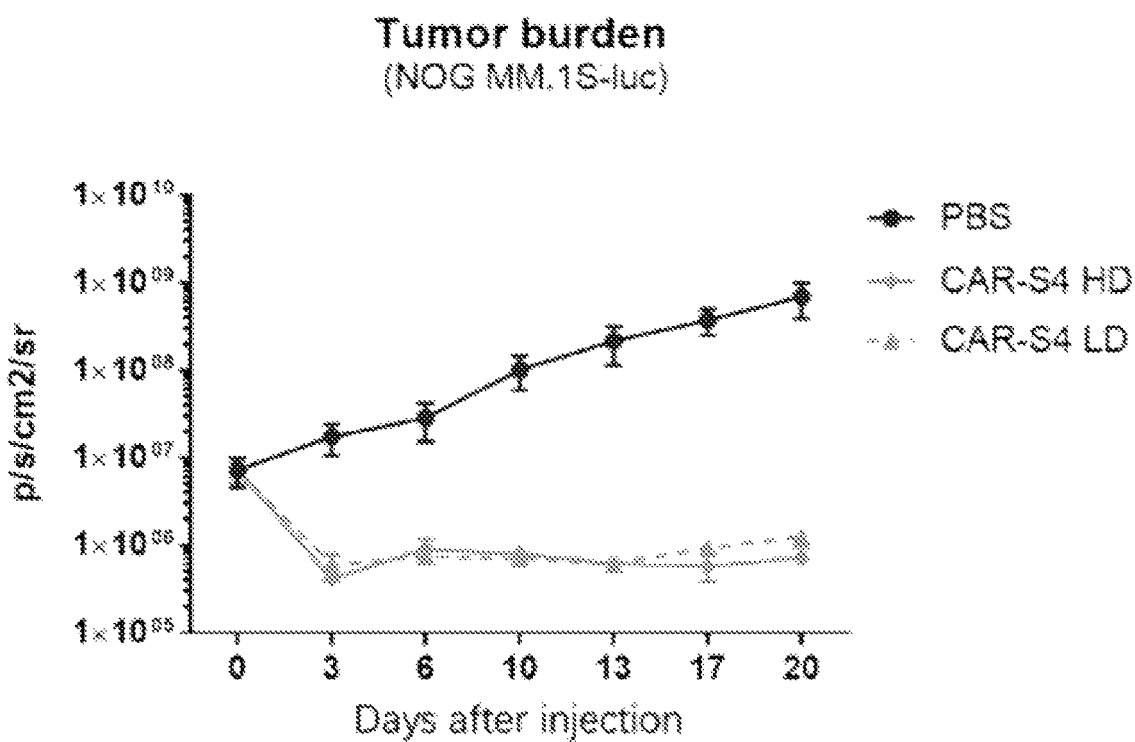

The results in FIG. 15 shows that compared with the control, the tumor burden of mice injected with dual CAR-T cells was significantly reduced until disappeared, indicating that BCMA-CD19 CAR-T cells had a significant anti-tumor effect.

Example 13 Study on the Killing of Tumor-Forming Cells

The recurrence of patients with myeloma (MM) is a common clinical phenomenon, and the clinical manifestations are generally that most of the tumor cells can be eliminated, but the tumor cells capable of clonal proliferation that lead to the recurrence of the tumor tend to have relatively higher drug resistance. In order to investigate the killing ability of the CAR-T cells against the tumor cells capable of clonal proliferation, and to compare the advantages of bispecific CAR-T and single CAR-T cells, this study established a method of myeloma clone formation experiment, and investigated the inhibitory ability of the CAR-Ts to clone formation.

MM tumor cells capable of proliferation can grow in a clonal proliferation medium, but during the experiment, CD34+ hematopoietic stem cells capable of proliferation which may interfere with the experiment are needed to be removed. It is an important issue required to be controlled for this experiment that the cells harvested should be dominated by tumor proliferation cells.

The specific experimental method is as follows:

In the first step, bone marrow mononuclear cells were isolated and extracted using Ficoll and analyzed for phenotype by flow cytometry. In the second step, a CD34+ cell sorting kit was used to remove the CD34+ cells. In the third step, the killing experiment was performed on the obtained cells using different groups of CAR-T cells (dual CAR-T, and single CAR-T). After the completion of killing, the CAR-T cells were removed using a T cell-removing sorting kit. In the fourth step, semi-solid cloning proliferation medium was used for clonal growth, and statistics, counting, and results summary were performed after 1 week to 2 weeks.

Figure 16:
FIG. 16 shows the inhibition ability of different CAR-T cells on the clone formation of CD34-negative monocytes in the bone marrow of MM patients.

The results are shown in FIG. 16. CAR-S2 and CAR-S4 had an advantage in killing clone formation cells or tumor cell precursor cells more significantly than CAR-19 and CAR-S1, indicating that they had a higher ability to inhibit the clone formation of myeloma cells than a single CAR.

Example 14 In Vivo Vein Modeling Experiment of Nalm6

6-12 weeks old NOG mice were selected and injected with 1×10$^7$ Nalm6 cells intravenously. After 6 days, the tumor graft burden was detected and the mice were evenly divided into groups according to the tumor burden. CAR-T cells were injected one day after grouping. After the CAR-T treatment, the tumor burden of mice was evaluated. Each mouse was intraperitoneally injected with 3 mg d-luciferin (Perkin Elmer Life Sciences), and then photographed with the Xenogen IVIS Imaging System (Perkin Elmer Life Sciences) after four minutes with an exposure time of 30s. The bioluminescence signal was calculated according to the amount of photons emitted, the amount of photons was normalized with the exposure time and the surface area, and the amount of photons/s/cm$^2$/steradian (p/s/cm$^2$/sr) was finally obtained.

Figure 17:
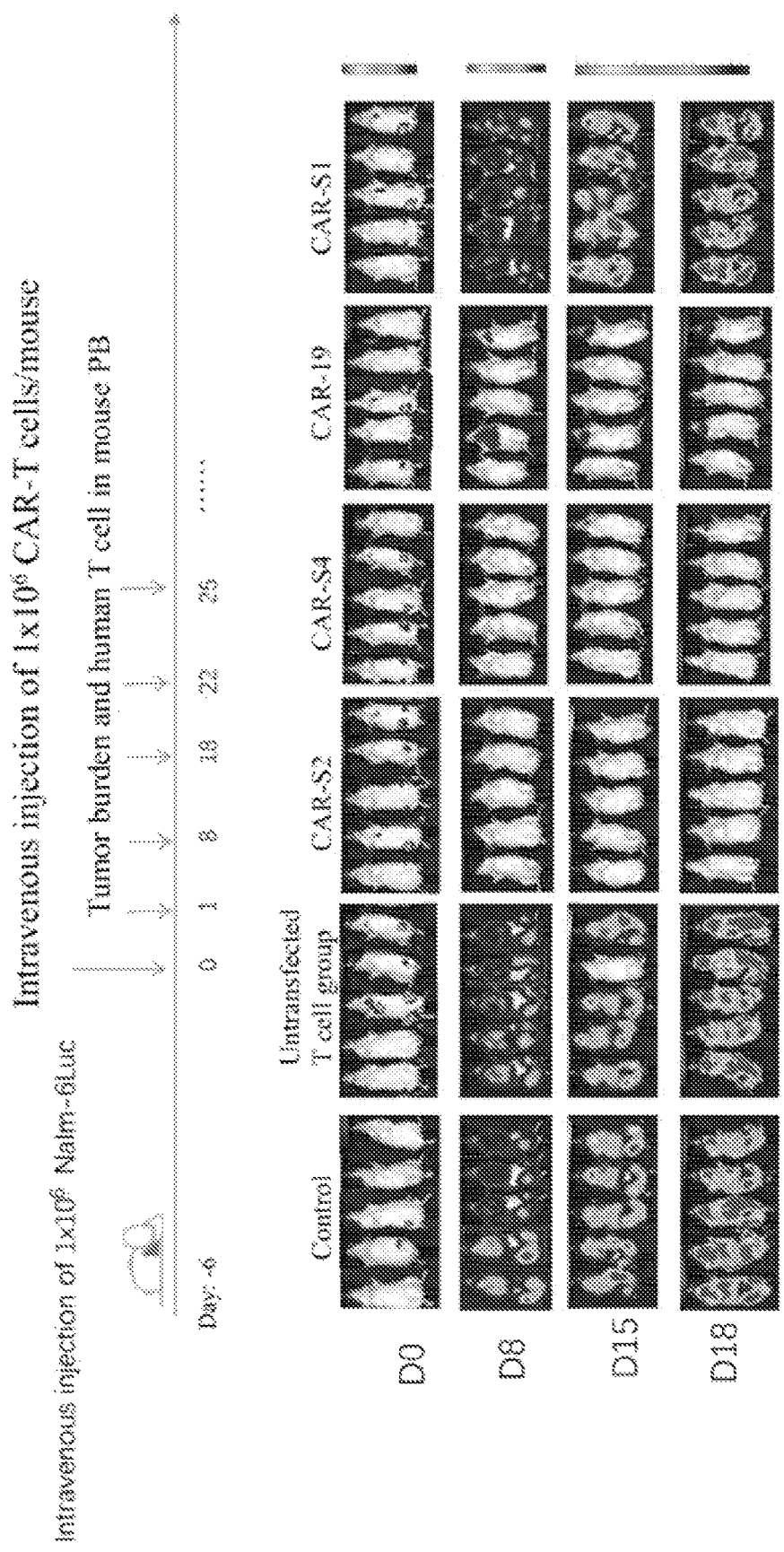
FIG. 17 shows the in vivo tumor elimination ability of different CAR-T cells against the Nalm6-Luc cell modeled NOG mice.

The results are shown in FIG. 17. The tumor burden of the mice injected with CAR-S2 and CAR-S4 was significantly reduced until disappeared, and BCMA-CD19 CAR-T cells had a more significant anti-CD19-positive tumor effect than CAR-19.

Example 15 Safety Switch Experiment of CAR-T Cells

CAR-T containing EGFRt element were stained with EGFR antibody and analyzed by flow cytometry, and the CAR expression was analyzed at the same time.

Figure 18:
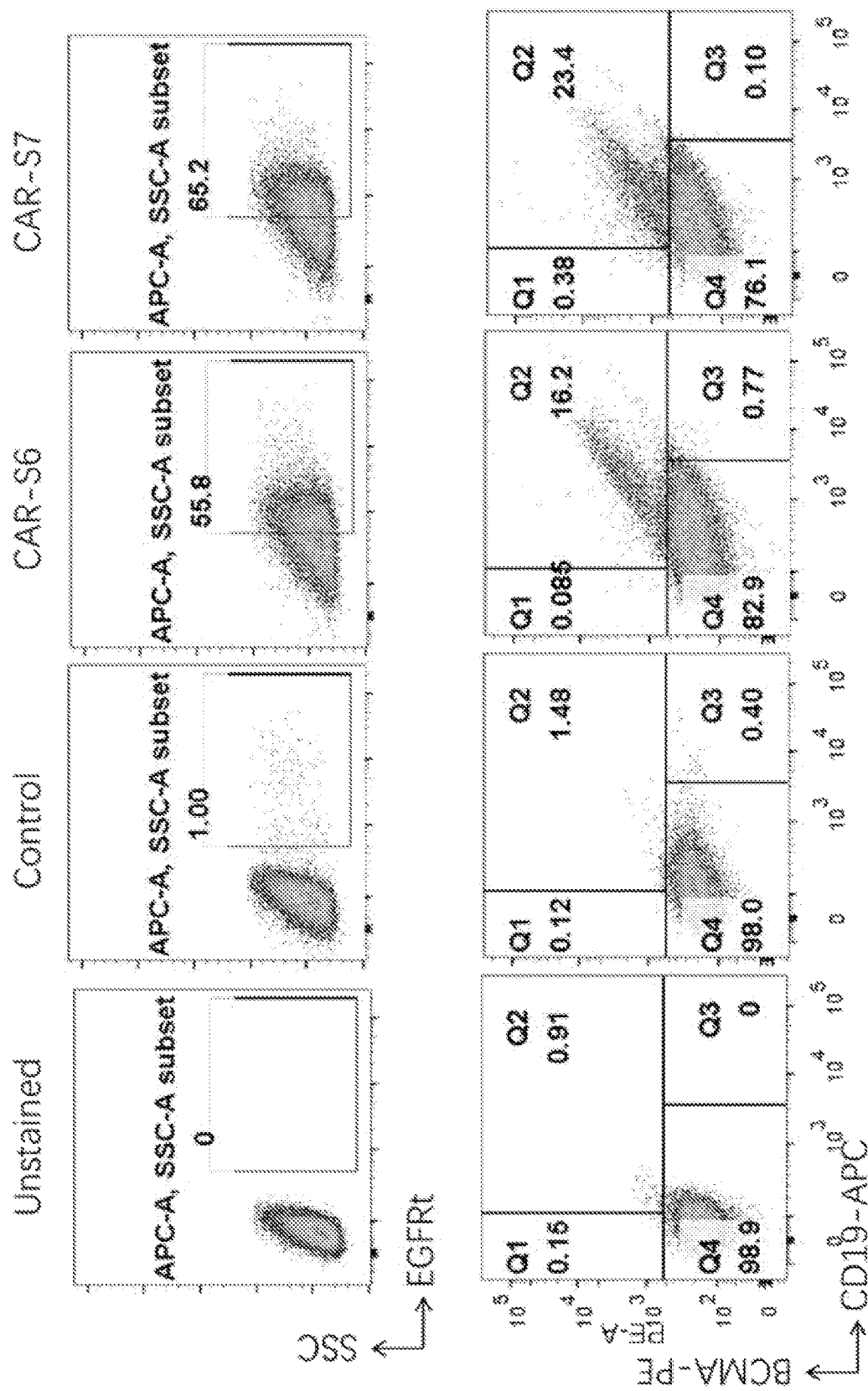
FIG. 18 shows the expression of CAR and safety switch of CAR-T cells on the surface of T cells.

The result is shown in FIG. 18. The expression of the safety switch was detected in the CAR-T cells.

Example 16 Preparation of Humanized CAR-T Cells and Detection of Killing Effect

The methods of Examples 3 and 4 were used to construct the humanized CAR-T cells (CAR-h19) and the humanized dual CAR-T cells (CAR-hS2, and CAR-hS4). The structure of the humanized CAR-T cells was similar to that of CAR-19. The structure of the humanized dual CAR-T cell CAR-hS2 was similar to that of CAR-S2, and the structure of CAR-hS4 was similar to that of CAR-S4, the only difference lied in that a humanized CD19 scFv was used to replace the murine-derived scFv in the original structure. The humanized CD19 scFv comprises an antibody heavy chain variable region as shown in any one of SEQ ID NOs: 21-30 and an antibody light chain variable region as shown in any one of SEQ ID NOs: 31-36.

The method of Example 9 was used to detect the in vitro killing effect of the humanized dual CAR-T cells.

Figure 19:
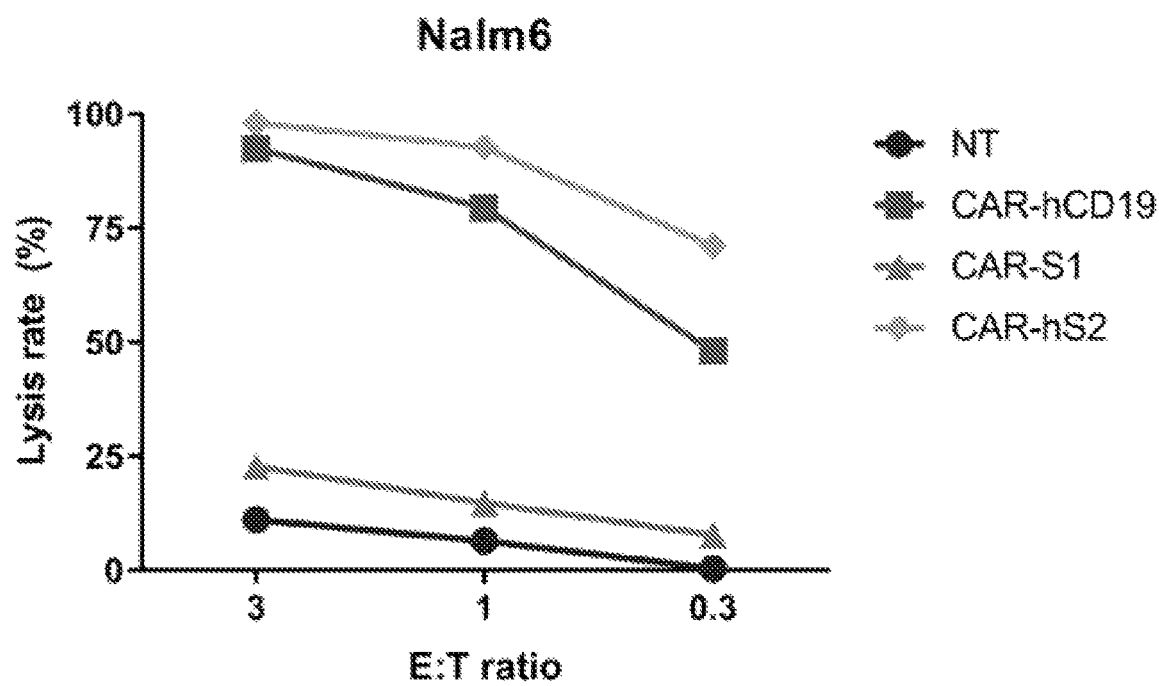
FIG. 19 shows the killing effect (Luciferase method) of different CAR-T cells against Nalm6 or RMPI8226 cells. Compared with single CAR-T cells, dual CAR pairs have stronger ability of killing target cells.
Figure 19:
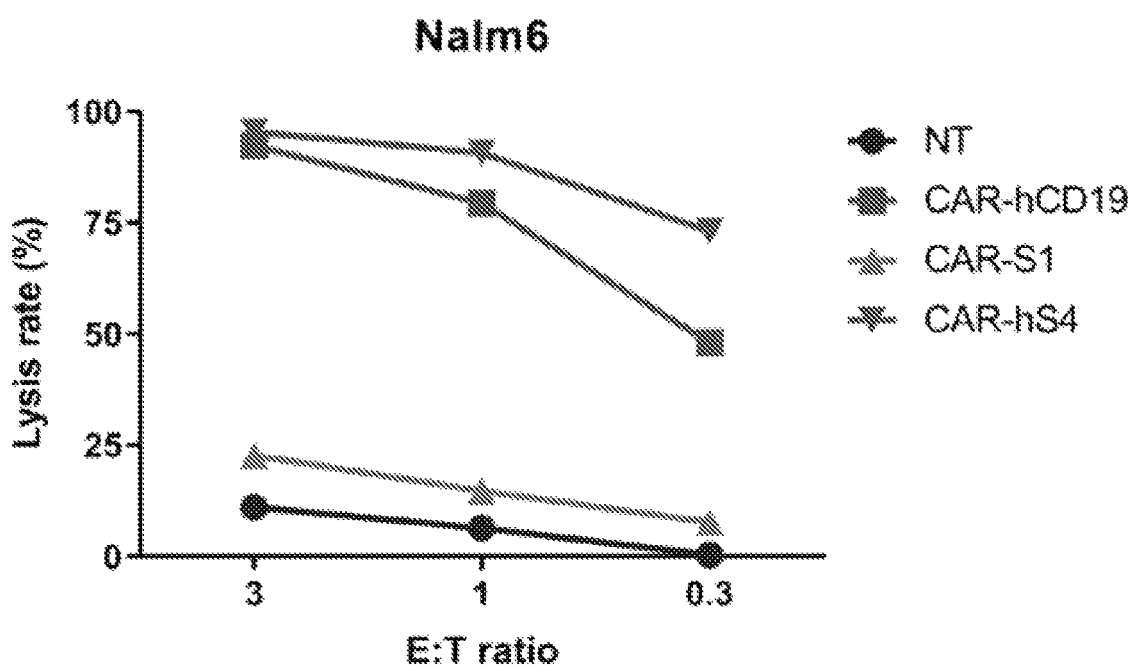
Figure 20:
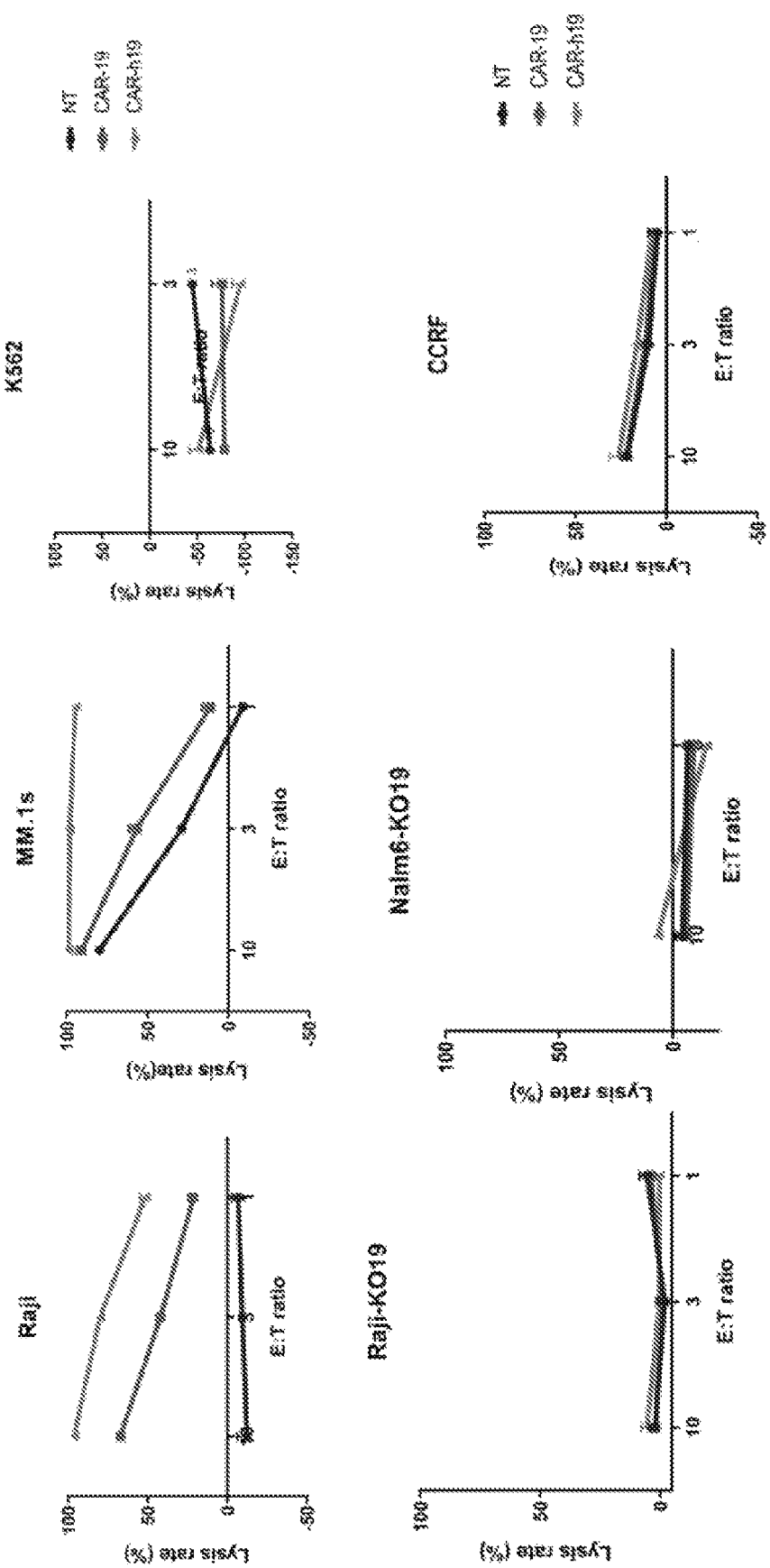
FIG. 20 shows that the different CAR-T cells have no killing ability against negative target cells (K562, Raji-KO19, Nalm6-KO19, and CCRF).

The in vitro killing results are shown in FIG. 19 and FIG. 20. The humanized CAR-T cells and the humanized dual CAR-T cells showed significant killing effects on the target cells without killing non-target cells.

Example 17 Study on In Vivo Drug Efficacy of Humanized CAR-T Cells

NOG mice aged 6-12 weeks were selected and injected with 3×10$^5$ Raji cells subcutaneously. Six days later, the tumor graft burden was measured, and they were divided into groups with similar tumor burdens, and the dual CAR-T cells prepared as above were injected thereto one day after grouping, respectively. After the CAR-T treatment, the tumor volume burden of the mice was evaluated. Each mouse was intraperitoneally injected with 3 mg d-luciferin (Perkin Elmer Life Sciences), and then photographed with the Xenogen IVIS Imaging System (Perkin Elmer Life Sciences) after four minutes with an exposure time of 30s. The bioluminescence signal was calculated according to the amount of photons emitted, the amount of photons was normalized with the exposure time and the surface area, and the amount of photons/s/cm$^2$/steradian (p/s/cm$^2$/sr) was finally obtained.

Figure 21:
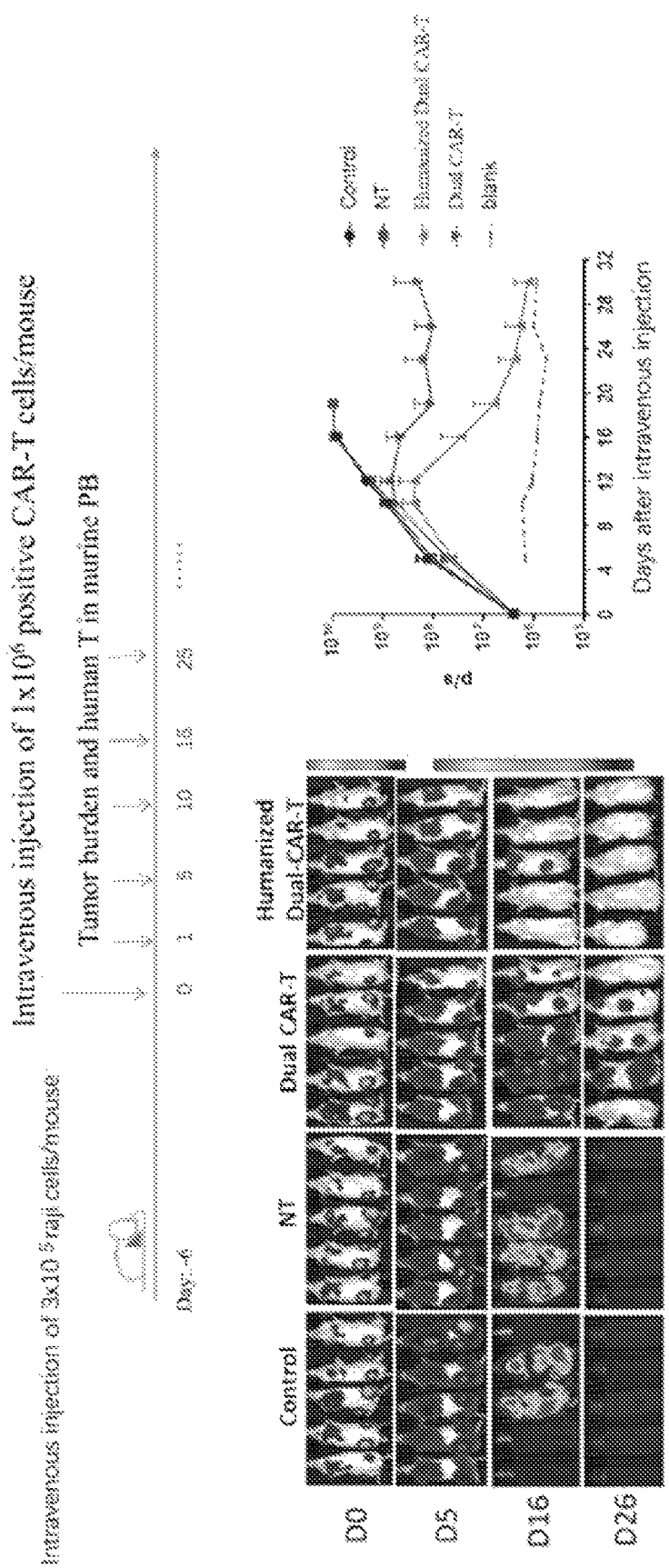
FIG. 21 shows the in vivo tumor elimination ability of different CAR-T cells against NOG cells of the Raji-Luc modeled. Compared with single CAR-T cells, dual CAR pairs have stronger ability of killing target cells.

The results are shown in FIG. 21. The humanized CAR-hS2 cells had a stronger ability to eliminate tumors in Raji cell-modeled mice than CAR-S2, indicating their significant anti-tumor efficacy.

Example 18 Killing of Raji Lymphoma Cells by CAR-T Cells

The luciferase-labeled Raji lymphoma target cells were used for the detection of the killing ability. By transferring the luciferase gene into the Raji target cells, stably transfected cell strain Raji-Luc was obtained after clonal screening. During the experiment, by adding a luciferin substrate, luciferase reacts with the luciferin to produce fluorescence, and by detecting the intensity of fluorescence, the activity of luciferase can be measured, then the survival ratio of the cells can be detected, and the killing effect of the CAR-T cells can be obtained.

Figure 22:
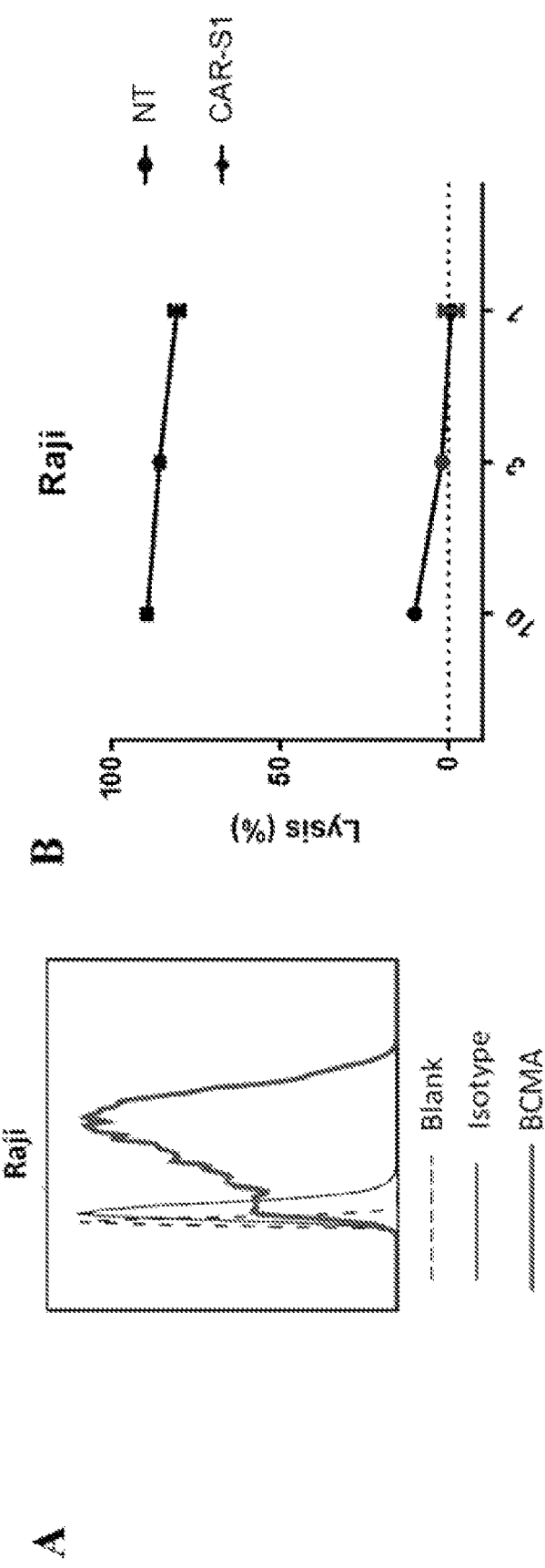

The results are shown in FIG. 22. NT cells had no killing function, and CAR-S1 cells had a dose-dependent killing effect on Raji-Luc cells (Raji cells transferred with luciferase genes), indicating their potential application value for indications such as lymphoma.

All documents mentioned in the present invention are cited as references in the present application, just as each document is individually incorporated as a reference. In addition, it should be understood that after reading the above teaching content of the present invention, those skilled in the art can make various changes or modifications to the present invention, and these equivalent forms also fall within the scope defined by the appended claims of the present application.

What is claimed is:

1. A bispecific chimeric antigen receptor (CAR) polypeptide, comprising:
   a first antigen binding domain exhibiting specific binding to CD19, comprising (i) a first heavy chain variable region ($V_{H,CD19}$) and (ii) a first light chain variable region ($V_{L,CD19}$); and
   a second antigen binding domain exhibiting specific binding to BCMA, comprising (i) a second heavy chain variable region ($V_{H,BCMA}$) that comprises the polypeptide sequence of SEQ ID NO: 9 and (ii) a second light chain variable region ($V_{L,BCMA}$) that comprises the polypeptide sequence of SEQ ID NO: 10,
   wherein the bispecific CAR polypeptide comprises a structure as shown in formula (I) or (II):

$$V_{L,CD19}\text{-the second antigen binding domain-}V_{H,CD19} \quad (I),$$

$$V_{H,CD19}\text{-the second antigen binding domain-}V_{L,CD19} \quad (II),$$

wherein "-" is each independently a linker peptide or a peptide bond.

2. The bispecific CAR polypeptide of claim 1, wherein the $V_{H,CD19}$ comprises the polypeptide sequence selected from the group consisting of SEQ ID NOs: 11 and 21-30, and wherein the $V_{L,CD19}$ comprises the polypeptide sequence selected from the group consisting of SEQ ID NOs: 12 and 31-36.

3. The bispecific CAR polypeptide of claim 2, wherein the $V_{H,CD19}$ comprises the polypeptide sequence of SEQ ID NO: 11, and wherein the $V_{L,CD19}$ comprises the polypeptide sequence of SEQ ID NO: 12.

4. The bispecific CAR polypeptide of claim 1, wherein the bispecific CAR polypeptide comprises the structure as shown in formula (I).

5. The bispecific CAR polypeptide of claim 1, wherein the bispecific CAR polypeptide comprises a structure as shown in formula III:

$$\text{L-}V_{L,CD19}\text{-}V_{H,BCMA}\text{-}V_{L,BCMA}\text{-}V_{H,CD19}\text{-H-TM-}C_2\text{-}C_1 \quad (III),$$

wherein:
"-" is each independently a linker peptide or a peptide bond;
L is absent or a signal domain;
H is absent or a hinge domain;
TM is a transmembrane domain;
$C_2$ is a costimulatory signaling domain; and
$C_1$ is a cytoplasmic signaling sequence derived from CD3ξ.

6. The bispecific CAR polypeptide of claim 5, wherein:
L comprises the polypeptide sequence of SEQ ID NO: 16;
$V_{L,CD19}$ comprises the polypeptide sequence of SEQ ID NO: 12;
$V_{H,BCMA}$ comprises the polypeptide sequence of SEQ ID NO: 9;
$V_{L,BCMA}$ comprises the polypeptide sequence of SEQ ID NO: 10;
$V_{H,CD19}$ comprises the polypeptide sequence of SEQ ID NO: 11;
H comprises the polypeptide sequence of SEQ ID NO: 38;
TM comprises the polypeptide sequence of SEQ ID NO: 7;
$C_2$ comprises the polypeptide sequence of SEQ ID NO: 5; and
$C_1$ comprises the polypeptide sequence of SEQ ID NO: 3.

7. The bispecific CAR polypeptide of claim 6, wherein:
(i) $V_{L,CD19}$ and $V_{H,BCMA}$ are coupled via a linker peptide comprising the polypeptide sequence of SEQ ID NO: 40;
(ii) $V_{H,BCMA}$ and $V_{L,BCMA}$ are coupled via a linker peptide comprising the polypeptide sequence of SEQ ID NO: 19; and
(iii) $V_{L,BCMA}$ and $V_{H,CD19}$ are coupled via a linker peptide comprising the polypeptide sequence of SEQ ID NO: 40.

8. The bispecific CAR polypeptide of claim 1, wherein the bispecific CAR polypeptide comprises the structure as shown in formula (I), and wherein an engineered T cell expressing the bispecific CAR polypeptide is characterized by exhibiting greater A cytotoxicity against target cells expressing BCMA, as compared to a control engineered T cell expressing a CAR polypeptide that comprises the first antigen binding domain and the second antigen binding domain in tandem.

9. The bispecific CAR polypeptide of claim 1, wherein the bispecific CAR polypeptide comprises the structure as shown in formula (I), and wherein an engineered T cell expressing the bispecific CAR polypeptide is characterized by exhibiting greater cytotoxicity against target cells expressing CD19, as compared to a control engineered T cell expressing a CAR polypeptide that comprises the first antigen binding domain and the second antigen binding domain in tandem.

10. An engineered immune cell comprising a bispecific chimeric antigen receptor (CAR) polypeptide, wherein the bispecific CAR comprises:
a first antigen binding domain exhibiting specific binding to CD19, comprising (i) a first heavy chain variable region ($V_{H,CD19}$) and (ii) a first light chain variable region ($V_{L,CD19}$); and
a second antigen binding domain exhibiting specific binding to BCMA, comprising (i) a second heavy chain variable region ($V_{H,BCMA}$) that comprises the polypeptide sequence of SEQ ID NO: 9 and (ii) a second light chain variable region ($V_{L,BCMA}$) that comprises the polypeptide sequence of SEQ ID NO: 10,
wherein the bispecific CAR polypeptide comprises a structure as shown in formula (I) or (II):

$$V_{L,CD19}\text{-the second antigen binding domain-}V_{H,CD19} \quad (I),$$

$$V_{H,CD19}\text{-the second antigen binding domain-}V_{L,CD19} \quad (II),$$

wherein "-" is each independently a linker peptide or a peptide bond.

11. The engineered immune cell of claim 10, wherein, in the bispecific CAR, the $V_{H,CD19}$ comprises the polypeptide sequence of SEQ ID NO: 11, and wherein the $V_{L\text{-}CD19}$ comprises the polypeptide sequence of SEQ ID NO: 12.

12. The bispecific CAR polypeptide of claim 10, wherein the bispecific CAR polypeptide comprises the structure as shown in formula (I).

13. The engineered immune cell of claim 10, wherein the bispecific CAR polypeptide comprises a structure as shown in formula III:

$$\text{L-}V_{L,CD19}\text{-}V_{H,BCMA}\text{-}V_{L,BCMA}\text{-}V_{H,CD19}\text{-H-TM-}C_2\text{-}C_1 \quad (III),$$

wherein:
"-" is each independently a linker peptide or a peptide bond;
L is absent or a signal domain;
H is absent or a hinge domain;
TM is a transmembrane domain;
$C_2$ is a costimulatory signaling domain; and
$C_1$ is a cytoplasmic signaling sequence derived from CD3ξ.

14. The engineered immune cell of claim 13, wherein:
L comprises the polypeptide sequence of SEQ ID NO: 16;
$V_{L,CD19}$ comprises the polypeptide sequence of SEQ ID NO: 12;
$V_{H,BCMA}$ comprises the polypeptide sequence of SEQ ID NO: 9;
$V_{L,BCMA}$ comprises the polypeptide sequence of SEQ ID NO: 10;
$V_{H,CD19}$ comprises the polypeptide sequence of SEQ ID NO: 11;
H comprises the polypeptide sequence of SEQ ID NO: 38;
TM comprises the polypeptide sequence of SEQ ID NO: 7;
$C_2$ comprises the polypeptide sequence of SEQ ID NO: 5; and
$C_1$ comprises the polypeptide sequence of SEQ ID NO: 3.

15. The engineered immune cell of claim 14, wherein:
(i) $V_{L,CD19}$ and $V_{H,BCMA}$ are coupled via a linker peptide comprising the polypeptide sequence of SEQ ID NO: 40;
(ii) $V_{H,BCMA}$ and $V_{L,BCMA}$ are coupled via a linker peptide comprising the polypeptide sequence of SEQ ID NO: 19; and
(iii) $V_{L,BCMA}$ and $V_{H,CD19}$ are coupled via a linker peptide comprising the polypeptide sequence of SEQ ID NO: 40.

16. The engineered immune cell of claim 10, wherein the engineered immune cell is an engineered T cell.

17. A method of treating a tumor or cancer of a subject in need thereof, the method comprising administering to the subject an engineered immune cell comprising a bispecific chimeric antigen receptor (CAR) polypeptide, wherein the bispecific CAR comprises:
a first antigen binding domain exhibiting specific binding to CD19, comprising (i) a first heavy chain variable region ($V_{H,CD19}$) and (ii) a first light chain variable region ($V_{L,CD19}$); and
a second antigen binding domain exhibiting specific binding to BCMA, comprising (i) a second heavy chain variable region ($V_{H,BCMA}$) that comprises the polypeptide sequence of SEQ ID NO: 9 and (ii) a second light chain variable region ($V_{L,BCMA}$) that comprises the polypeptide sequence of SEQ ID NO: 10,
wherein the bispecific CAR polypeptide comprises a structure as shown in formula (I) or (II):

$$V_{L,CD19}\text{-the second antigen binding domain-}V_{H,CD19} \quad (I),$$

$$V_{H,CD19}\text{-the second antigen binding domain-}V_{L,CD19} \quad (II),$$

wherein "-" is each independently a linker peptide or a peptide bond.

18. The method of claim 17, wherein, in the bispecific CAR, the $V_{H,CD19}$ comprises the polypeptide sequence of SEQ ID NO: 11, and wherein the $V_L$-CD19 comprises the polypeptide sequence of SEQ ID NO: 12.

19. The bispecific CAR polypeptide of claim 17, wherein the bispecific CAR polypeptide comprises the structure as shown in formula (I).

20. The method of claim 17, wherein the bispecific CAR polypeptide comprises a structure as shown in formula III:

$$L\text{-}V_{L,CD19}\text{-}V_{H,BCMA}\text{-}V_{L,BCMA}\text{-}V_{H,CD19}\text{-}H\text{-}TM\text{-}C_2\text{-}C_1 \quad \text{(III)},$$

wherein:
"-" is each independently a linker peptide or a peptide bond;
L is absent or a signal domain;
H is absent or a hinge domain;
TM is a transmembrane domain;
$C_2$ is a costimulatory signaling domain; and
$C_1$ is a cytoplasmic signaling sequence derived from CD3ξ.

21. The method of claim 20, wherein:
L comprises the polypeptide sequence of SEQ ID NO: 16;
$V_{L,CD19}$ comprises the polypeptide sequence of SEQ ID NO: 12;
$V_{H,BCMA}$ comprises the polypeptide sequence of SEQ ID NO: 9;
$V_{L,BCMA}$ comprises the polypeptide sequence of SEQ ID NO: 10;
$V_{H,CD19}$ comprises the polypeptide sequence of SEQ ID NO: 11;
H comprises the polypeptide sequence of SEQ ID NO: 38;
TM comprises the polypeptide sequence of SEQ ID NO: 7;
$C_2$ comprises the polypeptide sequence of SEQ ID NO: 5; and
$C_1$ comprises the polypeptide sequence of SEQ ID NO: 3.

22. The method of claim 21, wherein:
(i) $V_{L,CD19}$ and $V_{H,BCMA}$ are coupled via a linker peptide comprising the polypeptide sequence of SEQ ID NO: 40;
(ii) $V_{H,BCMA}$ and $V_{L,BCMA}$ are coupled via a linker peptide comprising the polypeptide sequence of SEQ ID NO: 19; and
(iii) $V_{L,BCMA}$ and $V_{H,CD19}$ are coupled via a linker peptide comprising the polypeptide sequence of SEQ ID NO: 40.

23. The method of claim 17, wherein the engineered immune cell is derived from an autologous cell of the subject.

24. The method of claim 17, wherein the engineered immune cell is allogeneic to the subject.

25. The method of claim 17, wherein the engineered immune cell is an engineered T cell.

26. The bispecific CAR polypeptide of claim 1, wherein the bispecific CAR polypeptide comprises the structure as shown in formula (II).

27. The engineered immune cell of claim 10, wherein the bispecific CAR polypeptide comprises the structure as shown in formula (II).

28. The method of claim 17, wherein the bispecific CAR polypeptide comprises the structure as shown in formula (II).

* * * * *